(12) United States Patent
Merkamm et al.

(10) Patent No.: US 9,803,225 B2
(45) Date of Patent: Oct. 31, 2017

(54) MEANS AND METHODS FOR THE ENZYMATIC PRODUCTION OF L-METHIONINE FROM O-PHOSPHO-L-HOMOSERINE AND METHANETHIOL

(71) Applicant: ADISSEO FRANCE S.A.S., Antony (FR)

(72) Inventors: Muriel Merkamm, Les Ulis (FR); Dominique Louis, Forges les Bains (FR); Karine Jaillardon, Saint Michel sur Orge (FR); Dominique Thomas, Gif sur Yvette (FR); Philippe Marliere, Mouscron (BE)

(73) Assignee: ADISSEO FRANCE S.A.S., Antony (FR)

( * ) Notice: Subject to any disclaimer, the term of this patent is extended or adjusted under 35 U.S.C. 154(b) by 361 days.

(21) Appl. No.: 14/438,847

(22) PCT Filed: Oct. 25, 2013

(86) PCT No.: PCT/EP2013/072380
§ 371 (c)(1),
(2) Date: Apr. 27, 2015

(87) PCT Pub. No.: WO2014/064244
PCT Pub. Date: May 1, 2014

(65) Prior Publication Data
US 2015/0275247 A1 Oct. 1, 2015

(30) Foreign Application Priority Data
Oct. 26, 2012 (EP) ..................... 12190150

(51) Int. Cl.
| | | |
|---|---|---|
| *C12P 13/12* | (2006.01) | |
| *C12P 19/40* | (2006.01) | |
| *C12P 21/02* | (2006.01) | |
| *C12P 11/00* | (2006.01) | |
| *C12P 13/02* | (2006.01) | |
| *C12N 9/10* | (2006.01) | |

(52) U.S. Cl.
CPC ............ *C12P 13/12* (2013.01); *C12N 9/1085* (2013.01); *C12P 11/00* (2013.01); *C12P 13/02* (2013.01); *C12P 19/40* (2013.01); *C12P 21/02* (2013.01); *C12Y 205/01048* (2013.01)

(58) Field of Classification Search
None
See application file for complete search history.

(56) References Cited

FOREIGN PATENT DOCUMENTS

| WO | 93/17112 A1 | 9/1993 |
|---|---|---|
| WO | 2011/031285 A1 | 3/2011 |

OTHER PUBLICATIONS

Chiba et al. (Evidence for Autoregulation of Cystathionine y-Synthase mRNA Stability in Arabidopsis, Science, vol. 286, Nov. 12, pp. 1371-1374).*
Hacham et al. (Overexpression of mutated forms of aspartate kinase and cystathionine c-synthase in tobacco leaves resulted in the high accumulation of methionine and threonine, The Plant Journal (2008) 54, 260-271).*
Kreft, B.D., et al., Purification and Properties of Cystathionine Gamma-Synthase from Wheat (*Triticum aestivum* L.), Plant Physiol., 1994, pp. 1215-1220, vol. 104.
Vartanian, J. et al., "Hypermutagenic PCR involving all four transitions and a sizable proportion of transversions," Nucleic Acids Research, 1996, pp. 2627-2631, vol. 24, No. 14.
Jul. 1, 2014 International Search Report issued in International Patent Application No. PCT/EP2013/072380.

* cited by examiner

*Primary Examiner* — Suzanne M Noakes
*Assistant Examiner* — Jae W Lee
(74) *Attorney, Agent, or Firm* — Oliff PLC

(57) ABSTRACT

Provided is a method for producing L-methionine in which O-phospho-L-homoserine and methanethiol are enzymatically converted into L-methionine and H3PO4. Such a conversion is achieved by an enzyme called O-phospho-L-homoserine (OHPS) dependent methionine synthase. Also described are O-phospho-L-homoserine (OHPS) dependent methionine synthases, i.e. proteins which are able to enzymatically convert O-phospho-L-homoserine and methanethiol into L-methionine and H3PO4 as well as microorganisms which have been genetically modified so as to be able to produce L-methionine from O-phospho-L-homoserine and methanethiol. Furthermore described are methods to screen for enzymes that catalyze the conversion of O-phospho-L-homoserine and methanethiol into L-methionine and $H_3PO_4$.

12 Claims, 13 Drawing Sheets

Figure 7B (continued)

```
                                   570           580
                                ....|....|....|....|...
CGS1 A. thaliana AAC25687.1     EAI
CGS1 G84S A. thaliana           :::
MUT02 CGS1-4                    ..:*
MUT04 CGS1-4                    ..:*
MUT13 CGS1-4                    ...WGSTSSRAAAAAVGEFLMIYDFYY*
MUT18 CGS1-4                    ..:*
MUT19 CGS1-4                    ..:*
AD309 CGS1-5                    ..:*
AD310 CGS1-5                    ..:*
AD311 CGS1-5                    ..:*
AD312 CGS1-5                    ..:*
AD313 CGS1-5                    ..:*
AD242 CGS1-1                    ..:*
AD328 CGS1-1                    ..:*
AD329 CGS1-1                    .G.*
MUT24 CGS1-1                    ..:*
MUT27 CGS1-1                    ..:*
MUT67 CGS1-1                    ..:*
MUT68 CGS1-1                    ..:*
MUT70 CGS1-1                    ..:*
MUT71 CGS1-1                    ..V*
MUT72 CGS1-1                    ..V*
MUT74 CGS1-1                    ..:*
MUT75 CGS1-1                    ..V*
MUT78 CGS1-1                    ..:*
MUT79 CGS1-1                    ..:*
```

Figure 7D (continued)

SEQUENCE LISTING

<160> NUMBER OF SEQ ID NOS: 29

<210> SEQ ID NO 1
<211> LENGTH: 563
<212> TYPE: PRT
<213> ORGANISM: Arabidopsis thaliana

<400> SEQUENCE: 1

```
Met Ala Val Ser Ser Phe Gln Ser Pro Thr Ile Phe Ser Ser Ser
1               5                   10                  15

Ile Ser Gly Phe Gln Cys Arg Ser Asp Pro Asp Leu Val Gly Ser Pro
            20                  25                  30

Val Gly Gly Ser Ser Arg Arg Arg Val His Ala Ser Ala Gly Ile Ser
        35                  40                  45

Ser Ser Phe Thr Gly Asp Gly Gly Leu Ser Ser Arg Ile Leu Arg Phe
    50                  55                  60

Pro Pro Asn Phe Val Arg Gln Leu Ser Ile Lys Ala Arg Arg Asn Cys
65                  70                  75                  80

Ser Asn Ile Gly Val Ala Gln Ile Val Ala Gly Lys Trp Ser Asn Asn
                85                  90                  95

Pro Ser Ser Ala Leu Pro Ser Ala Ala Ala Ala Ala Thr Ser Ser
            100                 105                 110

Ala Ser Ala Val Ser Ser Ala Ser Ala Ala Ala Ser Ser Ala
        115                 120                 125

Ala Ala Ala Pro Val Ala Ala Pro Pro Val Val Leu Lys Ser Val
130                 135                 140

Asp Glu Glu Val Val Val Ala Glu Glu Gly Ile Arg Glu Lys Ile Gly
145                 150                 155                 160

Ser Val Gln Leu Thr Asp Ser Lys His Ser Phe Leu Ser Ser Asp Gly
                165                 170                 175

Ser Leu Thr Val His Ala Gly Leu Arg Leu Gly Arg Gly Ile Val Thr
            180                 185                 190

Asp Ala Ile Thr Thr Pro Val Val Asn Thr Ser Ala Tyr Phe Phe Lys
        195                 200                 205

Lys Thr Ala Glu Leu Ile Asp Phe Lys Glu Lys Arg Ser Val Ser Phe
210                 215                 220

Glu Tyr Gly Arg Tyr Gly Asn Pro Thr Thr Val Val Leu Glu Asp Lys
225                 230                 235                 240

Ile Ser Ala Leu Glu Gly Ala Glu Ser Thr Leu Val Met Ala Ser Gly
                245                 250                 255

Met Cys Ala Ser Thr Val Met Leu Leu Ala Leu Val Pro Ala Gly Gly
            260                 265                 270

His Ile Val Thr Thr Thr Asp Cys Tyr Arg Lys Thr Arg Ile Phe Met
        275                 280                 285

Glu Asn Phe Leu Pro Lys Leu Gly Ile Thr Val Thr Val Ile Asp Pro
    290                 295                 300

Ala Asp Ile Ala Gly Leu Glu Ala Ala Val Asn Glu Phe Lys Val Ser
305                 310                 315                 320

Leu Phe Phe Thr Glu Ser Pro Thr Asn Pro Phe Leu Arg Cys Val Asp
                325                 330                 335

Ile Glu Leu Val Ser Lys Ile Cys His Lys Arg Gly Thr Leu Val Cys
            340                 345                 350

Ile Asp Gly Thr Phe Ala Thr Pro Leu Asn Gln Lys Ala Leu Ala Leu
        355                 360                 365
```

```
Gly Ala Asp Leu Val Val His Ser Ala Thr Lys Tyr Ile Gly Gly His
    370                 375                 380

Asn Asp Val Leu Ala Gly Cys Ile Cys Gly Ser Leu Lys Leu Val Ser
385                 390                 395                 400

Glu Ile Arg Asn Leu His His Val Leu Gly Gly Pro Leu Asn Pro Asn
                405                 410                 415

Ala Ala Tyr Leu Ile Ile Arg Gly Met Lys Thr Leu His Leu Arg Val
            420                 425                 430

Gln Gln Gln Asn Ser Thr Ala Phe Arg Met Ala Glu Ile Leu Glu Ala
        435                 440                 445

His Pro Lys Val Ser His Val Tyr Tyr Pro Gly Leu Pro Ser His Pro
450                 455                 460

Glu His Glu Leu Ala Lys Arg Gln Met Thr Gly Phe Gly Gly Val Val
465                 470                 475                 480

Ser Phe Glu Ile Asp Gly Asp Ile Glu Thr Thr Ile Lys Phe Val Asp
                485                 490                 495

Ser Leu Lys Ile Pro Tyr Ile Ala Pro Ser Phe Gly Gly Cys Glu Ser
            500                 505                 510

Ile Val Asp Gln Pro Ala Ile Met Ser Tyr Trp Asp Leu Pro Gln Glu
        515                 520                 525

Glu Arg Leu Lys Tyr Gly Ile Lys Asp Asn Leu Val Arg Phe Ser Phe
    530                 535                 540

Gly Val Glu Asp Phe Glu Asp Val Lys Ala Asp Ile Leu Gln Ala Leu
545                 550                 555                 560

Glu Ala Ile

<210> SEQ ID NO 2
<211> LENGTH: 563
<212> TYPE: PRT
<213> ORGANISM: Arabidopsis thaliana

<400> SEQUENCE: 2

Met Ala Val Ser Ser Phe Gln Ser Pro Thr Ile Phe Ser Ser Ser Ser
1               5                   10                  15

Ile Ser Gly Phe Gln Cys Arg Ser Asp Pro Leu Val Gly Ser Pro
            20                  25                  30

Val Gly Gly Ser Ser Arg Arg Arg Val His Ala Ser Ala Gly Ile Ser
        35                  40                  45

Ser Ser Phe Thr Gly Asp Gly Gly Leu Ser Ser Arg Ile Leu Arg Phe
    50                  55                  60

Pro Pro Asn Phe Val Arg Gln Leu Ser Ile Lys Ala Arg Arg Asn Cys
65                  70                  75                  80

Ser Asn Ile Ser Val Ala Gln Ile Val Ala Gly Lys Trp Ser Asn Asn
                85                  90                  95

Pro Ser Ser Ala Leu Pro Ser Ala Ala Ala Ala Ala Thr Ser Ser
            100                 105                 110

Ala Ser Ala Val Ser Ser Ala Ala Ser Ala Ala Ala Ser Ser Ala
        115                 120                 125

Ala Ala Ala Pro Val Ala Ala Pro Pro Val Val Leu Lys Ser Val
    130                 135                 140

Asp Glu Glu Val Val Val Ala Glu Glu Gly Ile Arg Glu Lys Ile Gly
145                 150                 155                 160

Ser Val Gln Leu Thr Asp Ser Lys His Ser Phe Leu Ser Ser Asp Gly
                165                 170                 175
```

Ser Leu Thr Val His Ala Gly Glu Arg Leu Gly Arg Gly Ile Val Thr
            180                 185                 190

Asp Ala Ile Thr Thr Pro Val Val Asn Thr Ser Ala Tyr Phe Phe Lys
        195                 200                 205

Lys Thr Ala Glu Leu Ile Asp Phe Lys Glu Lys Arg Ser Val Ser Phe
210                 215                 220

Glu Tyr Gly Arg Tyr Gly Asn Pro Thr Thr Val Val Leu Glu Asp Lys
225                 230                 235                 240

Ile Ser Ala Leu Glu Gly Ala Glu Ser Thr Leu Val Met Ala Ser Gly
                245                 250                 255

Met Cys Ala Ser Thr Val Met Leu Leu Ala Leu Val Pro Ala Gly Gly
            260                 265                 270

His Ile Val Thr Thr Thr Asp Cys Tyr Arg Lys Thr Arg Ile Phe Met
        275                 280                 285

Glu Asn Phe Leu Pro Lys Leu Gly Ile Thr Val Thr Val Ile Asp Pro
290                 295                 300

Ala Asp Ile Ala Gly Leu Glu Ala Ala Val Asn Glu Phe Lys Val Ser
305                 310                 315                 320

Leu Phe Phe Thr Glu Ser Pro Thr Asn Pro Phe Leu Arg Cys Val Asp
                325                 330                 335

Ile Glu Leu Val Ser Lys Ile Cys His Lys Arg Gly Thr Leu Val Cys
            340                 345                 350

Ile Asp Gly Thr Phe Ala Thr Pro Leu Asn Gln Lys Ala Leu Ala Leu
        355                 360                 365

Gly Ala Asp Leu Val Val His Ser Ala Thr Lys Tyr Ile Gly Gly His
370                 375                 380

Asn Asp Val Leu Ala Gly Cys Ile Cys Gly Ser Leu Lys Leu Val Ser
385                 390                 395                 400

Glu Ile Arg Asn Leu His His Val Leu Gly Gly Pro Leu Asn Pro Asn
                405                 410                 415

Ala Ala Tyr Leu Ile Ile Arg Gly Met Lys Thr Leu His Leu Arg Val
            420                 425                 430

Gln Gln Gln Asn Ser Thr Ala Phe Arg Met Ala Glu Ile Leu Glu Ala
        435                 440                 445

His Pro Lys Val Ser His Val Tyr Tyr Pro Gly Leu Pro Ser His Pro
450                 455                 460

Glu His Glu Leu Ala Lys Arg Gln Met Thr Gly Phe Gly Gly Val Val
465                 470                 475                 480

Ser Phe Glu Ile Asp Gly Asp Ile Glu Thr Thr Ile Lys Phe Val Asp
                485                 490                 495

Ser Leu Lys Ile Pro Tyr Ile Ala Pro Ser Phe Gly Gly Cys Glu Ser
            500                 505                 510

Ile Val Asp Gln Pro Ala Ile Met Ser Tyr Trp Asp Leu Pro Gln Glu
        515                 520                 525

Glu Arg Leu Lys Tyr Gly Ile Lys Asp Asn Leu Val Arg Phe Ser Phe
530                 535                 540

Gly Val Glu Asp Phe Glu Asp Val Lys Ala Asp Ile Leu Gln Ala Leu
545                 550                 555                 560

Glu Ala Ile

<210> SEQ ID NO 3
<211> LENGTH: 507
<212> TYPE: PRT
<213> ORGANISM: Arabidopsis thaliana

<400> SEQUENCE: 3

```
Met Ser Ser Arg Ile Leu Arg Phe Pro Pro Asn Phe Val Arg Gln Leu
1               5                   10                  15

Ser Ile Lys Ala Arg Arg Asn Cys Ser Asn Ile Ser Val Ala Gln Ile
            20                  25                  30

Val Ala Gly Lys Trp Ser Asn Asn Pro Ser Ser Ala Leu Pro Ser Ala
        35                  40                  45

Ala Ala Ala Ala Ala Thr Ser Ser Ala Ser Ala Val Ser Ser Ala Ala
        50                  55                  60

Ser Ala Ala Ala Ala Ser Ser Ala Ala Ala Pro Val Ala Ala Ala
65                  70                  75                  80

Pro Pro Val Val Leu Lys Ser Val Asp Glu Glu Val Val Ala Glu
                85                  90                  95

Glu Gly Ile Arg Glu Lys Ile Gly Ser Val Gln Leu Thr Asp Ser Lys
                100                 105                 110

His Ser Phe Leu Ser Ser Asp Gly Ser Leu Thr Val His Ala Gly Glu
            115                 120                 125

Arg Leu Gly Arg Gly Ile Val Thr Asp Ala Ile Thr Thr Pro Val Val
130                 135                 140

Asn Thr Ser Ala Tyr Phe Phe Lys Lys Thr Ala Glu Leu Ile Asp Phe
145                 150                 155                 160

Lys Glu Lys Arg Ser Val Ser Phe Glu Tyr Gly Arg Tyr Gly Asn Pro
                165                 170                 175

Thr Thr Val Val Leu Glu Asp Lys Ile Ser Ala Leu Glu Gly Ala Glu
            180                 185                 190

Ser Thr Leu Val Met Ala Ser Gly Met Cys Ala Ser Thr Val Met Leu
            195                 200                 205

Leu Ala Leu Val Pro Ala Gly Gly His Ile Val Thr Thr Thr Asp Cys
210                 215                 220

Tyr Arg Lys Thr Arg Ile Phe Met Glu Asn Phe Leu Pro Lys Leu Gly
225                 230                 235                 240

Ile Thr Val Thr Val Ile Asp Pro Ala Asp Ile Ala Gly Leu Glu Ala
                245                 250                 255

Ala Val Asn Glu Phe Lys Val Ser Leu Phe Phe Thr Glu Ser Pro Thr
            260                 265                 270

Asn Pro Phe Leu Arg Cys Val Asp Ile Glu Leu Val Ser Lys Ile Cys
            275                 280                 285

His Lys Arg Gly Thr Leu Val Cys Ile Asp Gly Thr Phe Ala Thr Pro
290                 295                 300

Leu Asn Gln Lys Ala Leu Ala Leu Gly Ala Asp Leu Val Val His Ser
305                 310                 315                 320

Ala Thr Lys Tyr Ile Gly Gly His Asn Asp Val Leu Ala Gly Cys Ile
                325                 330                 335

Cys Gly Ser Leu Lys Leu Val Ser Glu Ile Arg Asn Leu His His Val
            340                 345                 350

Leu Gly Gly Pro Leu Asn Pro Asn Ala Ala Tyr Leu Ile Ile Arg Gly
            355                 360                 365

Met Lys Thr Leu His Leu Arg Val Gln Gln Asn Ser Thr Ala Phe
            370                 375                 380

Arg Met Ala Glu Ile Leu Glu Ala His Pro Lys Val Ser His Val Tyr
385                 390                 395                 400

Tyr Pro Gly Leu Pro Ser His Pro Glu His Glu Leu Ala Lys Arg Gln
```

```
            405                 410                 415
Met Thr Gly Phe Gly Gly Val Val Ser Phe Glu Ile Asp Gly Asp Ile
            420                 425                 430

Glu Thr Thr Ile Lys Phe Val Asp Ser Leu Lys Ile Pro Tyr Ile Ala
            435                 440                 445

Pro Ser Phe Gly Gly Cys Glu Ser Ile Val Asp Gln Pro Ala Ile Met
            450                 455                 460

Ser Tyr Trp Asp Leu Pro Gln Glu Arg Leu Lys Tyr Gly Ile Lys
465                 470                 475                 480

Asp Asn Leu Val Arg Phe Ser Phe Gly Val Glu Asp Phe Glu Asp Val
                    485                 490                 495

Lys Ala Asp Ile Leu Gln Ala Leu Glu Ala Ile
                    500                 505

<210> SEQ ID NO 4
<211> LENGTH: 476
<212> TYPE: PRT
<213> ORGANISM: Arabidopsis thaliana

<400> SEQUENCE: 4

Met Val Ala Gly Lys Trp Ser Asn Asn Pro Ser Ser Ala Leu Pro Ser
1               5                   10                  15

Ala Ala Ala Ala Ala Ala Thr Ser Ser Ala Ser Ala Val Ser Ser Ala
                20                  25                  30

Ala Ser Ala Ala Ala Ser Ser Ala Ala Ala Pro Val Ala Ala
            35                  40                  45

Ala Pro Pro Val Val Leu Lys Ser Val Asp Glu Val Val Ala
50                  55                  60

Glu Glu Gly Ile Arg Glu Lys Ile Gly Ser Val Gln Leu Thr Asp Ser
65                  70                  75                  80

Lys His Ser Phe Leu Ser Ser Asp Gly Ser Leu Thr Val His Ala Gly
                85                  90                  95

Glu Arg Leu Gly Arg Gly Ile Val Thr Asp Ala Ile Thr Thr Pro Val
            100                 105                 110

Val Asn Thr Ser Ala Tyr Phe Lys Lys Thr Ala Glu Leu Ile Asp
            115                 120                 125

Phe Lys Glu Lys Arg Ser Val Ser Phe Glu Tyr Gly Arg Tyr Gly Asn
130                 135                 140

Pro Thr Thr Val Val Leu Glu Asp Lys Ile Ser Ala Leu Glu Gly Ala
145                 150                 155                 160

Glu Ser Thr Leu Val Met Ala Ser Gly Met Cys Ala Ser Thr Val Met
                165                 170                 175

Leu Leu Ala Leu Val Pro Ala Gly Gly His Ile Val Thr Thr Asp
            180                 185                 190

Cys Tyr Arg Lys Thr Arg Ile Phe Met Glu Asn Phe Leu Pro Lys Leu
            195                 200                 205

Gly Ile Thr Val Thr Val Ile Asp Pro Ala Asp Ile Ala Gly Leu Glu
210                 215                 220

Ala Ala Val Asn Glu Phe Lys Val Ser Leu Phe Phe Thr Glu Ser Pro
225                 230                 235                 240

Thr Asn Pro Phe Leu Arg Cys Val Asp Ile Glu Leu Val Ser Lys Ile
                245                 250                 255

Cys His Lys Arg Gly Thr Leu Val Cys Ile Asp Gly Thr Phe Ala Thr
            260                 265                 270
```

```
Pro Leu Asn Gln Lys Ala Leu Ala Leu Gly Ala Asp Leu Val Val His
            275                 280                 285

Ser Ala Thr Lys Tyr Ile Gly Gly His Asn Asp Val Leu Ala Gly Cys
290                 295                 300

Ile Cys Gly Ser Leu Lys Leu Val Ser Glu Ile Arg Asn Leu His His
305                 310                 315                 320

Val Leu Gly Gly Pro Leu Asn Pro Asn Ala Ala Tyr Leu Ile Ile Arg
                325                 330                 335

Gly Met Lys Thr Leu His Leu Arg Val Gln Gln Asn Ser Thr Ala
            340                 345                 350

Phe Arg Met Ala Glu Ile Leu Glu Ala His Pro Lys Val Ser His Val
        355                 360                 365

Tyr Tyr Pro Gly Leu Pro Ser His Pro Glu His Glu Leu Ala Lys Arg
    370                 375                 380

Gln Met Thr Gly Phe Gly Val Val Ser Phe Glu Ile Asp Gly Asp
385                 390                 395                 400

Ile Glu Thr Thr Ile Lys Phe Val Asp Ser Leu Lys Ile Pro Tyr Ile
                405                 410                 415

Ala Pro Ser Phe Gly Gly Cys Glu Ser Ile Val Asp Gln Pro Ala Ile
                420                 425                 430

Met Ser Tyr Trp Asp Leu Pro Gln Glu Glu Arg Leu Lys Tyr Gly Ile
            435                 440                 445

Lys Asp Asn Leu Val Arg Phe Ser Phe Gly Val Glu Asp Phe Glu Asp
        450                 455                 460

Val Lys Ala Asp Ile Leu Gln Ala Leu Glu Ala Ile
465                 470                 475

<210> SEQ ID NO 5
<211> LENGTH: 404
<212> TYPE: PRT
<213> ORGANISM: Arabidopsis thaliana

<400> SEQUENCE: 5

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Val Asn Thr Ser Ala Tyr Phe Phe
        35                  40                  45

Lys Lys Thr Ala Glu Leu Ile Asp Phe Lys Glu Lys Arg Ser Val Ser
    50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
    130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Phe Leu Arg Cys Val
                165                 170                 175
```

```
Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
    210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Pro Leu Asn Pro
                245                 250                 255

Asn Ala Ala Tyr Leu Ile Ile Arg Gly Met Lys Thr Leu His Leu Arg
                260                 265                 270

Val Gln Gln Gln Asn Ser Thr Ala Phe Arg Met Ala Glu Ile Leu Glu
            275                 280                 285

Ala His Pro Lys Val Ser His Val Tyr Tyr Pro Gly Leu Pro Ser His
        290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
                340                 345                 350

Ser Ile Val Asp Gln Pro Ala Ile Met Ser Tyr Trp Asp Leu Pro Gln
            355                 360                 365

Glu Glu Arg Leu Lys Tyr Gly Ile Lys Asp Asn Leu Val Arg Phe Ser
        370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 6
<211> LENGTH: 507
<212> TYPE: PRT
<213> ORGANISM: Arabidopsis thaliana

<400> SEQUENCE: 6

Met Ser Ser Arg Ile Leu Arg Phe Pro Pro Asn Phe Val Arg Gln Leu
1               5                   10                  15

Ser Ile Lys Ala Arg Arg Asn Cys Ser Asn Ile Ser Val Ala Gln Ile
            20                  25                  30

Val Ala Gly Lys Trp Ser Asn Asn Pro Ser Ser Ala Leu Pro Ser Ala
        35                  40                  45

Ala Ala Ala Ala Thr Ser Ser Ala Ser Ala Val Ser Ser Ala Ala
    50                  55                  60

Ser Ala Ala Ala Ser Ser Ala Ala Ala Pro Val Ala Ala
65                  70                  75                  80

Pro Pro Val Val Leu Lys Ser Val Asp Glu Val Val Ala Glu
                85                  90                  95

Glu Gly Ile Arg Glu Lys Ile Gly Ser Val Gln Leu Thr Asp Ser Lys
            100                 105                 110

His Ser Phe Leu Ser Ser Asp Gly Ser Leu Thr Val His Ala Gly Glu
        115                 120                 125

Arg Leu Gly Arg Gly Ile Val Thr Asp Ala Ile Thr Thr Pro Val Val
    130                 135                 140
```

Asn Thr Ser Ala Tyr Phe Phe Lys Lys Thr Ala Glu Leu Ile Asp Phe
145                 150                 155                 160

Lys Glu Lys Arg Ser Val Ser Phe Glu Tyr Gly Arg Tyr Gly Asn Pro
            165                 170                 175

Thr Thr Val Val Leu Glu Asp Lys Ile Ser Ala Leu Glu Gly Ala Glu
        180                 185                 190

Ser Thr Leu Val Met Ala Ser Gly Met Cys Ala Ser Thr Val Met Leu
    195                 200                 205

Leu Ala Leu Val Pro Ala Gly Gly His Ile Val Thr Thr Asp Cys
210                 215                 220

Tyr Arg Lys Thr Arg Ile Phe Met Glu Asn Phe Leu Pro Lys Leu Gly
225                 230                 235                 240

Ile Thr Val Thr Val Ile Asp Pro Ala Asp Ile Ala Gly Leu Glu Ala
                245                 250                 255

Ala Val Asn Glu Phe Lys Val Ser Leu Phe Phe Thr Glu Ser Pro Thr
            260                 265                 270

Asn Pro Phe Leu Arg Cys Val Asp Ile Glu Leu Val Ser Lys Ile Cys
        275                 280                 285

His Lys Arg Gly Thr Leu Val Cys Ile Asp Gly Thr Phe Ala Thr Pro
    290                 295                 300

Leu Asn Gln Lys Ala Leu Ala Leu Gly Ala Asp Leu Val Val His Ser
305                 310                 315                 320

Ala Thr Lys Tyr Ile Gly Gly His Asn Asp Val Leu Ala Gly Cys Ile
                325                 330                 335

Cys Gly Ser Leu Lys Leu Val Ser Glu Ile Arg Asn Leu His His Val
            340                 345                 350

Leu Gly Gly Thr Leu Asn Pro Asn Ala Ala Tyr Leu Ile Ile Arg Gly
        355                 360                 365

Met Lys Thr Leu His Leu Arg Val Gln Gln Gln Asn Ser Thr Ala Phe
    370                 375                 380

Arg Met Ala Glu Ile Leu Glu Ala His Pro Lys Val Ser His Val Tyr
385                 390                 395                 400

Tyr Pro Gly Leu Pro Ser His Pro Glu His Glu Leu Ala Lys Arg Gln
                405                 410                 415

Met Thr Gly Phe Gly Gly Val Val Ser Phe Glu Ile Asp Gly Asp Ile
            420                 425                 430

Glu Thr Thr Ile Lys Phe Val Asp Ser Leu Lys Ile Pro Tyr Ile Ala
        435                 440                 445

Pro Ser Phe Gly Gly Cys Glu Ser Ile Val Asp Gln Pro Ala Ile Met
    450                 455                 460

Ser Tyr Trp Asp Leu Pro Gln Glu Glu Arg Leu Lys Tyr Gly Ile Lys
465                 470                 475                 480

Asp Asn Leu Val Arg Phe Ser Phe Gly Val Glu Asp Phe Glu Asp Val
                485                 490                 495

Lys Ala Asp Ile Leu Gln Ala Leu Glu Ala Ile
            500                 505

<210> SEQ ID NO 7
<211> LENGTH: 507
<212> TYPE: PRT
<213> ORGANISM: Arabidopsis thaliana

<400> SEQUENCE: 7

Met Ser Ser Arg Ile Leu Arg Phe Pro Leu Asn Phe Val Arg Gln Leu

-continued

```
1               5                   10                  15
Ser Ile Lys Ala Arg Asn Cys Ser Asn Ser Val Ala Gln Ile
            20                  25                  30
Val Ala Gly Lys Trp Ser Asn Pro Ser Ser Ala Leu Pro Ser Ala
            35                  40                  45
Ala Ala Ala Ala Ala Thr Ser Ser Ala Ser Ala Asp Ser Ser Ala Ala
            50                  55                  60
Ser Ala Ala Ala Ala Ser Ser Ala Ala Ala Pro Val Ala Ala
65                  70                  75                  80
Pro Pro Val Val Leu Lys Ser Val Asp Glu Val Val Ala Glu
                    85                  90                  95
Glu Gly Ile Arg Glu Lys Ile Gly Ser Val Gln Leu Thr Asp Ser Lys
                    100                 105                 110
His Ser Phe Leu Ser Ser Asp Gly Ser Leu Thr Val His Ala Gly Glu
                    115                 120                 125
Arg Leu Gly Arg Gly Ile Val Thr Asp Ala Ile Thr Thr Pro Val Val
                    130                 135                 140
Asn Thr Ser Ala Tyr Phe Phe Lys Lys Thr Ala Glu Leu Ile Asp Phe
145                 150                 155                 160
Lys Glu Lys Arg Ser Val Ser Phe Glu Tyr Gly Arg Tyr Gly Asn Pro
                    165                 170                 175
Thr Thr Val Val Leu Glu Asp Lys Ile Ser Ala Leu Glu Gly Ala Glu
                    180                 185                 190
Ser Thr Leu Val Met Ala Ser Gly Met Cys Ala Ser Thr Val Met Leu
                    195                 200                 205
Leu Ala Leu Val Pro Ala Gly Gly His Ile Val Thr Thr Thr Asp Cys
210                 215                 220
Tyr Arg Lys Thr Arg Ile Phe Met Glu Asn Phe Leu Pro Lys Leu Gly
225                 230                 235                 240
Ile Thr Val Thr Val Ile Asp Pro Ala Asp Ile Ala Gly Leu Glu Ala
                    245                 250                 255
Ala Val Asn Glu Phe Lys Val Ser Leu Phe Phe Thr Glu Ser Pro Thr
                    260                 265                 270
Asn Pro Phe Leu Arg Cys Val Asp Ile Glu Leu Val Ser Lys Ile Cys
                    275                 280                 285
His Lys Arg Gly Thr Leu Val Cys Ile Asp Gly Thr Phe Ala Thr Pro
                    290                 295                 300
Leu Asn Gln Lys Ala Leu Ala Leu Gly Ala Asp Leu Val His Ser
305                 310                 315                 320
Ala Thr Lys Phe Ile Gly Gly His Asn Asp Val Leu Ala Gly Cys Ile
                    325                 330                 335
Cys Gly Ser Leu Lys Leu Val Ser Glu Ile Arg Asn Leu His His Val
                    340                 345                 350
Leu Gly Gly Pro Leu Asn Pro Asn Ala Ala Tyr Leu Ile Ile Arg Gly
                    355                 360                 365
Met Lys Thr Leu His Leu Arg Val Gln Gln Gln Asn Ser Thr Ala Phe
                    370                 375                 380
Arg Met Ala Glu Ile Leu Glu Ala His Pro Lys Val Ser His Val Tyr
385                 390                 395                 400
Tyr Pro Gly Leu Pro Ser His Pro Glu His Glu Leu Ala Lys Arg Gln
                    405                 410                 415
Met Thr Gly Phe Gly Gly Val Val Ser Phe Glu Ile Asp Gly Asp Ile
                    420                 425                 430
```

Glu Thr Thr Ile Lys Phe Val Asp Ser Leu Lys Ile Pro Tyr Ile Ala
            435                 440                 445

Pro Ser Phe Gly Gly Cys Glu Ser Leu Val Asp Gln Pro Ala Ile Met
450                 455                 460

Ser Tyr Trp Asp Leu Pro Gln Glu Glu Arg Leu Lys Tyr Gly Ile Lys
465                 470                 475                 480

Asp Asn Leu Val Arg Phe Ser Phe Gly Val Glu Asp Phe Glu Asp Val
            485                 490                 495

Lys Ala Asp Ile Leu Gln Ala Leu Glu Ala Ile
            500                 505

<210> SEQ ID NO 8
<211> LENGTH: 531
<212> TYPE: PRT
<213> ORGANISM: Arabidopsis thaliana

<400> SEQUENCE: 8

Lys Ser Ser Arg Ile Leu Arg Phe Pro Pro Asn Phe Val Arg Gln Leu
1               5                   10                  15

Ser Ile Lys Ala Arg Arg Asn Cys Ser Asn Ile Ser Val Ala Gln Met
            20                  25                  30

Val Ala Gly Lys Trp Ser Asn Asn Pro Ser Ser Ala Leu Pro Ser Ala
        35                  40                  45

Ala Ala Ala Ala Thr Ser Ser Ala Ser Ala Val Ser Ser Ala Ala
    50                  55                  60

Ser Ala Ala Ala Ser Ser Ala Ala Ala Pro Val Ala Ala Ala
65                  70                  75                  80

Pro Pro Val Val Leu Lys Ser Val Asp Glu Val Val Ala Glu
                85                  90                  95

Glu Gly Ile Arg Glu Lys Ile Gly Ser Val Gln Leu Thr Asp Ser Lys
            100                 105                 110

His Ser Phe Leu Ser Ser Asp Gly Ser Leu Thr Val His Ala Gly Glu
        115                 120                 125

Arg Leu Gly Arg Gly Ile Val Thr Asp Ala Ile Thr Thr Pro Val Val
130                 135                 140

Asn Thr Ser Ala Tyr Phe Phe Lys Lys Thr Ala Glu Leu Ile Asp Phe
145                 150                 155                 160

Lys Glu Lys Arg Ser Val Ser Phe Glu Tyr Gly Arg Tyr Gly Asn Pro
                165                 170                 175

Thr Thr Val Val Leu Glu Asp Lys Ile Ser Ala Leu Glu Gly Ala Glu
            180                 185                 190

Ser Thr Leu Val Met Ala Ser Gly Met Cys Ala Ser Thr Val Met Leu
        195                 200                 205

Leu Ala Leu Val Pro Ala Gly Gly His Ile Val Thr Thr Asp Cys
210                 215                 220

Tyr Arg Lys Thr Arg Ile Phe Met Glu Asn Phe Leu Pro Lys Leu Gly
225                 230                 235                 240

Ile Thr Val Thr Val Ile Asp Pro Ala Asp Ile Ala Gly Leu Glu Ala
                245                 250                 255

Ala Val Asn Glu Phe Lys Val Ser Leu Phe Phe Thr Glu Ser Pro Thr
            260                 265                 270

Asn Pro Phe Leu Arg Cys Val Asp Ile Glu Leu Val Ser Lys Val Cys
        275                 280                 285

Arg Lys Arg Gly Thr Leu Val Cys Ile Asp Gly Thr Phe Ala Thr Pro

Leu Asn Gln Lys Ala Leu Ala Leu Gly Ala Asp Leu Val His Ser
305                 310                 315                 320

Ala Thr Lys Tyr Ile Gly Gly His Asn Asp Val Leu Ala Gly Cys Ile
                325                 330                 335

Cys Gly Ser Leu Lys Leu Val Ser Glu Ile Arg Asn Leu His His Val
            340                 345                 350

Leu Gly Gly Thr Leu Asn Pro Asn Ala Ala Tyr Leu Ile Ile Arg Gly
        355                 360                 365

Met Lys Thr Leu His Leu Arg Val Gln Gln Asn Ser Thr Ala Phe
    370                 375                 380

Arg Met Ala Glu Ile Leu Glu Ala His Pro Lys Val Ser His Val Tyr
385                 390                 395                 400

Tyr Pro Gly Leu Pro Ser His Pro Glu His Glu Leu Ala Lys Arg Gln
                405                 410                 415

Met Thr Gly Phe Gly Gly Val Val Ser Phe Glu Ile Asp Gly Asp Ile
            420                 425                 430

Glu Thr Thr Ile Lys Phe Val Asp Ser Leu Lys Ile Pro Tyr Ile Ala
        435                 440                 445

Pro Ser Phe Gly Gly Cys Glu Ser Ile Val Asp Gln Pro Ala Ile Met
    450                 455                 460

Ser Tyr Trp Asp Leu Pro Gln Glu Glu Arg Leu Lys Tyr Gly Ile Lys
465                 470                 475                 480

Asp Asn Leu Val Arg Phe Ser Phe Gly Val Glu Asp Phe Glu Asp Val
                485                 490                 495

Lys Ala Asp Ile Leu Gln Ala Leu Glu Ala Ile Trp Gly Ser Thr Ser
            500                 505                 510

Ser Arg Ala Ala Ala Ala Val Gly Glu Phe Leu Met Ile Tyr Asp
        515                 520                 525

Phe Tyr Tyr
    530

<210> SEQ ID NO 9
<211> LENGTH: 507
<212> TYPE: PRT
<213> ORGANISM: Arabidopsis thaliana

<400> SEQUENCE: 9

Met Ser Ser Arg Ile Leu Arg Phe Pro Leu Asn Phe Val Arg Gln Leu
1               5                   10                  15

Ser Ile Lys Ala Arg Arg Asn Cys Ser Asn Ile Ser Val Ala Gln Ile
            20                  25                  30

Val Ala Gly Lys Trp Ser Asn Asn Pro Ser Ser Ala Leu Pro Ser Ala
        35                  40                  45

Ala Ala Ala Ala Thr Ser Ser Ala Ser Val Ser Ser Ala Ala
    50                  55                  60

Ser Ala Ala Ala Ser Ser Ala Ala Ala Pro Val Ala Ala Ala
65                  70                  75                  80

Pro Pro Val Val Leu Lys Ser Val Asp Glu Val Val Ala Glu
                85                  90                  95

Glu Gly Ile Arg Glu Lys Ile Gly Ser Val Gln Leu Thr Asp Ser Lys
            100                 105                 110

His Ser Phe Leu Ser Ser Asp Gly Ser Leu Thr Val His Ala Gly Glu
        115                 120                 125

Arg Leu Gly Arg Gly Ile Val Thr Asp Ala Ile Thr Thr Pro Val Val
130                 135                 140

Asn Thr Ser Ala Tyr Phe Phe Lys Lys Thr Ala Glu Leu Ile Asp Phe
145                 150                 155                 160

Lys Glu Lys Arg Ser Val Ser Phe Glu Tyr Gly Arg Tyr Gly Asn Pro
                165                 170                 175

Thr Thr Val Val Leu Glu Asp Lys Ile Ser Ala Leu Glu Gly Ala Glu
                180                 185                 190

Ser Thr Leu Val Met Ala Ser Gly Met Cys Ala Ser Thr Val Met Leu
            195                 200                 205

Leu Ala Leu Val Pro Ala Gly Gly His Ile Val Thr Thr Thr Asp Cys
210                 215                 220

Tyr Arg Lys Thr Arg Ile Phe Leu Glu Asn Phe Leu Pro Lys Leu Gly
225                 230                 235                 240

Ile Thr Val Thr Ala Ile Asp Pro Ala Asp Ile Ala Gly Leu Glu Ala
                245                 250                 255

Ala Val Asp Glu Phe Lys Val Ser Leu Phe Phe Thr Glu Ser Pro Thr
                260                 265                 270

Asn Pro Phe Leu Arg Cys Val Asp Ile Glu Leu Val Ser Lys Ile Cys
            275                 280                 285

His Lys Arg Gly Thr Leu Val Cys Ile Asp Gly Thr Phe Ala Thr Pro
290                 295                 300

Leu Asn Gln Lys Ala Leu Ala Leu Gly Ala Asp Leu Val Val His Ser
305                 310                 315                 320

Ala Thr Lys Tyr Ile Gly Gly His Asn Asp Val Leu Ala Gly Cys Ile
                325                 330                 335

Cys Gly Ser Leu Lys Leu Val Ser Glu Ile Arg Asn Leu His His Val
            340                 345                 350

Leu Gly Gly Thr Leu Asn Pro Asn Ala Ala Tyr Leu Ile Ile Arg Gly
            355                 360                 365

Met Lys Thr Leu His Leu Arg Val Gln Gln Asn Ser Thr Ala Phe
370                 375                 380

Arg Met Ala Glu Ile Leu Glu Ala His Pro Lys Val Ser His Val Tyr
385                 390                 395                 400

Tyr Pro Gly Leu Pro Ser His Pro Glu His Glu Leu Ala Lys Arg Gln
                405                 410                 415

Met Thr Gly Phe Gly Gly Val Val Ser Phe Glu Ile Asp Gly Gly Ile
                420                 425                 430

Glu Thr Thr Thr Lys Phe Val Asp Ser Leu Lys Ile Pro Tyr Ile Ala
            435                 440                 445

Pro Ser Phe Gly Gly Cys Glu Ser Ile Val Asp Gln Pro Ala Ile Met
450                 455                 460

Ser Tyr Trp Asp Leu Pro Gln Glu Glu Arg Leu Lys Tyr Gly Ile Lys
465                 470                 475                 480

Asp Asn Leu Val Arg Phe Ser Phe Gly Val Glu Asp Phe Glu Asp Val
                485                 490                 495

Lys Ala Asp Ile Leu Gln Ala Leu Glu Ala Ile
                500                 505

<210> SEQ ID NO 10
<211> LENGTH: 507
<212> TYPE: PRT
<213> ORGANISM: Arabidopsis thaliana

<400> SEQUENCE: 10

-continued

```
Met Ser Ser Arg Ile Leu Arg Phe Pro Pro Asp Phe Val Arg Leu
1               5                   10                  15

Ser Ile Lys Ala Arg Arg Asn Cys Ser Asn Ile Ser Val Thr Gln Ile
            20                  25                  30

Val Ala Gly Lys Trp Ser Asn Asn Pro Ser Ser Ala Ser Pro Thr Ala
        35                  40                  45

Ala Ala Ala Ala Ala Thr Ser Ser Ala Ser Ala Val Ser Ser Ala Ala
50                      55                  60

Ser Ala Ala Thr Ala Ser Ser Ala Ala Ala Pro Val Ala Ala Ala
65              70                  75                  80

Pro Pro Val Val Leu Lys Ser Val Asp Glu Glu Val Val Ala Glu
                85                  90                  95

Glu Gly Ile Arg Glu Lys Ile Gly Ser Val Gln Leu Thr Asp Ser Lys
            100                 105                 110

His Ser Phe Leu Ser Ser Asp Gly Ser Leu Thr Val His Ala Gly Glu
        115                 120                 125

Arg Leu Gly Arg Gly Ile Val Thr Asp Ala Ile Thr Thr Pro Val Val
130                 135                 140

Asn Thr Ser Ala Tyr Phe Phe Lys Lys Thr Ala Glu Leu Ile Asp Phe
145                 150                 155                 160

Lys Glu Lys Arg Ser Val Ser Phe Glu Tyr Gly Arg Tyr Gly Asn Pro
                165                 170                 175

Thr Ile Val Val Leu Glu Asp Lys Ile Ser Ala Leu Glu Gly Ala Glu
            180                 185                 190

Ser Thr Leu Val Met Ala Ser Gly Met Cys Ala Ser Thr Val Met Leu
        195                 200                 205

Leu Ala Leu Val Pro Ala Gly Gly His Ile Val Thr Thr Thr Asp Cys
210                 215                 220

Tyr Arg Lys Thr Arg Ile Phe Met Glu Asn Phe Leu Pro Lys Leu Gly
225                 230                 235                 240

Ile Thr Val Thr Val Ile Asp Pro Ala Asp Ile Ala Gly Leu Glu Ala
            245                 250                 255

Ala Val Asn Glu Phe Lys Val Ser Leu Phe Phe Thr Glu Ser Pro Thr
        260                 265                 270

Asn Pro Phe Leu Arg Cys Val Asp Ile Glu Leu Val Ser Lys Ile Cys
        275                 280                 285

His Lys Arg Gly Thr Leu Val Cys Ile Asp Gly Thr Phe Ala Thr Pro
        290                 295                 300

Leu Asn Gln Lys Ala Leu Ala Leu Gly Ala Asp Leu Val His Ser
305                 310                 315                 320

Ala Thr Lys Tyr Ile Gly Gly His Asn Asp Val Leu Ala Gly Cys Ile
            325                 330                 335

Cys Gly Ser Leu Lys Leu Val Ser Glu Ile Arg Asn Leu His His Val
        340                 345                 350

Leu Gly Gly Thr Leu Asn Pro Asn Ala Ala Tyr Leu Ile Ile Arg Gly
        355                 360                 365

Met Lys Ala Leu His Leu Arg Val Gln Gln Asn Ser Thr Ala Phe
370                 375                 380

Arg Met Ala Glu Ile Leu Glu Ala His Pro Lys Val Ser His Val Tyr
385                 390                 395                 400

Tyr Pro Gly Leu Pro Ser His Pro Glu His Glu Leu Ala Lys Arg Gln
            405                 410                 415
```

```
Met Thr Gly Phe Gly Gly Val Val Ser Phe Glu Ile Asp Gly Asp Ile
            420                 425                 430

Glu Thr Thr Ile Lys Phe Val Asp Ser Leu Lys Ile Pro Tyr Ile Ala
            435                 440                 445

Pro Ser Phe Gly Gly Cys Glu Ser Ile Val Asn Gln Pro Ala Ile Met
            450                 455                 460

Ser Tyr Trp Asp Leu Pro Gln Glu Glu Arg Leu Lys Tyr Gly Ile Lys
465                 470                 475                 480

Asp Asn Leu Val Arg Phe Ser Phe Gly Val Glu Asp Phe Glu Asp Val
                485                 490                 495

Lys Ala Asp Ile Leu Gln Ala Leu Glu Ala Ile
            500                 505

<210> SEQ ID NO 11
<211> LENGTH: 476
<212> TYPE: PRT
<213> ORGANISM: Arabidopsis thaliana

<400> SEQUENCE: 11

Met Val Ala Gly Lys Trp Ser Asn Asn Pro Ser Ser Ala Leu Pro Ser
1               5                   10                  15

Ala Ala Ala Ala Ala Thr Ser Ser Ala Ser Ala Val Ser Ser Ala
            20                  25                  30

Ala Ser Ala Ala Ala Ser Ser Ala Ala Ala Ala Pro Val Ala Ala
            35                  40                  45

Ala Pro Pro Val Val Leu Lys Ser Val Asp Glu Val Val Val Ala
        50                  55                  60

Glu Glu Gly Ile Arg Glu Lys Ile Gly Ser Val Gln Leu Thr Asp Ser
65                  70                  75                  80

Lys His Ser Phe Leu Ser Ser Asp Gly Ser Leu Thr Val His Ala Gly
                85                  90                  95

Glu Arg Leu Gly Arg Gly Ile Val Thr Asp Ala Ile Thr Thr Pro Val
            100                 105                 110

Val Asn Thr Ser Ala Tyr Phe Phe Lys Lys Thr Ala Glu Leu Ile Asp
            115                 120                 125

Phe Lys Glu Lys Arg Ser Val Ser Phe Glu Tyr Gly Arg Tyr Gly Asn
130                 135                 140

Pro Thr Thr Val Val Leu Glu Asp Lys Ile Ser Ala Leu Glu Gly Ala
145                 150                 155                 160

Glu Ser Thr Leu Val Met Ala Ser Gly Met Cys Ala Ser Thr Val Met
                165                 170                 175

Leu Leu Ala Leu Val Pro Ala Gly Gly His Ile Val Thr Thr Thr Asp
            180                 185                 190

Cys Tyr Arg Lys Thr Arg Ile Phe Met Glu Asn Phe Leu Pro Lys Leu
            195                 200                 205

Gly Ile Thr Val Thr Val Ile Asp Pro Ala Asp Ile Ala Gly Leu Glu
            210                 215                 220

Ala Ala Val Asn Glu Phe Lys Val Ser Leu Phe Phe Thr Glu Ser Pro
225                 230                 235                 240

Thr Asn Pro Phe Leu Arg Cys Val Asp Ile Glu Leu Val Ser Lys Ile
                245                 250                 255

Cys His Lys Arg Gly Thr Leu Val Cys Ile Asp Gly Thr Phe Ala Thr
            260                 265                 270

Pro Leu Asn Gln Lys Ala Leu Ala Leu Gly Ala Asp Leu Val Val His
            275                 280                 285
```

-continued

```
Ser Ala Thr Lys Tyr Ile Gly Gly His Asn Asp Val Leu Ala Gly Cys
        290                 295                 300

Ile Cys Gly Ser Leu Lys Leu Val Ser Glu Ile Arg Asn Leu His His
305                 310                 315                 320

Val Leu Gly Gly Thr Leu Asn Pro Asn Ala Ala Tyr Leu Ile Ile Arg
                325                 330                 335

Gly Met Lys Thr Leu His Leu Arg Val Gln Gln Asn Ser Thr Ala
                340                 345                 350

Phe Arg Met Ala Glu Ile Leu Glu Ala His Pro Lys Val Ser His Val
        355                 360                 365

Tyr Tyr Pro Gly Leu Pro Ser His Pro Glu His Glu Leu Ala Lys Arg
    370                 375                 380

Gln Met Thr Gly Phe Gly Gly Val Val Ser Phe Glu Ile Asp Gly Asp
385                 390                 395                 400

Ile Glu Thr Thr Ile Lys Phe Val Asp Ser Leu Lys Ile Pro Tyr Ile
                405                 410                 415

Ala Pro Ser Phe Gly Gly Cys Glu Ser Ile Val Asp Gln Pro Ala Ile
                420                 425                 430

Met Ser Tyr Trp Asp Leu Pro Gln Glu Glu Arg Leu Lys Tyr Gly Ile
        435                 440                 445

Lys Asp Asn Leu Val Arg Phe Ser Phe Gly Val Glu Asp Phe Glu Asp
    450                 455                 460

Val Lys Ala Asp Ile Leu Gln Ala Leu Glu Ala Ile
465                 470                 475

<210> SEQ ID NO 12
<211> LENGTH: 476
<212> TYPE: PRT
<213> ORGANISM: Arabidopsis thaliana

<400> SEQUENCE: 12

Met Val Ala Gly Lys Trp Ser Asn Asn Pro Ser Ser Ala Leu Pro Ser
1               5                   10                  15

Ala Ala Ala Ala Ala Thr Ser Ser Ala Ser Ala Asp Ser Ser Ala
            20                  25                  30

Ala Ser Ala Ala Ala Ser Ser Ala Ala Ala Pro Val Ala Ala
        35                  40                  45

Ala Pro Pro Val Val Leu Lys Ser Val Asp Glu Val Val Val Ala
    50                  55                  60

Glu Glu Gly Ile Arg Glu Lys Ile Gly Ser Val Gln Leu Thr Asp Ser
65                  70                  75                  80

Lys His Ser Phe Leu Ser Ser Asp Gly Ser Leu Thr Val His Ala Gly
                85                  90                  95

Glu Arg Leu Gly Arg Gly Ile Val Thr Asp Ala Ile Thr Thr Pro Val
            100                 105                 110

Val Asn Thr Ser Ala Tyr Phe Phe Lys Lys Thr Ala Glu Leu Ile Asp
        115                 120                 125

Phe Lys Glu Lys Arg Ser Val Ser Phe Glu Tyr Gly Arg Tyr Gly Asn
    130                 135                 140

Pro Thr Thr Val Val Leu Glu Asp Lys Ile Ser Ala Leu Glu Gly Ala
145                 150                 155                 160

Glu Ser Thr Leu Val Met Ala Ser Gly Met Cys Ala Ser Thr Val Met
                165                 170                 175

Leu Leu Ala Leu Val Pro Ala Gly Gly His Ile Val Thr Thr Thr Asp
```

```
                180                 185                 190
Cys Tyr Arg Lys Thr Arg Ile Phe Met Glu Asn Phe Leu Pro Lys Leu
            195                 200                 205

Gly Ile Thr Val Thr Val Ile Asp Pro Ala Asp Ile Ala Gly Leu Glu
        210                 215                 220

Ala Ala Val Asn Glu Phe Lys Val Ser Leu Phe Phe Thr Glu Ser Pro
225                 230                 235                 240

Thr Asn Pro Phe Leu Arg Cys Val Asp Ile Glu Leu Val Ser Lys Ile
            245                 250                 255

Cys His Lys Arg Gly Thr Leu Val Cys Ile Asp Gly Thr Phe Ala Thr
        260                 265                 270

Pro Leu Asn Gln Lys Ala Leu Ala Leu Gly Ala Asp Leu Val Val His
            275                 280                 285

Ser Ala Thr Lys Phe Ile Gly Gly His Asn Asp Val Leu Ala Gly Cys
        290                 295                 300

Ile Cys Gly Ser Leu Lys Leu Val Ser Glu Ile Arg Asn Leu His His
305                 310                 315                 320

Val Leu Gly Gly Pro Leu Asn Pro Asn Ala Ala Tyr Leu Ile Ile Arg
            325                 330                 335

Gly Met Lys Thr Leu His Leu Arg Val Gln Gln Asn Ser Thr Ala
        340                 345                 350

Phe Arg Met Ala Glu Ile Leu Glu Ala His Pro Lys Val Ser His Val
        355                 360                 365

Tyr Tyr Pro Gly Leu Pro Ser His Pro Glu His Glu Leu Ala Lys Arg
        370                 375                 380

Gln Met Thr Gly Phe Gly Gly Val Val Ser Phe Glu Ile Asp Gly Asp
385                 390                 395                 400

Ile Glu Thr Thr Ile Lys Phe Val Asp Ser Leu Lys Ile Pro Tyr Ile
            405                 410                 415

Ala Pro Ser Phe Gly Gly Cys Glu Ser Leu Val Asp Gln Pro Ala Ile
        420                 425                 430

Met Ser Tyr Trp Asp Leu Pro Gln Glu Glu Arg Leu Lys Tyr Gly Ile
        435                 440                 445

Lys Asp Asn Leu Val Arg Phe Ser Phe Gly Val Glu Asp Phe Glu Asp
450                 455                 460

Val Lys Ala Asp Ile Leu Gln Ala Leu Glu Ala Ile
465                 470                 475

<210> SEQ ID NO 13
<211> LENGTH: 476
<212> TYPE: PRT
<213> ORGANISM: Arabidopsis thaliana

<400> SEQUENCE: 13

Met Val Ala Gly Lys Trp Ser Asn Asn Pro Ser Ser Ala Leu Pro Ser
1               5                   10                  15

Ala Ala Ala Ala Ala Thr Ser Ala Ser Ala Val Ser Ser Ala
            20                  25                  30

Ala Ser Ala Ala Ala Ser Ser Ala Ala Ala Pro Val Ala Ala
        35                  40                  45

Ala Pro Pro Val Val Leu Lys Ser Val Asp Glu Val Val Ala
    50                  55                  60

Glu Glu Gly Ile Arg Glu Lys Ile Gly Ser Val Gln Leu Thr Asp Ser
65                  70                  75                  80
```

```
Lys His Ser Phe Leu Ser Ser Asp Gly Ser Leu Thr Val His Ala Gly
                85                  90                  95
Glu Arg Leu Gly Arg Gly Ile Val Thr Asp Ala Ile Thr Thr Pro Val
            100                 105                 110
Val Asn Thr Ser Ala Tyr Phe Lys Lys Thr Ala Glu Leu Ile Asp
        115                 120                 125
Phe Lys Glu Lys Arg Ser Val Ser Phe Glu Tyr Gly Arg Tyr Gly Asn
130                 135                 140
Pro Thr Thr Val Val Leu Glu Asp Lys Ile Ser Ala Leu Glu Gly Ala
145                 150                 155                 160
Glu Ser Thr Leu Val Met Ala Ser Gly Met Cys Ala Ser Thr Val Met
                165                 170                 175
Leu Leu Ala Leu Val Pro Ala Gly Gly His Ile Val Thr Thr Thr Asp
            180                 185                 190
Cys Tyr Arg Lys Thr Arg Ile Phe Met Glu Asn Phe Leu Pro Lys Leu
        195                 200                 205
Gly Ile Thr Val Thr Val Ile Asp Pro Ala Asp Ile Ala Gly Leu Glu
    210                 215                 220
Ala Ala Val Asn Glu Phe Lys Val Ser Leu Phe Phe Thr Glu Ser Pro
225                 230                 235                 240
Thr Asn Pro Phe Leu Arg Cys Val Asp Ile Glu Leu Val Ser Lys Val
                245                 250                 255
Cys Arg Lys Arg Gly Thr Leu Val Cys Ile Asp Gly Thr Phe Ala Thr
            260                 265                 270
Pro Leu Asn Gln Lys Ala Leu Ala Leu Gly Ala Asp Leu Val Val His
        275                 280                 285
Ser Ala Thr Lys Tyr Ile Gly Gly His Asn Asp Val Leu Ala Gly Cys
    290                 295                 300
Ile Cys Gly Ser Leu Lys Leu Val Ser Glu Ile Arg Asn Leu His His
305                 310                 315                 320
Val Leu Gly Gly Thr Leu Asn Pro Asn Ala Ala Tyr Leu Ile Ile Arg
                325                 330                 335
Gly Met Lys Thr Leu His Leu Arg Val Gln Gln Gln Asn Ser Thr Ala
            340                 345                 350
Phe Arg Met Ala Glu Ile Leu Glu Ala His Pro Lys Val Ser His Val
        355                 360                 365
Tyr Tyr Pro Gly Leu Pro Ser His Pro Glu His Glu Leu Ala Lys Arg
    370                 375                 380
Gln Met Thr Gly Phe Gly Gly Val Val Ser Phe Glu Ile Asp Gly Asp
385                 390                 395                 400
Ile Glu Thr Thr Ile Lys Phe Val Asp Ser Leu Lys Ile Pro Tyr Ile
                405                 410                 415
Ala Pro Ser Phe Gly Gly Cys Glu Ser Ile Val Asp Gln Pro Ala Ile
            420                 425                 430
Met Ser Tyr Trp Asp Leu Pro Gln Glu Glu Arg Leu Lys Tyr Gly Ile
        435                 440                 445
Lys Asp Asn Leu Val Arg Phe Ser Phe Gly Val Glu Asp Phe Glu Asp
    450                 455                 460
Val Lys Ala Asp Ile Leu Gln Ala Leu Glu Ala Ile
465                 470                 475

<210> SEQ ID NO 14
<211> LENGTH: 476
<212> TYPE: PRT
```

<213> ORGANISM: Arabidopsis thaliana

<400> SEQUENCE: 14

Met Val Ala Gly Lys Trp Ser Asn Asn Pro Ser Ser Ala Leu Pro Ser
1               5                   10                  15

Ala Ala Ala Ala Ala Thr Ser Ser Ala Ser Ala Val Ser Ser Ala
            20                  25                  30

Ala Ser Ala Ala Ala Ser Ser Ala Ala Ala Pro Val Ala Ala
        35                  40                  45

Ala Pro Pro Val Val Leu Lys Ser Val Asp Glu Val Val Ala
50                  55                  60

Glu Glu Gly Ile Arg Glu Lys Ile Gly Ser Val Gln Leu Thr Asp Ser
65                  70                  75                  80

Lys His Ser Phe Leu Ser Ser Asp Gly Ser Leu Thr Val His Ala Gly
                85                  90                  95

Glu Arg Leu Gly Arg Gly Ile Val Thr Asp Ala Ile Thr Thr Pro Val
            100                 105                 110

Val Asn Thr Ser Ala Tyr Phe Phe Lys Lys Thr Ala Glu Leu Ile Asp
            115                 120                 125

Phe Lys Glu Lys Arg Ser Val Ser Phe Glu Tyr Gly Arg Tyr Gly Asn
130                 135                 140

Pro Thr Thr Val Val Leu Glu Asp Lys Ile Ser Ala Leu Glu Gly Ala
145                 150                 155                 160

Glu Ser Thr Leu Val Met Ala Ser Gly Met Cys Ala Ser Thr Val Met
                165                 170                 175

Leu Leu Ala Leu Val Pro Ala Gly Gly His Ile Val Thr Thr Thr Asp
            180                 185                 190

Cys Tyr Arg Lys Thr Arg Ile Phe Leu Glu Asn Phe Leu Pro Lys Leu
        195                 200                 205

Gly Ile Thr Val Thr Ala Ile Asp Pro Ala Asp Ile Ala Gly Leu Glu
    210                 215                 220

Ala Ala Val Asp Glu Phe Lys Val Ser Leu Phe Phe Thr Glu Ser Pro
225                 230                 235                 240

Thr Asn Pro Phe Leu Arg Cys Val Asp Ile Glu Leu Val Ser Lys Ile
                245                 250                 255

Cys His Lys Arg Gly Thr Leu Val Cys Ile Asp Gly Thr Phe Ala Thr
            260                 265                 270

Pro Leu Asn Gln Lys Ala Leu Ala Leu Gly Ala Asp Leu Val Val His
        275                 280                 285

Ser Ala Thr Lys Tyr Ile Gly Gly His Asn Asp Val Leu Ala Gly Cys
    290                 295                 300

Ile Cys Gly Ser Leu Lys Leu Val Ser Glu Ile Arg Asn Leu His His
305                 310                 315                 320

Val Leu Gly Gly Thr Leu Asn Pro Asn Ala Ala Tyr Leu Ile Ile Arg
                325                 330                 335

Gly Met Lys Thr Leu His Leu Arg Val Gln Gln Asn Ser Thr Ala
            340                 345                 350

Phe Arg Met Ala Glu Ile Leu Glu Ala His Pro Lys Val Ser His Val
        355                 360                 365

Tyr Tyr Pro Gly Leu Pro Ser His Pro Glu His Glu Leu Ala Lys Arg
    370                 375                 380

Gln Met Thr Gly Phe Gly Gly Val Val Ser Phe Glu Ile Asp Gly Gly
385                 390                 395                 400

```
Ile Glu Thr Thr Thr Lys Phe Val Asp Ser Leu Lys Ile Pro Tyr Ile
                405                 410                 415

Ala Pro Ser Phe Gly Gly Cys Glu Ser Ile Val Asp Gln Pro Ala Ile
            420                 425                 430

Met Ser Tyr Trp Asp Leu Pro Gln Glu Glu Arg Leu Lys Tyr Gly Ile
        435                 440                 445

Lys Asp Asn Leu Val Arg Phe Ser Phe Gly Val Glu Asp Phe Glu Asp
    450                 455                 460

Val Lys Ala Asp Ile Leu Gln Ala Leu Glu Ala Ile
465                 470                 475

<210> SEQ ID NO 15
<211> LENGTH: 476
<212> TYPE: PRT
<213> ORGANISM: Arabidopsis thaliana

<400> SEQUENCE: 15

Met Val Ala Gly Lys Trp Ser Asn Asn Pro Ser Ser Ala Ser Pro Thr
1               5                   10                  15

Ala Ala Ala Ala Ala Ala Thr Ser Ser Ala Ser Ala Val Ser Ser Ala
            20                  25                  30

Ala Ser Ala Ala Thr Ala Ser Ser Ala Ala Ala Ala Pro Val Ala Ala
        35                  40                  45

Ala Pro Pro Val Val Leu Lys Ser Val Asp Glu Glu Val Val Val Ala
    50                  55                  60

Glu Glu Gly Ile Arg Glu Lys Ile Gly Ser Val Gln Leu Thr Asp Ser
65                  70                  75                  80

Lys His Ser Phe Leu Ser Ser Asp Gly Ser Leu Thr Val His Ala Gly
                85                  90                  95

Glu Arg Leu Gly Arg Gly Ile Val Thr Asp Ala Ile Thr Thr Pro Val
            100                 105                 110

Val Asn Thr Ser Ala Tyr Phe Phe Lys Lys Thr Ala Glu Leu Ile Asp
        115                 120                 125

Phe Lys Glu Lys Arg Ser Val Ser Phe Glu Tyr Gly Arg Tyr Gly Asn
    130                 135                 140

Pro Thr Ile Val Val Leu Glu Asp Lys Ile Ser Ala Leu Glu Gly Ala
145                 150                 155                 160

Glu Ser Thr Leu Val Met Ala Ser Gly Met Cys Ala Ser Thr Val Met
                165                 170                 175

Leu Leu Ala Leu Val Pro Ala Gly Gly His Ile Val Thr Thr Thr Asp
            180                 185                 190

Cys Tyr Arg Lys Thr Arg Ile Phe Met Glu Asn Phe Leu Pro Lys Leu
        195                 200                 205

Gly Ile Thr Val Thr Val Ile Asp Pro Ala Asp Ile Ala Gly Leu Glu
    210                 215                 220

Ala Ala Val Asn Glu Phe Lys Val Ser Leu Phe Phe Thr Glu Ser Pro
225                 230                 235                 240

Thr Asn Pro Phe Leu Arg Cys Val Asp Ile Glu Leu Val Ser Lys Ile
                245                 250                 255

Cys His Lys Arg Gly Thr Leu Val Cys Ile Asp Gly Thr Phe Ala Thr
            260                 265                 270

Pro Leu Asn Gln Lys Ala Leu Ala Leu Gly Ala Asp Leu Val Val His
        275                 280                 285

Ser Ala Thr Lys Tyr Ile Gly Gly His Asn Asp Val Leu Ala Gly Cys
    290                 295                 300
```

```
Ile Cys Gly Ser Leu Lys Leu Val Ser Glu Ile Arg Asn Leu His His
305                 310                 315                 320

Val Leu Gly Gly Thr Leu Asn Pro Asn Ala Ala Tyr Leu Ile Ile Arg
                325                 330                 335

Gly Met Lys Ala Leu His Leu Arg Val Gln Gln Gln Asn Ser Thr Ala
            340                 345                 350

Phe Arg Met Ala Glu Ile Leu Glu Ala His Pro Lys Val Ser His Val
        355                 360                 365

Tyr Tyr Pro Gly Leu Pro Ser His Pro Glu His Glu Leu Ala Lys Arg
    370                 375                 380

Gln Met Thr Gly Phe Gly Gly Val Val Ser Phe Glu Ile Asp Gly Asp
385                 390                 395                 400

Ile Glu Thr Thr Ile Lys Phe Val Asp Ser Leu Lys Ile Pro Tyr Ile
                405                 410                 415

Ala Pro Ser Phe Gly Gly Cys Glu Ser Ile Val Asn Gln Pro Ala Ile
            420                 425                 430

Met Ser Tyr Trp Asp Leu Pro Gln Glu Glu Arg Leu Lys Tyr Gly Ile
        435                 440                 445

Lys Asp Asn Leu Val Arg Phe Ser Phe Gly Val Glu Asp Phe Glu Asp
    450                 455                 460

Val Lys Ala Asp Ile Leu Gln Ala Leu Glu Ala Ile
465                 470                 475

<210> SEQ ID NO 16
<211> LENGTH: 404
<212> TYPE: PRT
<213> ORGANISM: Arabidopsis thaliana

<400> SEQUENCE: 16

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
                20                  25                  30

Thr Asp Ala Ile Thr Thr Pro Val Val Asn Thr Ser Ala Tyr Phe Phe
            35                  40                  45

Lys Lys Thr Ala Glu Leu Ile Asp Phe Lys Glu Lys Arg Ser Val Ser
        50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
    130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Phe Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
```

```
            195                 200                 205
Leu Gly Ala Asp Leu Val Val His Ser Ala Thr Lys Tyr Ile Gly Gly
210                 215                 220

His Asn Asp Val Leu Ala Gly Cys Ile Cys Gly Ser Leu Lys Leu Val
225                 230                 235                 240

Ser Glu Ile Arg Asn Leu His Val Leu Gly Gly Thr Leu Asn Pro
                245                 250                 255

Asn Ala Ala Tyr Leu Ile Ile Arg Gly Met Lys Thr Leu His Leu Arg
                260                 265                 270

Val Gln Gln Gln Asn Ser Thr Ala Phe Arg Met Ala Glu Ile Leu Glu
            275                 280                 285

Ala His Pro Lys Val Ser His Val Tyr Tyr Pro Gly Leu Pro Ser His
290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
                340                 345                 350

Ser Ile Val Asp Gln Pro Ala Ile Met Ser Tyr Trp Asp Leu Pro Gln
            355                 360                 365

Glu Glu Arg Leu Lys Tyr Gly Ile Lys Asp Asn Leu Val Arg Phe Ser
370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 17
<211> LENGTH: 404
<212> TYPE: PRT
<213> ORGANISM: Arabidopsis thaliana

<400> SEQUENCE: 17

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
                20                  25                  30

Thr Asp Ala Ile Thr Thr Pro Val Asn Thr Ser Ala Tyr Phe Phe
                35                  40                  45

Lys Lys Thr Ala Glu Leu Ile Asp Phe Lys Lys Arg Ser Val Ser
50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
                100                 105                 110

Gly His Ile Val Thr Thr Thr Asp Cys Tyr Arg Lys Thr Arg Ile Phe
                115                 120                 125

Leu Glu Asn Phe Leu Pro Lys Leu Gly Ile Thr Val Thr Ala Ile Asp
                130                 135                 140

Pro Ala Asp Ile Ala Gly Leu Glu Ala Ala Val Asp Glu Phe Lys Val
145                 150                 155                 160

Ser Leu Phe Phe Thr Glu Ser Pro Thr Asn Pro Phe Leu Arg Cys Val
```

```
                165                 170                 175
Asp Ile Glu Leu Val Ser Lys Ile Cys His Lys Arg Gly Thr Leu Val
            180                 185                 190
Cys Ile Asp Gly Thr Phe Ala Thr Pro Leu Asn Gln Lys Ala Leu Ala
        195                 200                 205
Leu Gly Ala Asp Leu Val Val His Ser Ala Thr Lys Tyr Ile Gly Gly
    210                 215                 220
His Asn Asp Val Leu Ala Gly Cys Ile Cys Gly Ser Leu Lys Leu Val
225                 230                 235                 240
Ser Glu Ile Arg Asn Leu His His Val Leu Gly Gly Thr Leu Asn Pro
                245                 250                 255
Asn Ala Ala Tyr Leu Ile Ile Arg Gly Met Lys Thr Leu His Leu Arg
            260                 265                 270
Val Gln Gln Asn Ser Thr Ala Phe Arg Met Ala Glu Ile Leu Glu
        275                 280                 285
Ala His Pro Lys Val Ser His Val Tyr Tyr Pro Gly Leu Pro Ser His
    290                 295                 300
Pro Glu His Glu Leu Ala Lys Arg Gln Met Thr Gly Phe Gly Gly Val
305                 310                 315                 320
Val Ser Phe Glu Ile Asp Gly Gly Ile Glu Thr Thr Lys Phe Val
                325                 330                 335
Asp Ser Leu Lys Ile Pro Tyr Ile Ala Pro Ser Phe Gly Gly Cys Glu
            340                 345                 350
Ser Ile Val Asp Gln Pro Ala Ile Met Ser Tyr Trp Asp Leu Pro Gln
        355                 360                 365
Glu Arg Leu Lys Tyr Gly Ile Lys Asp Asn Leu Val Arg Phe Ser
    370                 375                 380
Phe Gly Val Glu Asp Phe Glu Asp Val Lys Ala Asp Ile Leu Gln Ala
385                 390                 395                 400
Leu Glu Ala Ile

<210> SEQ ID NO 18
<211> LENGTH: 404
<212> TYPE: PRT
<213> ORGANISM: Arabidopsis thaliana

<400> SEQUENCE: 18

Met Ser Val Gln Leu Thr Asp Ser Lys His Ser Phe Leu Ser Ser Asp
1               5                   10                  15
Gly Ser Leu Thr Val His Ala Gly Glu Arg Leu Gly Arg Gly Ile Val
            20                  25                  30
Thr Asp Ala Ile Thr Thr Pro Val Val Asn Thr Ser Ala Tyr Phe Phe
        35                  40                  45
Lys Lys Thr Ala Glu Leu Ile Asp Phe Lys Glu Lys Arg Ser Val Ser
    50                  55                  60
Phe Glu Tyr Gly Arg Tyr Gly Asn Pro Thr Ile Val Val Leu Glu Asp
65                  70                  75                  80
Lys Ile Ser Ala Leu Glu Gly Ala Glu Ser Thr Leu Val Met Ala Ser
                85                  90                  95
Gly Met Cys Ala Ser Thr Val Met Leu Ala Leu Val Pro Ala Gly
            100                 105                 110
Gly His Ile Val Thr Thr Thr Asp Cys Tyr Arg Lys Thr Arg Ile Phe
        115                 120                 125
Met Glu Asn Phe Leu Pro Lys Leu Gly Ile Thr Val Thr Val Ile Asp
```

```
            130                 135                 140
Pro Ala Asp Ile Ala Gly Leu Glu Ala Val Asn Glu Phe Lys Val
145                 150                 155                 160

Ser Leu Phe Phe Thr Glu Ser Pro Thr Asn Pro Phe Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Ala Leu His Leu Arg
            260                 265                 270

Val Gln Gln Gln Asn Ser Thr Ala Phe Arg Met Ala Glu Ile Leu Glu
        275                 280                 285

Ala His Pro Lys Val Ser His Val Tyr Tyr Pro Gly Leu Pro Ser His
290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
            340                 345                 350

Ser Ile Val Asn Gln Pro Ala Ile Met Ser Tyr Trp Asp Leu Pro Gln
        355                 360                 365

Glu Glu Arg Leu Lys Tyr Gly Ile Lys Asp Asn Leu Val Arg Phe Ser
370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 19
<211> LENGTH: 404
<212> TYPE: PRT
<213> ORGANISM: Arabidopsis thaliana

<400> SEQUENCE: 19

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Val Asn Thr Ser Ala Tyr Leu Phe
        35                  40                  45

Lys Lys Thr Ala Glu Leu Ile Asp Phe Lys Glu Lys Arg Ser Val Ser
    50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
```

```
            100                 105                 110
Gly His Ile Val Thr Thr Thr Asp Cys Tyr Arg Lys Thr Arg Ile Phe
            115                 120                 125

Met Glu Asn Phe Leu Pro Lys Leu Gly Ile Thr Val Thr Val Ile Asp
    130                 135                 140

Pro Ala Asp Ile Ala Gly Leu Glu Ala Thr Val Ser Glu Ser Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys Tyr Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
    210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
            260                 265                 270

Val Gln Gln Gln Asn Ser Thr Ala Phe Arg Met Ala Glu Ile Leu Glu
        275                 280                 285

Ala His Pro Lys Val Ser His Val Tyr Tyr Pro Gly Leu Pro Ser His
    290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
            340                 345                 350

Ser Ile Val Asp Gln Pro Ala Ile Met Ser Tyr Trp Asp Leu Pro Gln
        355                 360                 365

Glu Glu Arg Leu Lys Tyr Gly Ile Lys Asp Asn Leu Val Arg Phe Ser
    370                 375                 380

Phe Gly Val Glu Asp Phe Glu Asp Val Lys Ala Asp Ile Leu Gln Ala
385                 390                 395                 400

Leu Glu Gly Ile

<210> SEQ ID NO 20
<211> LENGTH: 404
<212> TYPE: PRT
<213> ORGANISM: Arabidopsis thaliana

<400> SEQUENCE: 20

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Asn Thr Ser Ala Tyr Phe Phe
            35                  40                  45

Lys Lys Thr Ala Glu Leu Ile Asp Phe Lys Glu Lys Arg Ser Val Ser
        50                  55                  60

Phe Glu Tyr Gly Arg Tyr Gly Asn Pro Thr Thr Val Val Leu Glu Asp
```

```
                65                  70                  75                  80
        Lys Val Ser Ala Leu Glu Gly Ala Glu Ser Thr Leu Val Met Ala Ser
                        85                  90                  95

Gly Met Cys Ala Ser Thr Val Met Leu Leu Ala Leu Val Pro Ala Gly
                        100                 105                 110

Gly His Ile Val Thr Thr Thr Asp Cys Tyr Arg Lys Thr Arg Ile Phe
                        115                 120                 125

Met Glu Asn Phe Leu Pro Lys Leu Gly Ile Thr Val Thr Val Ile Asp
                        130                 135                 140

Pro Ala Asp Ile Ala Gly Leu Glu Ala Ala Val Asn Glu Phe Lys Val
        145                 150                 155                 160

Ser Leu Phe Phe Thr Glu Ser Pro Thr Asn Pro Phe Leu Arg Cys Val
                        165                 170                 175

Asp Ile Glu Leu Val Ser Lys Ile Cys His Lys Arg Gly Thr Leu Val
                        180                 185                 190

Cys Ile Asp Gly Thr Phe Ala Thr Pro Leu Asn Gln Lys Ala Leu Ala
                        195                 200                 205

Leu Gly Ala Asp Leu Val Val His Ser Ala Thr Lys Tyr Ile Gly Gly
                        210                 215                 220

His Asn Asp Val Leu Ala Gly Cys Ile Cys Gly Ser Leu Lys Leu Val
        225                 230                 235                 240

Ser Glu Ile Arg Asn Leu His His Val Leu Gly Gly Thr Leu Asn Pro
                        245                 250                 255

Asn Ala Ala Tyr Leu Ile Ile Arg Gly Met Lys Thr Leu His Leu Arg
                        260                 265                 270

Val Gln Gln Gln Asn Ser Thr Ala Phe Arg Met Ala Glu Ile Leu Glu
                        275                 280                 285

Ala His Pro Lys Val Ser His Val Tyr Tyr Pro Gly Leu Ser Ser His
                        290                 295                 300

Pro Glu His Glu Leu Ala Lys Arg Gln Met Thr Gly Phe Gly Gly Val
        305                 310                 315                 320

Val Ser Phe Glu Ile Asp Gly Asp Ile Glu Thr Thr Ile Lys Phe Val
                        325                 330                 335

Asp Ser Leu Lys Ile Pro Tyr Ile Ala Pro Ser Phe Gly Gly Cys Glu
                        340                 345                 350

Ser Ile Val Asp Gln Pro Ala Ile Met Ser Tyr Trp Asp Leu Pro Gln
                        355                 360                 365

Glu Glu Arg Leu Lys Tyr Gly Ile Lys Asp Asn Leu Val Arg Phe Ser
                        370                 375                 380

Phe Gly Val Glu Asp Phe Glu Asp Val Lys Ala Asp Ile Leu Gln Ala
        385                 390                 395                 400

Leu Glu Ala Ile

<210> SEQ ID NO 21
<211> LENGTH: 404
<212> TYPE: PRT
<213> ORGANISM: Arabidopsis thaliana

<400> SEQUENCE: 21

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
                20                  25                  30

Thr Asp Ala Ile Thr Thr Pro Val Val Asn Thr Ser Ala Tyr Phe Phe
```

```
            35                  40                  45
Lys Lys Thr Ala Glu Leu Ile Asp Phe Lys Glu Lys Arg Ser Val Ser
 50                  55                  60

Phe Glu Tyr Gly Arg Tyr Gly Asn Pro Thr Thr Val Val Leu Glu Asp
 65                  70                  75                  80

Lys Ile Ser Ala Leu Glu Gly Ala Glu Ser Thr Leu Val Met Ala Ser
                 85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
            115                 120                 125

Met Glu Asn Phe Leu Pro Lys Leu Gly Ile Thr Val Thr Val Ile Asp
130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
            195                 200                 205

Leu Gly Ala Asp Leu Val Val His Ser Ala Thr Lys Tyr Ile Gly Gly
210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
            260                 265                 270

Val Gln Gln Gln Asn Ser Thr Ala Phe Arg Met Ala Glu Ile Leu Glu
            275                 280                 285

Ala His Pro Lys Ala Ser His Val Tyr Tyr Pro Gly Leu Pro Ser His
290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
            340                 345                 350

Ser Ile Val Asp Gln Pro Ala Ile Met Ser Tyr Trp Asp Leu Pro Gln
            355                 360                 365

Gly Glu Arg Leu Lys Tyr Gly Ile Lys Asp Asn Leu Val Arg Phe Ser
            370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 22
<211> LENGTH: 404
<212> TYPE: PRT
<213> ORGANISM: Arabidopsis thaliana

<400> SEQUENCE: 22

Met Ser Val Gln Leu Thr Asp Ser Lys His Ser Phe Leu Ser Ser Asp
```

```
1               5                   10                  15
Gly Ser Leu Thr Val His Ala Gly Glu Arg Leu Gly Arg Gly Ile Val
                20                  25                  30

Thr Asp Ala Ile Thr Thr Pro Val Val Asn Thr Ser Ala Tyr Phe Phe
                35                  40                  45

Lys Lys Thr Ala Glu Leu Ile Asp Phe Lys Glu Lys Arg Ser Val Ser
                50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
                100                 105                 110

Gly His Ile Val Thr Thr Asp Cys Tyr Arg Lys Thr Arg Ile Phe
                115                 120                 125

Met Glu Asn Phe Leu Pro Lys Leu Gly Ile Thr Val Thr Val Ile Asp
                130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
                180                 185                 190

Cys Ile Asp Gly Thr Phe Ala Thr Pro Leu Asn Gln Lys Ala Leu Ala
                195                 200                 205

Leu Gly Ala Asp Leu Val Val His Ser Ala Thr Lys Tyr Ile Ser Gly
210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
                260                 265                 270

Val Gln Gln Gln Asn Ser Thr Ala Phe Arg Met Ala Glu Ile Leu Glu
                275                 280                 285

Ala His Pro Lys Ala Ser His Val Tyr Tyr Pro Gly Leu Pro Ser His
                290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
                340                 345                 350

Ser Ile Val Asp Gln Pro Ala Ile Met Ser Tyr Trp Asp Leu Pro Gln
                355                 360                 365

Glu Glu Arg Leu Lys Tyr Gly Ile Lys Asp Asn Leu Val Arg Phe Ser
                370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 23
<211> LENGTH: 404
```

```
<212> TYPE: PRT
<213> ORGANISM: Arabidopsis thaliana

<400> SEQUENCE: 23

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Val Asn Thr Ser Ala Tyr Phe Phe
            35                  40                  45

Lys Lys Thr Ala Glu Leu Ile Asp Phe Lys Glu Lys Arg Ser Val Ser
50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Ser Thr Thr Asp Cys Tyr Arg Lys Thr Arg Ile Phe
            115                 120                 125

Met Glu Asn Phe Leu Pro Lys Leu Gly Ile Thr Val Thr Val Ile Asp
130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
            195                 200                 205

Leu Gly Ala Asp Leu Val Val His Ser Ala Thr Lys Tyr Ile Gly Gly
210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
            260                 265                 270

Val Gln Gln Gln Asn Ser Thr Ala Phe Arg Met Ala Glu Ile Leu Glu
            275                 280                 285

Ala His Pro Lys Ala Ser His Val Tyr Tyr Pro Gly Leu Pro Ser His
290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
            340                 345                 350

Ser Ile Val Asp Gln Pro Ala Ile Met Ser Tyr Trp Asp Leu Pro Gln
            355                 360                 365

Glu Glu Arg Leu Lys Tyr Gly Ile Lys Asp Asn Leu Val Arg Phe Ser
370                 375                 380

Phe Gly Val Glu Asp Phe Glu Asp Val Lys Ala Asp Ile Leu Gln Ala
385                 390                 395                 400
```

Leu Glu Ala Ile

<210> SEQ ID NO 24
<211> LENGTH: 404
<212> TYPE: PRT
<213> ORGANISM: Arabidopsis thaliana

<400> SEQUENCE: 24

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Asn Thr Ser Ala Tyr Phe Phe
        35                  40                  45

Lys Lys Thr Ala Glu Leu Ile Asp Phe Lys Lys Arg Ser Val Ser
50                  55                  60

Phe Glu Tyr Gly Arg Tyr Gly Asn Pro Thr Thr Val Val Leu Glu Glu
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
                100                 105                 110

Gly His Ile Val Thr Thr Thr Asp Cys Tyr Arg Lys Thr Arg Ile Phe
                115                 120                 125

Met Glu Asn Phe Leu Pro Lys Leu Gly Ile Thr Val Thr Val Ile Asp
                130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
                180                 185                 190

Cys Ile Asp Gly Thr Phe Ala Thr Pro Leu Asn Gln Lys Ala Leu Ala
                195                 200                 205

Leu Gly Ala Asp Leu Val Val His Ser Ala Thr Lys Tyr Ile Gly Gly
        210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
                260                 265                 270

Val Gln Gln Gln Asn Ser Thr Ala Phe Arg Met Ala Glu Ile Leu Glu
        275                 280                 285

Ala His Pro Lys Ala Ser His Val Tyr Tyr Pro Gly Leu Pro Ser His
        290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
                340                 345                 350

Ser Ile Val Asp Gln Pro Ala Ile Met Ser Tyr Trp Asp Leu Pro Gln
            355                 360                 365

```
Glu Glu Arg Leu Lys Tyr Gly Ile Lys Asp Asn Leu Val Arg Phe Ser
        370                 375                 380

Phe Gly Val Glu Asp Phe Glu Asp Val Lys Ala Asp Ile Leu Gln Ala
385                 390                 395                 400

Leu Glu Ala Val

<210> SEQ ID NO 25
<211> LENGTH: 404
<212> TYPE: PRT
<213> ORGANISM: Arabidopsis thaliana

<400> SEQUENCE: 25

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Val Asn Thr Ser Ala Tyr Phe Phe
        35                  40                  45

Lys Lys Thr Ala Glu Leu Ile Asp Phe Lys Glu Lys Arg Ser Val Ser
50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
    130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Phe Cys His Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
    210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
            260                 265                 270

Val Gln Gln Gln Asn Ser Thr Ala Phe Arg Met Ala Glu Ile Leu Glu
        275                 280                 285

Ala His Pro Lys Ala Ser His Val Tyr Tyr Pro Gly Leu Pro Ser His
    290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335
```

```
Asp Ser Leu Lys Ile Pro Tyr Ile Ala Pro Ser Phe Gly Gly Cys Glu
            340                 345                 350

Ser Ile Val Asp Gln Pro Ala Ile Met Ser Tyr Trp Asp Leu Pro Gln
            355                 360                 365

Glu Glu Arg Leu Lys Tyr Gly Ile Lys Asp Asn Leu Val Arg Phe Ser
370                 375                 380

Phe Gly Val Glu Asp Phe Glu Asp Val Lys Ala Asp Ile Leu Gln Ala
385                 390                 395                 400

Leu Glu Ala Val

<210> SEQ ID NO 26
<211> LENGTH: 404
<212> TYPE: PRT
<213> ORGANISM: Arabidopsis thaliana

<400> SEQUENCE: 26

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Asn Thr Ser Ala Tyr Phe Phe
        35                  40                  45

Lys Lys Thr Ala Glu Leu Ile Asp Phe Lys Lys Arg Ser Val Ser
50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
210                 215                 220

His Asn Asp Val Leu Ala Gly Cys Ile Cys Gly Ser Leu Lys Leu Val
225                 230                 235                 240

Ser Glu Ile Arg Asn Leu His Val Leu Gly Gly Thr Leu Asn Pro
                245                 250                 255

Asn Ala Ala Tyr Leu Ile Ile Arg Gly Met Lys Thr Leu His Leu Arg
            260                 265                 270

Val Gln Gln Gln Asn Ser Thr Ala Phe Arg Met Ala Glu Ile Leu Glu
        275                 280                 285

Ala His Pro Lys Ala Ser His Val Tyr Tyr Pro Gly Leu Pro Ser His
290                 295                 300
```

```
Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
            340                 345                 350

Ser Ile Val Asp Gln Pro Ala Ile Met Ser Tyr Trp Asp Leu Ser Gln
        355                 360                 365

Glu Glu Arg Leu Lys Tyr Gly Ile Lys Asp Asn Leu Val Arg Phe Ser
    370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 27
<211> LENGTH: 404
<212> TYPE: PRT
<213> ORGANISM: Arabidopsis thaliana

<400> SEQUENCE: 27

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Val Asn Thr Ser Ala Tyr Phe Phe
        35                  40                  45

Lys Lys Thr Ala Glu Leu Ile Asp Phe Lys Glu Lys Arg Ser Val Ser
    50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
    130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
    210                 215                 220

His Asn Asp Val Leu Ala Gly Cys Ile Cys Gly Ser Leu Lys Leu Val
225                 230                 235                 240

Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
            260                 265                 270
```

```
Val Gln Gln Gln Asn Ser Thr Ala Phe Arg Met Ala Glu Ile Leu Glu
            275                 280                 285

Ala His Pro Lys Val Ser His Val Tyr Tyr Pro Gly Leu Pro Ser His
        290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
            340                 345                 350

Ser Ile Val Asp Gln Pro Ala Ile Met Ser Tyr Trp Asp Leu Pro Gln
        355                 360                 365

Glu Glu Arg Leu Lys Tyr Gly Ile Lys Asp Asn Leu Val Arg Phe Ser
370                 375                 380

Phe Gly Val Glu Asp Phe Glu Asp Val Lys Ala Asp Ile Leu Gln Ala
385                 390                 395                 400

Leu Glu Ala Val

<210> SEQ ID NO 28
<211> LENGTH: 404
<212> TYPE: PRT
<213> ORGANISM: Arabidopsis thaliana

<400> SEQUENCE: 28

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
                20                  25                  30

Thr Asp Ala Ile Thr Thr Pro Val Val Asn Thr Ser Ala Tyr Phe Phe
            35                  40                  45

Lys Lys Thr Ala Glu Leu Ile Asp Phe Lys Lys Arg Ser Val Ser
        50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Ile Cys His Lys Arg Gly Thr Leu Val
            180                 185                 190

Cys Ile Asp Gly Thr Phe Ala Thr Pro Leu Asn Gln Lys Ala Leu Ala
        195                 200                 205

Leu Gly Ala Asp Leu Val Val His Ser Ala Thr Lys Tyr Ile Gly Gly
210                 215                 220

His Asn Asp Val Leu Ala Gly Cys Ile Cys Gly Ser Leu Lys Leu Val
225                 230                 235                 240
```

```
Ser Glu Ile Arg Asn Leu His His Val Leu Gly Gly Thr Leu Asn Pro
                245                 250                 255

Asn Ala Ala Tyr Leu Ile Ile Arg Gly Met Lys Thr Leu His Leu Arg
            260                 265                 270

Val Gln Gln Asn Ser Thr Ala Phe Arg Met Ala Glu Ile Leu Glu
        275                 280                 285

Ala His Pro Lys Ala Ser His Val Tyr Tyr Pro Gly Leu Pro Ser His
    290                 295                 300

Pro Glu His Glu Leu Ala Lys Arg Gln Met Thr Gly Phe Gly Gly Val
305                 310                 315                 320

Val Ser Phe Glu Ile Asp Gly Asp Ile Glu Thr Thr Ile Lys Phe Val
                325                 330                 335

Asp Ser Leu Lys Ile Pro Tyr Ile Ala Pro Ser Phe Gly Gly Cys Glu
                340                 345                 350

Ser Ile Val Asp Gln Pro Ala Ile Met Ser Tyr Trp Asp Leu Pro Gln
            355                 360                 365

Glu Glu Arg Leu Lys Tyr Gly Ile Lys Asp Asn Leu Val Arg Phe Ser
370                 375                 380

Phe Gly Val Glu Asp Phe Glu Asp Val Lys Ala Asp Ile Leu Gln Ala
385                 390                 395                 400

Leu Glu Ala Ile

<210> SEQ ID NO 29
<211> LENGTH: 404
<212> TYPE: PRT
<213> ORGANISM: Arabidopsis thaliana

<400> SEQUENCE: 29

Met Ser Val Gln Leu Thr Asp Ser Lys His Ser Phe Leu Ser Ser Asp
1               5                   10                  15

Gly Ser Leu Thr Val His Ala Gly Glu Arg Leu Gly Arg Gly Ile Val
            20                  25                  30

Thr Asp Ala Ile Thr Thr Pro Val Val Asn Thr Ser Ala Tyr Phe Phe
        35                  40                  45

Lys Lys Thr Ala Glu Leu Ile Asp Phe Lys Glu Lys Arg Ser Val Ser
    50                  55                  60

Phe Glu Tyr Gly Arg Tyr Gly Asn Pro Thr Thr Val Val Leu Glu Asp
65                  70                  75                  80

Lys Ile Ser Ala Leu Glu Gly Ala Glu Ser Thr Leu Val Met Ala Ser
                85                  90                  95

Gly Met Cys Ala Ser Thr Val Met Leu Leu Ala Leu Val Pro Ala Gly
            100                 105                 110

Gly His Ile Val Thr Thr Thr Asp Cys Tyr Arg Lys Thr Arg Ile Phe
        115                 120                 125

Met Glu Asn Phe Leu Pro Lys Leu Gly Ile Thr Val Thr Val Ile Asp
    130                 135                 140

Pro Ala Asp Ile Ala Gly Leu Glu Ala Ala Val Asn Glu Phe Lys Val
145                 150                 155                 160

Ser Leu Phe Phe Thr Glu Ser Pro Thr Asn Pro Leu Leu Arg Cys Val
                165                 170                 175

Asp Ile Glu Leu Val Ser Lys Phe Cys His Lys Arg Gly Thr Leu Val
            180                 185                 190

Cys Ile Asp Gly Thr Phe Ala Thr Pro Leu Asn Gln Lys Ala Leu Ala
        195                 200                 205
```

```
Leu Gly Ala Asp Leu Val Val His Ser Ala Thr Lys Tyr Ile Gly Gly
    210             215             220

His Asn Asp Val Leu Ala Gly Cys Ile Cys Gly Ser Leu Lys Leu Val
225             230             235             240

Ser Glu Ile Arg Asn Leu His His Val Leu Gly Gly Thr Leu Asn Pro
            245             250             255

Asn Ala Ala Tyr Leu Ile Ile Arg Gly Met Lys Thr Leu His Leu Arg
            260             265             270

Val Gln Gln Gln Asn Ser Thr Ala Phe Arg Met Ala Glu Ile Leu Glu
        275             280             285

Ala His Pro Lys Val Ser His Val Tyr Tyr Pro Gly Leu Pro Ser His
    290             295             300

Pro Glu His Glu Leu Ala Lys Arg Gln Met Thr Gly Phe Gly Gly Val
305             310             315             320

Val Ser Phe Glu Ile Asp Gly Asp Ile Glu Thr Thr Ile Lys Phe Val
            325             330             335

Asp Ser Leu Lys Ile Pro Tyr Ile Ala Pro Ser Phe Gly Gly Cys Glu
            340             345             350

Ser Ile Val Asp Gln Pro Ala Ile Met Ser Tyr Trp Asp Leu Pro Gln
            355             360             365

Glu Glu Arg Leu Lys Tyr Gly Ile Lys Asp Asn Leu Val Arg Phe Ser
370             375             380

Phe Gly Val Glu Asp Phe Glu Asp Val Lys Ala Asp Ile Leu Gln Ala
385             390             395             400

Leu Glu Ala Ile
```

MEANS AND METHODS FOR THE ENZYMATIC PRODUCTION OF L-METHIONINE FROM O-PHOSPHO-L-HOMOSERINE AND METHANETHIOL

The present invention relates to a method for producing L-methionine in which O-phospho-L-homoserine and methanethiol are enzymatically converted into L-methionine and $H_3PO_4$. Such a conversion is achieved by an enzyme called O-phospho-L-homoserine (OHPS) dependent methionine synthase. The present invention also provides O-phospho-L-homoserine dependent methionine synthases, i.e. proteins which are able to enzymatically convert O-phospho-L-homoserine and methanethiol into L-methionine and $H_3PO_4$. The present invention also relates to microorganisms which have been genetically modified so as to be able to produce L-methionine from O-phospho-L-homoserine and methanethiol.

The described enzymes and processes can also be advantageously used to synthesize derivates of methionine such as S-adenosyl methionine, gluthatione, cystein, S-adenosyl homocysteine and methyl-thio-adenosine. The present invention also provides methods to screen for enzymes that catalyse the conversion of O-phospho-L-homoserine and methanethiol into L-methionine and $H_3PO_4$.

L-methionine is an essential amino acid originating in the metabolism from L-aspartate by activation to L-aspartyl phosphate followed by reduction to L-aspartate semialdehyde and L-homoserine. In bacteria as well as in fungi, L-homoserine undergoes O-acetylation to form either a succinyl or an acetyl ester which itself is subjected to sulfur condensation either directly with sulfide ($SH_2$) to form L-homocysteine or indirectly with L-cysteine to form L-cystathionine prior to conversion to homocysteine. Methylation of homocysteine ensues, using methyltetrahydrofolate, to form L-methionine.

In plants the L-homoserine ester used as a precursor of cystathionine is O-phospho-L-homoserine. Cystathionine is then converted into homocysteine by the action of a cystathionine beta lyase. Methylation of homocysteine then leads to methionine. O-phospho-L-homoserine also occurs in the metabolism of bacteria, plants, fungi and mammalian cells as the direct precursor of L-threonine through the action of the phosphor-pyridoxal enzyme threonine synthase (EC 4.2.3.1). In plants, there is a strict regulation in order to control carbon flux to methionine and threonine at the O-phospho-L-homoserine branch point (Amir et al., TRENDS Plant Science 7 (2002), 153). It has been reported in the literature (see, e.g., Kreft et al., Plant Physiol. 104 (1994), 1215; Ravanel et al., Arch. Biochem. Biophys. 316 (1995), 572) that both L-cysteine and sulfide ($SH_2$) can be condensed by plant cystathionine gamma synthase with O-phospho-L-homoserine into L-cystathionine and L-homocysteine with the simultaneous release of phosphate. It was also reported that the thiol substrate range is very restricted with only few substrates being accepted besides L-cysteine.

Although it is an essential amino acid, methionine is not synthesized de novo in animals, who must ingest methionine or methionine-containing proteins or related sulfur containing compounds. In particular, methionine is essential for poultry and livestock feeding and is not present in sufficient quantities in the vegetable matter they eat. Efficient farming therefore needs external methionine supply. Up to date, most if not all of the methionine used to feed animals comes from petrol chemistry. One limitation of methionine production is the energy cost of sulfur reduction. Thus, there is a need to be able to provide alternative ways to produce this amino acid, preferably by using renewable resources which would allow using microorganisms in which methionine synthesis is compatible with an industrial scale production.

The present invention addresses this need by providing a method for the production of L-methionine in which O-phospho-L-homoserine and methanethiol are enzymatically converted into L-methionine and $H_3PO_4$. In such a method the source of sulfur is methanethiol. In this compound sulfur is provided as a sulfide, already reduced. Furthermore, the use of O-phospho-L-homoserine as a precursor spares at least two carbon atoms per molecule of methionine synthesized as compared to the standard metabolic pathway that relies on the use of acetylated or succinylated homoserine derivatives. Altogether this pathway allows much better yields in the synthesis of methionine and derivatives thereof.

Thus, the present invention relates to a method for the production of L-methionine in which L-methionine is enzymatically produced according to the following reaction scheme:

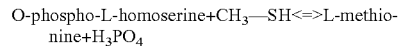

There is no report so far that there exists in nature a protein which has the ability to convert O-phospho-L-homoserine and methanethiol into L-methionine. The present inventors considered the option to produce L-methionine in a cost efficient manner from O-phospho-L-homoserine and methanethiol and for this purpose engineered proteins which do not naturally occur and which have the ability to convert O-phospho-L-homoserine and methanethiol into L-methionine. As is evident from the appended Examples, the present inventors developed a system which allows for creating for enzymes which have the ability to convert O-phospho-L-homoserine and methanethiol into L-methionine and $H_3PO_4$. Moreover, the inventors have been successful by applying this system to create new enzyme variants, derived from existing enzymes, which have the ability to convert O-phospho-L-homoserine and methanethiol into L-methionine and $H_3PO_4$. For this purpose they started out from existing enzymes which do not show the ability to convert O-phospho-L-homoserine and methanethiol into L-methionine and $H_3PO_4$, prepared mutants from such existing enzymes and selected enzymes which show the ability to convert O-phospho-L-homoserine and methanethiol into L-methionine and $H_3PO_4$. Thus, the inventors could establish a new enzyme activity which had previously not been described and provide reliable and reproducible methods for providing corresponding enzymes. The corresponding enzymes are referred to in the context of the present invention as O-phospho-L-homoserine dependent methionine synthases.

Thus, the present invention in particular relates to a method for the production of L-methionine in which O-phospho-L-homoserine and methanethiol are enzymatically converted into L-methionine and $H_3PO_4$ according to the following reaction scheme:

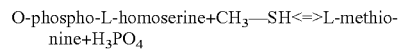

wherein the enzymatic conversion is achieved by making use of an O-phospho-L-homoserine dependent methionine synthase.

In principle, any O-phospho-L-homoserine dependent methionine synthase, i.e. any protein which has the ability to convert O-phospho-L-homoserine and methanethiol into L-methionine and $H_3PO_4$, can be employed in the method according to the invention. The present invention for the first time describes proteins showing this ability and provides methods for providing further proteins showing this ability. In particular, the present invention discloses that it is possible to create, starting from a plant cystathionine gamma synthase (EC 2.5.1.48), which naturally does not have the capacity to convert O-phospho-L-homoserine and methanethiol into L-methionine, variants which have this capacity by mutation and selection.

O-phospho-L-homoserine dependent methionine synthases will be described further below in the context of the protein according to the invention and any O-phospho-L-homoserine dependent methionine synthase described can be employed in the method according to the invention.

As is evident from the appended Examples, the inventors were successful in creating several different proteins which show the ability to convert O-phospho-L-homoserine and methanethiol into L-methionine and $H_3PO_4$. The sequences of these proteins are shown in SEQ ID NOs: 6 to 29. These proteins are created by mutation and selection in a screening system as described in the Examples from a plant cystathionine gamma synthase (EC 2.5.1.48), which naturally does not have the capacity to convert O-phospho-L-homoserine and methanethiol into L-methionine.

Moreover, starting from the sequences shown in SEQ ID NOs: 6 to 29 it is possible to provide further proteins which retain the activity to convert O-phospho-L-homoserine and methanethiol into L-methionine and $H_3PO_4$. It is, e.g., possible to further increase the affinity of the proteins to the substrate O-phospho-L-homoserine and/or to the substrate methanethiol or to improve other properties of the protein as described further below. Thus, in a preferred embodiment of the method according to the present invention the enzymatic conversion of O-phospho-L-homoserine and methanethiol into L-methionine and $H_3PO_4$ is achieved by making use of a protein selected from the group consisting of:
(a) a protein comprising the amino acid sequence as shown in any one of SEQ ID NOs: 6 to 29; and
(b) a protein having a sequence identity of at least 60% to any one of SEQ ID NOs: 6 to 29 and having the enzymatic activity of converting O-phospho-L-homoserine and methanethiol into L-methionine and $H_3PO_4$.

The enzymatic activity of converting O-phospho-L-homoserine and methanethiol into L-methionine and $H_3PO_4$ can, for example, be assessed by an assay as described in the appended Examples. For this purpose, it is, e.g., possible to use an S. cerevisiae strain which has an auxotroph phenotype for methionine. Examples for such a strain are strains in which the enzymes homoserine trans-acetylase and homocysteine synthase are removed or rendered dysfunctional. Preferably both enzymes are removed or dysfunctional. As shown in FIG. 1, S. cerevisiae relies on the obligatory use of O-acetyl-homoserine to synthesize homocysteine which is then converted into methionine. The enzyme homoserine transacetylase responsible for the synthesis of O-acetyl-homoserine is encoded by the MET2 gene. Upon MET2 inactivation, homoserine can no longer be converted into O-acetyl homoserine and all the homoserine flux is diverted towards phosphohomoserine. As the MET2 catalyzed reaction is the only source of O-acetyl homoserine in yeast, inactivation of the MET2 gene results in yeast strains displaying a strict methionine auxotrophy phenotype. However, homocysteine (the last methionine precursor) can derive from either cysteine (through the transsulfuration pathway) or from the recycling of S-adenosylmethionine. In order to make sure that no methionine can be synthesized at all, MET6, the gene which codes for homocysteine methyltransferase which is responsible for the synthesis of methionine from homocysteine and methyltetrahydrofolate is also deleted.

Thus, in an assay for testing for the ability of a protein to convert O-phospho-L-homoserine and methanethiol into L-methionine and $H_3PO_4$ one can preferably use an S. cerevisiae strain in which the MET2 and/or the MET6 genes, preferably both, are deleted or disrupted. A double met2Δ met6Δ disrupted strain is unable to grow in the absence of methionine and in particular can not grow in the presence of methanethiol as the source of sulfur. Such a strain is no longer able to synthesize O-acetyl homoserine but produces O-phospho-homoserine. Such a yeast strain can then be transformed with a nucleic acid molecule encoding a protein to be tested for the ability of converting O-phospho-L-homoserine and methanethiol into L-methionine and $H_3PO_4$. The strain is grown in/on a medium which contains methanethiol as the sole sulfur source and the ability of growing on such a medium is indicative of the expressed protein being able to convert O-phospho-L-homoserine (OHPS) and methanethiol into L-methionine and $H_3PO_4$. It is even more preferable to use a strain in which also the gene encoding threonine synthase is rendered inactive, e.g. by deletion or disruption. In met2Δ met6Δ strains OPHS is synthesized in a reaction catalyzed by the homoserine kinase encoded by the THR1 gene but it may not efficiently accumulate because of its active conversion into threonine by the threonine synthase encoded by the THR4 gene. Such triple met2Δ met6Δ thr4Δ mutant strains thus allow to detect very low activity of OPHS dependent methionine synthase and have been used as a first screening of cells to isolate new proteins endowed with OPHS dependant methione synthase activity.

This enzymatic activity can also further be confirmed by an in vitro assay in which O-phospho-L-homoserine and methanethiol are incubated in vitro under suitable conditions with an acellular extract from a yeast strain expressing a protein to be tested or with a (partially) purified protein to be tested and in which the production of methionine is detected by liquid chromatography/mass spectrometry/mass spectrometry (LC/MS/MS) using $C^{13}$ methionine as an internal control (Ravanel et al. Archives of Biochemistry and Biophysics 316 (1995), 572-584).

The O-phospho-L-homoserine used in such an in vitro assay as a substrate can be provided, e.g., by a process as shown in FIG. 2 (Barclay et al., J. Chem. Soc, Chem. Com (1994) 815-816).

As mentioned above, examples for proteins which show the enzymatic activity of converting O-phospho-L-homoserine and methanethiol into L-methionine and $H_3PO_4$ are those having an amino acid sequence as shown in any one of SEQ ID NOs: 6 to 29. Thus, in one preferred embodiment the method according to the present invention makes use of a protein comprising an amino acid sequence as shown in any one of SEQ ID NOs: 6 to 29. However, it is of course also possible to employ variants of these proteins, i.e. proteins the amino acid sequence of which shows a high degree of sequence identity to an amino acid sequence as shown in any one of SEQ ID NOs: 6 to 29 and which show the enzymatic activity of converting O-phospho-L-homoserine and methanethiol into L-methionine and $H_3PO_4$. The sequence identity is at least 60%, preferably at least 70%, even more preferably at least 80%, at least 85%, at least 90% or at least 95% and most preferably at least 96%, 97%, 98% or 99% to a sequence as shown in any one of SEQ ID NOs: 6 to 29. Preferably, the degree of identity is determined by comparing the respective sequence with an amino acid sequence as shown in any one of SEQ ID NOs: 6 to 29. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence. Moreover, if the term "homology" is used in the context of the present invention, this term preferably means "sequence identity".

The method according to the invention also allows producing other sulfur containing compounds which are derived from L-methionine. Examples of such compounds are S-adenosyl methionine, gluthatione, cysteine, S-adenosyl homocysteine, methyl-thio-adenosine and 2-oxo-4-methylthiobutanoate.

Thus, the present invention also relates to a method for producing S-adenosyl methionine which comprises the method for producing L-methionine according to the invention as described above and in which L-methionine is further converted into S-adenosyl methionine according to the following reaction:

Methionine+ATP=>S-adenosylmethionine+PP<sub>i</sub>+P<sub>i</sub>

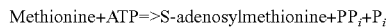

This enzymatic reaction is known in the art and enzymes catalyzing this reaction are known in the art. These enzymes are called S-adenosylmethionine synthases (EC 2.5.1.6). Examples for corresponding enzymes are SAM1 and SAM2 in yeast. Thus, in the case where such a method is carried out in an organism, such an organism preferably overexpresses the corresponding enzyme(s) which is/are capable of converting L-methionine into S-adenosyl methionine.

It may also be advantageous to further modify such an organism in order to prevent the flux of S-adenosyl methionine into other metabolic pathways. In yeast it may, for example, be advantageous to inactivate the adenosine kinase activity (EC 2.7.1.20 encoded by the ADO1 gene in yeast) in order to decrease the flux of S-adenosyl methionine to S-adenosyl homocysteine.

Moreover, the present invention also relates to a method for the production of cysteine which comprises the method for producing L-methionine according to the invention as described above and in which L-methionine is further converted into cysteine. The conversion of L-methionine into cysteine is known in the prior art and can be achieved by means and methods known to the skilled person. For example, L-methionine can be first converted into S-adenosyl methionine which is then further converted into S-adenosyl homocysteine according to the following reaction:

S-adenosylmethionine+a methyl-acceptor=>S-adenosylhomocysteine+a methylated-acceptor

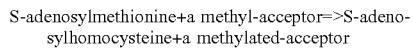

This reaction is catalyzed by S-adenosylmethionine-dependent methyltransferases.

S-adenosyl homocysteine can then be further converted into L-homocysteine according to the following reaction:

S-adenosylhomocysteine<=>L-homocysteine+adenosine

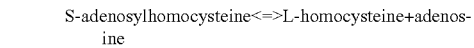

This reaction is catalyzed by S-adenosylhomocysteine hydrolase, EC 3.3.1.1.

Subsequently L-homocysteine can be converted into L-cystathionine according to the following reaction:

L-homocysteine+L-serine<=>L-cystathionine+H<sub>2</sub>O

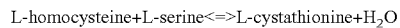

This reaction is catalyzed by cystathionine beta-synthase (EC 4.2.1.22).

Finally, L-cystathionine is converted into cysteine according to the following reaction:

L-cystathionine+H<sub>2</sub>O<=>L-cysteine+NH<sub>3</sub>+oxobutanoate

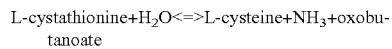

This reaction is catalyzed by cystathionine gamma-lyase (EC 4.4.1.1).

If such a method is carried out in yeast, it is advantageous to overexpress the following genes: SAM1, SAM2, SAH1, STR4 and STR1. In addition the gene STR2 encoding the yeast cystathionine gamma synthase should be deleted in order to lower the reverse synthesis from cysteine to homocysteine. Likewise, such a yeast advantageously also comprises a MET6 mutation abolishing the methyltetrahydrofolate-dependent methionine synthase as well as a deletion of the DUG2 gene which is involved in the main glutathione degradation pathway.

Moreover, the present invention also relates to a method for the production of glutathione which comprises the method for producing L-methionine according to the invention as described above and in which L-methionine is further converted into glutathione. The conversion of L-methionine into glutathione is known in the prior art and can be achieved by means and methods known to the skilled person. For example, L-methionine can be first converted into S-adenosyl methionine which is then further converted into cysteine as described above and the cysteine thus produced is further converted into Glu-Cys (gamma-L-glutamyl-L-cysteine) according to the following reaction:

ATP+L-glutamate+L-cysteine<=>gamma-L-glutamyl-L-cysteine+ADP+P<sub>i</sub>

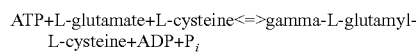

This reaction is catalyzed by glutamate cysteine ligase (EC 6.3.2.2).

The thus produced Glu-Cys is then further converted into glutathione according to the following reaction:

ATP+gamma-L-glutamyl-L-cysteine+glycine=glutathione+ADP+P<sub>i</sub>

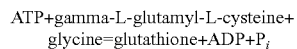

This reaction is catalyzed by glutathione synthase (EC 6.3.2.3).

If such a method is carried out in yeast, it is preferred that the yeast is engineered as described above in connection with the method for the production of cysteine and such a yeast should also overexpress the genes GSH1 and GSH2 that are involved in the transformation of cysteine into glutathione. In a particularly preferred embodiment the GSH1 gene expresses a feed-back resistant enzyme.

Moreover, the present invention also relates to a method for producing 2-oxo-4-methylthiobutanoate which comprises the method for producing L-methionine according to the invention as described above and in which L-methionine is further converted into 2-oxo-4-methylthiobutanoate according to the following reaction:

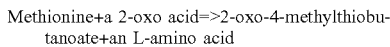

Methionine+a 2-oxo acid=>2-oxo-4-methylthiobutanoate+an L-amino acid

This enzymatic reaction is known in the art and enzymes catalyzing this reaction are known in the art. These enzymes are called methionine transaminase (EC 2.6.1.88). Examples for corresponding enzymes are ARO8, BAT1, BAT2 in yeast. Thus, in the case where such a method is carried out in an organism, such an organism preferably overexpresses the corresponding enzyme(s) which is/are capable of converting L-methionine into 2-oxo-4-methylthiobutanoate.

It may also be advantageous to further modify such an organism in order to prevent the flux of 2-oxo-4-methylthiobutanoate into other metabolic pathways. In yeast it may, for example, be advantageous to inactivate the phenylpyruvate decarboxylase activity (EC 4.1.1.43 encoded by the ARO10 gene in yeast) or the pyruvate decarboxylase activity (EC 4.1.1.1 encoded by the PDC1, PDC5 and PDC6 genes in yeast) in order to decrease the flux of 2-oxo-4-methylthiobutanoate to 3-(methylthio)propionaldehyde.

The method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzyme. In one embodiment, the enzyme employed in the method is used in purified form.

For carrying out the process in vitro the substrates for the reaction and the enzyme are incubated under conditions (buffer, temperature, etc.) allowing the enzyme to be active and the enzymatic conversion to occur. The reaction is allowed to proceed for a time sufficient to produce L-methionine. The production of L-methionine can be measured by methods known in the art.

The enzyme may be in any suitable form allowing the enzymatic reaction to take place. It may be purified or partially purified or in the form of crude cellular extracts or partially purified extracts. It is also possible that the enzyme is immobilized on a suitable carrier.

In another embodiment the method according to the invention is carried out in culture, in the presence of an organism, preferably a microorganism, producing a protein which has the ability of converting O-phospho-L-homoserine and methanethiol into L-methionine and $H_3PO_4$. The protein is a protein as described herein.

The organism employed in such a method is preferably a host cell according to the present invention as described herein.

The present invention also relates to a protein which has the ability to enzymatically convert O-phospho-L-homoserine and methanethiol into L-methionine. In the context of the present invention such an enzyme is referred to as an OHPS dependent methionine synthase. As mentioned above, there is no report so far that there exists in nature a protein which has the ability to convert O-phospho-L-homoserine and methanethiol into L-methionine and the present invention is the first to provide such proteins which allow to produce L-methionine according to the method of the invention as described herein above.

In a preferred embodiment, the protein according to the invention which has the ability to enzymatically convert O-phospho-L-homoserine and methanethiol into L-methionine is derived from a cystathionine gamma synthase (EC 2.5.1.48) by mutation. Such a mutation can be a substitution of one or more amino acid residues and/or a deletion of one or more amino acid residues and/or an addition of one or more amino acid residues in the amino acid sequence of a cystathionine gamma synthase (EC 2.5.1.48).

Cystathionine gamma synthases are known and described for various organisms. For example, for plants more than 350 sequences for cystathionine gamma synthase re known, inter alia for *A. thaliana, Nicotiana tabacum, Triticum aestivum, Solanum lycopersicum, Lemna paucicostata, Solanum tuberosum, Spinacia oleracea, Astragalus racemosus, Astragalus bisulcatus, Astragalus sinicus* and *Neptunia amplexicaulis.*

Cystathionine gamma synthases are also known from bacteria and fungi. For bacteria more than 22,000 sequences have been described and examples for bacteril or fungal sequence are those from *Saccharomyces cerevisiae, Neurospora crassa, Salmonella erterica, Escherichia coli, Agrobacterium tumefaciens, Alcaligenes faecalis, Aneurinibacillus aneurinilyticus, Bacillus pumius, Bacillus subtilis, Corynebacterium glutamicum, Helicobacter pylori, Lysinibacillus sphaericus, Mycobacterium tuberculosis, Pectobacterium carotovorum, Pseudomonas dacunhae, Pseudomonas putida, Streptomyces phaeochromogenes.*

Methods for providing proteins showing the activity of converting O-phospho-L-homoserine and methanethiol into L-methionine and $H_3PO_4$ are described in the appended Examples and will be described in more detail further below. In principle, any cystathionine gamma synthase (EC 2.5.1.48) can be used as a starting material for providing a protein showing the activity of converting O-phospho-L-homoserine and methanethiol into L-methionine and $H_3PO_4$. It is preferred that the protein showing the activity of converting O-phospho-L-homoserine and methanethiol into L-methionine and $H_3PO_4$ which is derived from a cystathionine gamma synthase (EC 2.5.1.48) shows at least 70%, preferably at least 80%, even more preferably at least 90% and most preferably at least 95% sequence identity to the amino acid sequence of a naturally occurring cystathionine gamma synthase.

In one preferred embodiment the cystathionine gamma synthase (EC 2.5.1.48) from which the OHPS dependent methionine synthase is derived is a plant cystathionine gamma synthase (EC 2.5.1.48), preferably the cystathionine gamma synthase (EC 2.5.1.48) CGS1 from *Arabidopsis thaliana*, most preferably a cystathionine gamma synthase (EC 2.5.1.48) showing the amino acid sequence as shown in SEQ ID NO: 1. In an even more preferred embodiment the OHPS dependent methionine synthase employed in a method according to the present invention is derived from the sequence shown in SEQ ID NO: 2. This sequence corresponds to SEQ ID NO: 1 apart from the fact that the glycine residue at position 84 is replaced by a serine residue. This replacement, i.e. an mto mutation, relieves the translational repression exerted by S-adenosylmethionine on CGS1 (Onoue et al. Journal of Biological Chemistry 286 (2011), 14903-14911). In a particularly preferred embodiment the OHPS dependent methionine synthase employed in a method according to the present invention is derived from the sequence shown in SEQ ID NO: 3. This sequence corresponds to SEQ ID NO: 2 apart from the fact that the amino terminally located chloroplast targeting sequence (amino acid residues 1 to 57) has been removed and a methionine residue is added at the N-terminus.

Examples of an OHPS dependent methionine synthase which can be employed in a method according to the present invention are (i) OHPS dependent methionine synthases which are derived from a cystathionine gamma synthase having the amino acid sequence shown in SEQ ID NO: 3 by substitution or deletion of at least one amino acid residue in SEQ ID NO: 3 selected from the group consisting of:
(a) proline 10;
(b) asparagine 11;
(c) glutamine 15;
(d) isoleucine 27;
(e) alanine 30;
(f) leucine 45;
(g) serine 47;
(h) valine 60;
(i) alanine 68;
(j) phenylalanine 150;
(k) threonine 178;
(l) aspartate 183;
(m) isoleucine 185;
(n) threonine 220;
(o) methionine 232;
(p) valine 245;
(q) alanine 257;
(r) asparagine 259;
(s) phenylalanine 261;
(t) phenylalanine 275;
(u) isoleucine 287;
(v) histidine 289;
(w) tyrosine 324;
(x) glycine 326;
(y) proline 356;
(z) threonine 371;
(aa) valine 396;
(bb) proline 405;
(cc) aspartate 431;
(dd) isoleucine 436;
(ee) isoleucine 457;
(ff) aspartate 459;
(gg) proline 470;
(hh) glutamate 472;
(ii) alanine 506;
(jj) isoleucine 507.
or
(ii) OHPS dependent methionine synthases which are derived from a cystathionine gamma synthase, the amino acid sequence of which shows at least 60% sequence identity to the amino acid sequence shown in SEQ ID NO: 3, by substitution or deletion of at least one amino acid residue corresponding to any one of (a) to (jj) listed above in SEQ ID NO: 3. Preferably, the sequence identity is at least 70%, even more preferably at least 80% and most preferably at least 90%.

The term "substitution" means that the amino acid occurring at the indicated position is substituted with another amino acid residue. In the context of the present invention, "substituted with another amino acid residue" means that the respective amino acid residues at the indicated position can be substituted with any other possible amino acid residues, preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below.

Amino acid residues located at a position corresponding to a position selected from the group consisting of positions (a) to (jj) listed above in the amino acid sequence shown in SEQ ID NO: 3 can be identified by the skilled person by methods known in the art. For example, such amino acid residues can be identified by aligning the sequence in question with the sequence shown in SEQ ID NO: 3 and by identifying the positions which correspond to the above indicated positions of SEQ ID NO: 3. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

When amino acid sequences are aligned by means of such a method, regardless of insertions or deletions that occur in the amino acid sequences, the positions of the corresponding amino acid residues can be determined in a given sequence.

According to one embodiment, the OHPS dependent methionine synthases of the present invention has an amino acid sequence in which
(i) the amino acid residue at position 10 in the amino acid sequence shown in SEQ ID NO: 3 or at a position corresponding to this position, is substituted with leucine; and/or
(ii) the amino acid residue at position 11 in the amino acid sequence shown in SEQ ID NO: 3 or at a position corresponding to this position, is substituted with aspartate; and/or
(iii) the amino acid residue at position 15 in the amino acid sequence shown in SEQ ID NO: 3 or at a position corresponding to this position, is substituted with arginine; and/or
(iv) the amino acid residue at position 27 in the amino acid sequence shown in SEQ ID NO: 3 or at a position corresponding to this position, is substituted with serine; and/or
(v) the amino acid residue at position 30 in the amino acid sequence shown in SEQ ID NO: 3 or at a position corresponding to this position, is substituted with threonine; and/or
(vi) the amino acid residue at position 45 in the amino acid sequence shown in SEQ ID NO: 3 or at a position corresponding to this position, is substituted with serine; and/or
(vii) the amino acid residue at position 47 in the amino acid sequence shown in SEQ ID NO: 3 or at a position corresponding to this position, is substituted with threonine; and/or
(viii) the amino acid residue at position 60 in the amino acid sequence shown in SEQ ID NO: 3 or at a position corresponding to this position, is substituted with aspartate; and/or
(ix) the amino acid residue at position 68 in the amino acid sequence shown in SEQ ID NO: 3 at a position corresponding to this position, is substituted with threonine; and/or
(x) the amino acid residue at position 150 in the amino acid sequence shown in SEQ ID NO: 3 or at a position corresponding to this position, is substituted with leucine; and/or
(xi) the amino acid residue at position 178 in the amino acid sequence shown in SEQ ID NO: 3 or at a position corresponding to this position, is substituted with isoleucine; and/or
(xii) the amino acid residue at position 183 in the amino acid sequence shown in SEQ ID NO: 3 or at a position corresponding to this position, is substituted with glutamate; and/or (xiii) the amino acid residue at position 185 in the amino acid sequence shown in SEQ ID NO: 3 at a position corresponding to this position, is substituted with valine; and/or (xiv) the amino acid residue at position 220 in the amino acid sequence shown in SEQ ID NO: 3 or at a position corresponding to this position, is substituted with serine; and/or (xv) the amino acid residue at position 232 in the amino acid sequence shown in SEQ ID NO: 3 or at a position corresponding to this position, is substituted with leucine; and/or (xvi) the amino acid residue at position 245 in the amino acid sequence shown in SEQ ID NO: 3 or at a position corresponding to this position, is substituted with alanine; and/or (xvii) the amino acid residue at position 257 in the amino acid sequence shown in SEQ ID NO: 3 or at a position corresponding to this position, is substituted with threonine; and/or (xviii) the amino acid residue at position 259 in the amino acid sequence shown in SEQ ID NO: 3 or at a position corresponding to this position, is substituted with aspartate or serine; and/or (xiv) the amino acid residue at position 261 in the amino acid sequence shown in SEQ ID NO: 3 or at a position corresponding to this position, is substituted with serine; and/or (xx) the amino acid residue at position 275 in the amino acid sequence shown in SEQ ID NO: 3 or at a position corresponding to this position, is substituted with leucine; and/or (xxi) the amino acid residue at position 287 in the amino acid sequence shown in SEQ ID NO: 3 or at a position corresponding to this position, is substituted with valine or phenylalanine; and/or (xxii) the amino acid residue at position 289 in the amino acid sequence shown in SEQ ID NO: 3 or at a position corresponding to this position, is substituted with tyrosine or arginine; and/or (xxiii) the amino acid residue at position 324 in the amino acid sequence shown in SEQ ID NO: 3 or at a position corresponding to this position, is substituted with phenylalanine; and/or (xxiv) the amino acid residue at position 326 in the amino acid sequence shown in SEQ ID NO: 3 or at a position corresponding to this position, is substituted with serine; and/or (xxv) the amino acid residue at position 356 in the amino acid sequence shown in SEQ ID NO: 3 or at a position corresponding to this position, is substituted with threonine; and/or (xxvi) the amino acid residue at position 371 in the amino acid sequence shown in SEQ ID NO: 3 or at a position corresponding to this position, is substituted with alanine; and/or (xxvii) the amino acid residue at position 396 in the amino acid sequence shown in SEQ ID NO: 3 or at a position corresponding to this position, is substituted with alanine; and/or (xxviii) the amino acid residue at position 405 in the amino acid sequence shown in SEQ ID NO: 3 or at a position corresponding to this position, is substituted with serine; and/or (xxix) the amino acid residue at position 431 in the amino acid sequence shown in SEQ ID NO: 3 or at a position corresponding to this position, is substituted with glycine; and/or (xxx) the amino acid residue at position 436 in the amino acid sequence shown in SEQ ID NO: 3 or at a position corresponding to this position, is substituted with threonine; and/or (xxxi) the amino acid residue at position 457 in the amino acid sequence shown in SEQ ID NO: 3 or at a position corresponding to this position, is substituted with leucine; and/or (xxxii) the amino acid residue at position 459 in the amino acid sequence shown in SEQ ID NO: 3 or at a position corresponding to this position, is substituted with asparagine; and/or (xxxiii) the amino acid residue at position 470 in the amino acid sequence shown in SEQ ID NO: 3 or at a position corresponding to this position, is substituted with serine; and/or (xxxiv) the amino acid residue at position 472 in the amino acid sequence shown in SEQ ID NO: 3 or at a position corresponding to this position, is substituted with glycine; and/or (xxxv) the amino acid residue at position 506 in the amino acid sequence shown in SEQ ID NO: 3 or at a position corresponding to this position, is substituted with glycine; and/or (xxxvi) the amino acid residue at position 507 in the amino acid sequence shown in SEQ ID NO: 3 or at a position corresponding to this position, is substituted with valine.

The invention also relates to variants as defined in (i) to (xxxvi) hereinabove, wherein the amino acid residue indicated as substituting the amino acid residue at the position in SEQ ID NO: 3 but is not that particular amino acid residue but an amino acid residue which is conservative in relation to the indicated substituting amino acid. Whether an amino acid is conservative with respect to another amino acid can be judged according to means and methods known in the art. One possibility is the PAM 250 matrix; alternatively, the Blosum Family Matrices can be used.

In one embodiment the present invention relates to a OHPS dependent methionine synthase having an amino acid sequence as shown in SEQ ID NO: 3 or an amino acid sequence having at least 60% sequence identity to SEQ ID NO: 3, wherein the amino acid residues at position 356 in the amino acid sequence shown in SEQ ID NO: 3 or at a position corresponding to this position is substituted with another amino acid residue. In a preferred embodiment the present invention relates to such a protein in which at least one further amino acid residue is substituted at a position selected from the group consisting of positions 10, 11, 15, 27, 28, 30, 32, 45, 47, 60, 68, 104, 150, 178, 183, 185, 220, 232, 245, 257, 259, 261, 275, 287, 289, 324, 326, 371, 396, 405, 431, 436, 457, 459, 470, 472, 506 and 507, preferably selected from the group consisting of positions 10, 11, 15, 30, 32, 45, 47, 68, 104, 150, 178, 183, 185, 220, 232, 245, 257, 259, 261, 275, 287, 289, 326, 371, 396, 405, 431, 436, 459, 470, 472, 506 and 507, even more preferably selected from the group consisting of residues 275 and 396.

In one embodiment, the positions in which substitutions and/or deletions occur are the following:

In one embodiment, the positions in which substitutions and/or deletions occur are the following: positions 10, 27, 60, 324 and 457.

In one embodiment, the positions in which substitutions and/or deletions occur are the following: positions 32, 287, 289 and 356.

In one embodiment, the positions in which substitutions and/or deletions occur are the following: positions 10, 232, 245, 259, 356, 431 and 436.

In one embodiment, the positions in which substitutions and/or deletions occur are the following: positions 11, 15, 30, 45, 47, 68, 178, 356, 371 and 459.

In one embodiment, the positions in which substitutions and/or deletions occur are the following: positions 32 and 356.

In one embodiment, the positions in which substitutions and/or deletions occur are the following: positions 32, 60, 324 and 457.

In one embodiment, the positions in which substitutions and/or deletions occur are the following: positions 32, 287, 289 and 356.

In one embodiment, the positions in which substitutions and/or deletions occur are the following: positions 32, 232, 245, 259, 356, 431 and 436.

In one embodiment, the positions in which substitutions and/or deletions occur are the following: positions 32, 45, 47, 68, 178, 356, 371 and 459.

In one embodiment, the positions in which substitutions and/or deletions occur are the following: positions 232, 245, 259, 356, 431 and 436.

In one embodiment, the positions in which substitutions and/or deletions occur are the following: positions 178, 356, 371 and 459.

In one embodiment, the positions in which substitutions and/or deletions occur are the following: positions 150, 257, 259, 261, 275, 289, 356 and 506.

In one embodiment, the positions in which substitutions and/or deletions occur are the following: positions 185, 356 and 405.

In one embodiment, the positions in which substitutions and/or deletions occur are the following: positions 275, 356, 396 and 472.

In one embodiment, the positions in which substitutions and/or deletions occur are the following: positions 275, 326, 356 and 396.

In one embodiment, the positions in which substitutions and/or deletions occur are the following: positions 220, 275, 356 and 396.

In one embodiment, the positions in which substitutions and/or deletions occur are the following: positions 183, 275, 356, 396 and 507.

In one embodiment, the positions in which substitutions and/or deletions occur are the following: positions 275, 287, 356, 396 and 507.

In one embodiment, the positions in which substitutions and/or deletions occur are the following: positions 275, 356, 396 and 470.

In one embodiment, the positions in which substitutions and/or deletions occur are the following: positions 275, 356 and 507.

In one embodiment, the positions in which substitutions and/or deletions occur are the following: positions 275, 356 and 396.

In one embodiment, the positions in which substitutions and/or deletions occur are the following: positions 275, 287 and 356.

The preferred substitutions at these positions are those indicated above.

OHPS dependent methionine synthases which can be employed in a method according to the present invention are also enzymes which can be derived from any of the above described OHPS dependent methionine synthases by deletion of one or more N-terminal amino acids corresponding to amino acids 1 to 103 of the amino acid sequence as shown in SEQ ID NO: 3. As shown in the Examples, also truncated forms of the above described OHPS dependent methionine synthases, e.g. truncated forms in which in comparison to SEQ ID NO: 3 31 amino acid residues or 103 amino acid residues are deleted from the N-terminus still show efficient OHPS dependent methionine synthase activity.

In a preferred embodiment the OHPS dependent methionine synthase according to the invention also shows the enzymatic activity of converting O-phospho-L-homoserine and sulfide into L-homocysteine+$H_3PO_4$. Preferably the sulfide is a metal sulfide such as $Na_2S$. In this case the conversion takes place according to the following reaction scheme:

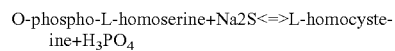

The activity of converting convert O-phospho-L-homoserine (OPHS) and metal sulfide into L-homocysteine and $H_3PO_4$, can be detected in an assay which is basically the same as that described above in connection with the detection of the activity to convert O-phospho-L-homoserine (OPHS) and methanethiol into L-methionine and $H_3PO_4$. In this case, a double met2Δ met25Δ yeast strain is used and is grown on a medium with $Na_2S$ as sole source of sulfate. Indeed MET25 codes the only know homocysteine synthase activity known in yeast, catalyzing the condensation of O-acetyl-L-homoserine with sulfide. The sensitivity of the assay can be readily improved by using *S. cerevisiae* strains that were engineered to comprise, in addition to the double met2 met25 mutations, the thr4 mutation which leads to O-phospho-L-homoserine accumulation.

This enzymatic activity can also further be confirmed by an in vitro assay in which O-phospho-L-homoserine and $Na_2S$ are incubated in vitro under suitable conditions with an acellular extract from a yeast strain expressing a protein to be tested or with a (partially) purified protein to be tested and in which the production of homocysteine is detected by a colorimetric method (Becker et al., Journal of Biochemical Chemistry 244(1969), 2418).

The present invention also relates to nucleic acid molecules encoding a protein according to the invention. The nucleic acid molecule may be DNA or RNA, preferably it is DNA.

The present invention furthermore relates to a vector comprising a nucleic acid molecule according to the invention. In a preferred embodiment, the vector is a vector which allows expression of the nucleic acid according to the invention so as to allow the production of a protein according to the invention. Thus, in a preferred embodiment the nucleic acid according to the invention is operably linked to expression control sequences which allow expression in a desired host cell or host cell system. The term "operatively linked" or "operably linked", as used throughout the present description, refers to a linkage between one or more expression control sequences and the coding region in the nucleic acid molecule to be expressed in such a way that expression is achieved under conditions compatible with the expression control sequence.

Expression comprises transcription of the heterologous DNA sequence, preferably into a translatable mRNA. Regulatory elements ensuring expression in plant cells, animal cells and fungi as well as in bacteria, are well known to those skilled in the art. They encompass promoters, enhancers, termination signals, targeting signals and the like. Examples are given further below in connection with detailed explanations concerning the vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vector according to the present invention can be introduced into a (micro)organism so as to be expressed and to lead to the production of a protein is are capable of converting O-phospho-L-homoserine and methanethiol into L-methionine An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance *E. coli, S. cerevisiae*) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to a host cell which contains/is transformed with a nucleic acid molecule or a vector according to the present invention. In a preferred embodiment such a host cell expresses a protein according to the present invention and is able of converting O-phospho-L-homoserine and methanethiol into L-methionine. In principle, the host cell can be any conceivable host cell, e.g. an animal cell, a plant cell, a fungal cell or a bacterial cell. In a preferred embodiment the host cell is a bacterial cell or a fungal cell. In a particularly preferred embodiment the host cell is a bacterial cell, e.g. of the genus *Escherichia, Corynebacterium, Clostridium, Bacillus* or *Acinetobacter*, more preferably of the species *E. coli, Corynebacterium glutamicum, Bacillus subtilis* or *Acinetobacter villandi*.

In another preferred embodiment the host cell is a fungal cell, e.g. of the genus *Saccharomyces, Candida, Ashbya, Kluyveromyces, Pichia, Yarrowia, Zygosaccharomyces, Aspergillus, Debaryomyces* or *Torulopsis*, more preferably of the species *S. cerevisiae, Saccharomyces maximus, Candida maltosa, Ashbya gossypii, Kluveromyces lactis, Pichia pastoris Pichia stipitis, Yarrowia lipolitica, Aspergillus niger, Aspergillus nidullans, Debaryomyces hansenii* or *Torulopsis utilis* In a particularly preferred embodiment, the host cell is a yeast cell.

As stated above, the present invention also relates to a method for preparing a nucleic acid molecule encoding a protein which is capable of converting O-phospho-L-homoserine and methanethiol into L-methionine. Such a method comprises the following steps:
 (i) effecting mutations in a nucleic acid molecule encoding a cystathionine gamma synthase (EC 2.5.1.48) so as to produce mutated cystathionine gamma synthases;
 (ii) expressing the mutated nucleic acid molecules obtained in step (i) in a host cell and under culture conditions which allow for the selection of nucleic acid molecules which encode a protein which is able to enzymatically convert O-phospho-L-homoserine and methanethiol into L-methionine;
 (iii) identifying those host cells which express a protein which is able to enzymatically convert O-phospho-L-homoserine and methanethiol into L-methionine; and
 (iv) obtaining from a host cell identified in step (iii) the nucleic acid molecule encoding the mutated cystathionine gamma synthase which is able to enzymatically convert O-phospho-L-homoserine and methanethiol into L-methionine.

The present invention also relates to a method for preparing a protein which is able to enzymatically convert O-phospho-L-homoserine and methanethiol into L-methionine said method comprising the step of expressing a nucleic acid molecule obtained according to the above described method according to the invention and recovering the encoded protein.

The term "cystathionine gamma synthase (EC 2.5.1.48)" refers to any enzyme which has the enzymatic activity of a cystathionine gamma synthase. A cystathionine gamma synthase is an enzyme which catalyzes the following reaction

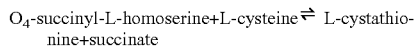
O$_4$-succinyl-L-homoserine+L-cysteine ⇌ L-cystathionine+succinate

This activity can be measured by methods known in the art (Ravanel, Biochem. J. 331 (1998), 639-648).

According to step (i) of the above described method according to the invention, a mutated version of a nucleic acid molecule encoding a cystathionine gamma synthase is prepared so as to produce a mutated cystathionine gamma synthase. Methods for mutagenizing nucleic acid molecules are well known to the person skilled in the art. Thus, it is possible to insert different types of mutations into the nucleic acid molecules by methods commonly used in molecular biology (see for instance Sambrook and Russell (2001), Molecular Cloning: A Laboratory Manual, CSH Press, Cold Spring Harbor, N.Y., USA), leading to the synthesis of a cystathionine gamma synthase with a modified amino acid sequence in comparison to the starting sequence. In principle, any type of mutation on the nucleic acid molecule level is conceivable such as deletions, additions and/or substitutions. In a preferred embodiment the mutation effected in the nucleic acid leads to a substitution of an amino acid on the amino acid sequence level.

It is possible to effect only one mutation per nucleic acid molecule, but it is of course also possible to effect one or more mutations in the nucleic acid molecule leading to one or more mutations on the amino acid level. There is in principle no upper limit to the number of mutations. However, it is preferable that the mutated nucleic acid molecule has at least still 60% sequence identity, more preferably at least 70% sequence identity, even more preferably at least 80% sequence identity, particularly preferred at least 90% sequence identity and most preferably at least 95% sequence identity to the starting sequence encoding a cystathionine gamma synthase used in step (i) of the above described method.

In a preferred embodiment the mutagenized nucleic acid molecule obtained in step (i) of the method encodes mutated version of the cystathionine gamma synthase which shows not more than 20 changes in amino acid residues in comparison to the cystathionine gamma synthase encoded by the starting nucleic acid molecule, ore preferably not more than 15 changes, even more preferably not more than 10 changes and particularly preferred not more than 5 changes.

The term "a nucleic acid molecule encoding a cystathionine gamma synthase (EC 2.5.1.48)" in step (i) of the method according to the invention refers to a nucleic acid molecule which encodes a protein having the enzymatic activity of a cystathionine gamma synthase as specified above. In principle, any nucleic acid molecule encoding such an enzyme can be employed in the method according to the invention as a starting material. Cystathionine gamma synthases have been described in detail above, as well as their occurrence in nature. Any nucleic acid encoding any of these cystathionine gamma synthases can be used in step (i) of the method according to the invention. In a preferred embodiment, the nucleic acid molecule used in step (i) is a nucleic acid molecule encoding a plant cystathionine gamma synthase. Even more preferably, the cystathionine gamma synthase is from *A. thaliana*, preferably a nucleotide sequence encoding the *A. thaliana* cystathionine gamma synthase as shown in SEQ ID NO: 1.

The nucleotide sequence of the nucleic acid molecule employed in step (i) may be adapted for use in the host cell which is employed in step (ii). For example, it is possible to change the codon usage so as to correspond more closely to the codon usage of the translation machinery of the employed host cells. Thus, the nucleic acid molecule may be modified so as to show an optimized codon usage in relation to the host cell employed in step (ii).

Moreover, other modifications may be necessary or desirable in order to adapt a certain nucleic acid molecule, such as a nucleic acid molecule encoding a plant cystathionine gamma synthase for the method according to the invention. For example, plant cystathionine gamma synthases usually contain a chloroplast targeting sequence at the amino terminal end which directs the protein to the chloroplasts. Depending on which host cell is employed in step (ii), it may be necessary or desirable to remove this target sequence. If, for example, yeast cells are used in step (i) it is desirable to remove this chloroplast target sequence. In addition, plant cystathionine gamma synthases may contain a regulatory region (also referred to as mto region) which allows for translational regulation mediated by the increase of the plant's intracellular pool of S-adenosylmethionine (SAM). SAM is capable of binding to the nascent cystathionine gamma synthase peptide during translation in a pocket which is formed by this mto region and a part of the ribosome thereby leading to an arrest of translation. It may be desirable to avoid this regulation when practicing the method according to the invention. Therefore, in a preferred embodiment, in step (i) a plant cystathionine gammy synthase encoding sequence is used which is modified so as to avoid the regulation by SAM. Such mutations have been described in the prior art, e.g. in Onoue al. (Journal of Biological Chemistry 286 (2011), 14903-14911). In addition, it may also be possible to use as a starting nucleic acid molecule a sequence which leads to a more stable version of the cystathionine gamma synthase. The identity of the second N terminal amino acid is known to determine the whole protein stability (Varshavsky, Annual Review of Biochemistry 81 (2012), 167-176). Thus, it is advantageous to avoid destabilizing residues (in particular Tyr, Gin, Leu, Phe, Asp, Lys, Arg) and to prefer stabilizing residues such as Val or Ser (Varshavsky, Annual review of Biochemistry 81 (2012), 167-176).

The expression of the mutated nucleic acid molecule according to step (ii) of the method can be achieved by methods known to a person skilled in the art. Expression systems have also already been described above in connection with the vectors and host cells according to the invention.

In step (ii) of the method according to the invention a host cell is employed for expressing the mutated cystathionine gamma synthase which allows for the selection of nucleic acid molecules which encode a protein which is able to enzymatically convert O-phospho-L-homoserine and methanethiol into L-methionine. In this context, it is for example possible to use host cells which can only survive when grown on a medium containing as the sole sulfur source methanethiol if they are able to convert O-phospho-L-homoserine and methanethiol into L-methionine. One example for such host cells are *Saccharomyces cerevisiae* cells which have been genetically modified to be at least devoid of the function of the met2. The MET2 gene codes for homoserine trans-acetylase which catalyzes the conversion of homoserine and acetyl-CoA to O-acetyl homoserine and CoA. Inactivation of the MET2 gene results in yeast strains displaying a methionine auxotrophy phenotype. Preferably, also the met6 gene should be rendered dysfunctional in such a yeast strain which is devoid of the MET2 function. The MET6 gene codes for homocysteine methyl-transferase which converts homocysteine and methyltetrahydrofolate into methionine. Since *S. cerevisiae* does not have any other way than synthesizing the essential amino acid methionine from homocysteine, an *S. cerevisiae* strain being devoid of the MET2 function (and optionally also the MET6 function) can only survive if it can produce methionine by other means.

The culture conditions in step (ii) are also adapted in such a way that the host cell is only able to survive if it is able of O-phospho-L-homoserine and methanethiol into L-methionine. This may be achieved by providing methanethiol as the sole sulfur source in the culture medium.

It is even more preferable that in addition to the MET2 and the MET6 genes also the THR4 gene is inactivated. This inactivation aims at increasing the intracellular pool of OPHS. In this case the transformed host cells are grown in a medium supplemented with both threonine and methanethiol in place of methionine. If such a host cell is used, it is possible to isolate mutants which only show a very faint activity of OPHS dependent methionine synthase.

Host cells identified in step (iii) of the method are then used to obtain nucleic acid molecules which encode the mutated cystathionine gamma synthase which is able to enzymatically convert O-phospho-L-homoserine and methanethiol into L-methionine. This can be done by methods known to the person skilled in the art.

The isolated nucleic acid molecule can then be used to express the corresponding enzyme or can be introduced into other host cells.

In a preferred embodiment, the method for preparing a nucleic acid molecule encoding a protein which is capable of converting O-phospho-L-homoserine and methanethiol into L-methionine comprises several rounds of screening, i.e. mutation and isolation of corresponding mutants showing the desired activity.

In this context it is preferred, that in a first round of screening a host cell is used in which the MET2, the MET6 and the THR4 genes are inactivated. As explained above, by using such a host cell, it is possible to isolate mutants which only show a very faint activity of OPHS dependent methionine synthase. Isolated mutants are then subjected to a further round of mutagenesis and are subsequently selected for OPHS dependent methionine synthase activity in a host cell in which only the MET2 and MET6 genes are inactivated but which have an active thr4 gene. Such a screen is more stringent as part of the OPHS is used by the threonine synthase. In this case the host cell used for selecting clones with the desired enzymatic property are grown in a medium supplemented with methanethiol as a sulfur source.

The second round of screening can be carried out iteratively and the selection pressure can be increased by decreasing the amount of methanethiol added to the medium and selecting for the transformed strains that display the fastest growth rate.

DESCRIPTION OF SEQUENCES

Figure 1:
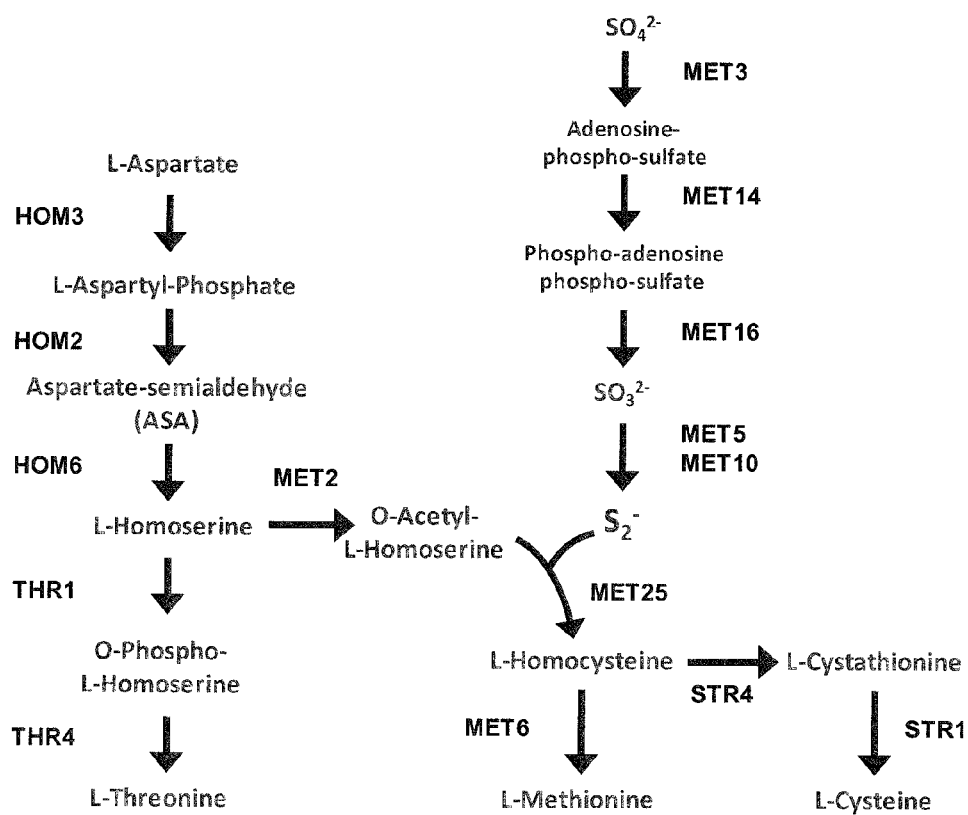
FIG. 1 shows a simplified view of the methionine biosynthesis pathway in *S. cerevisiae* (taken from: Thomas D. and Y. Surdin-Kerjan; Microbiological and Molecular Reviews 61 (1997); Metabolism of sulfur amino-acids in *Saccharomyces cerevisiae.*, page 503-532).
Figure 2:
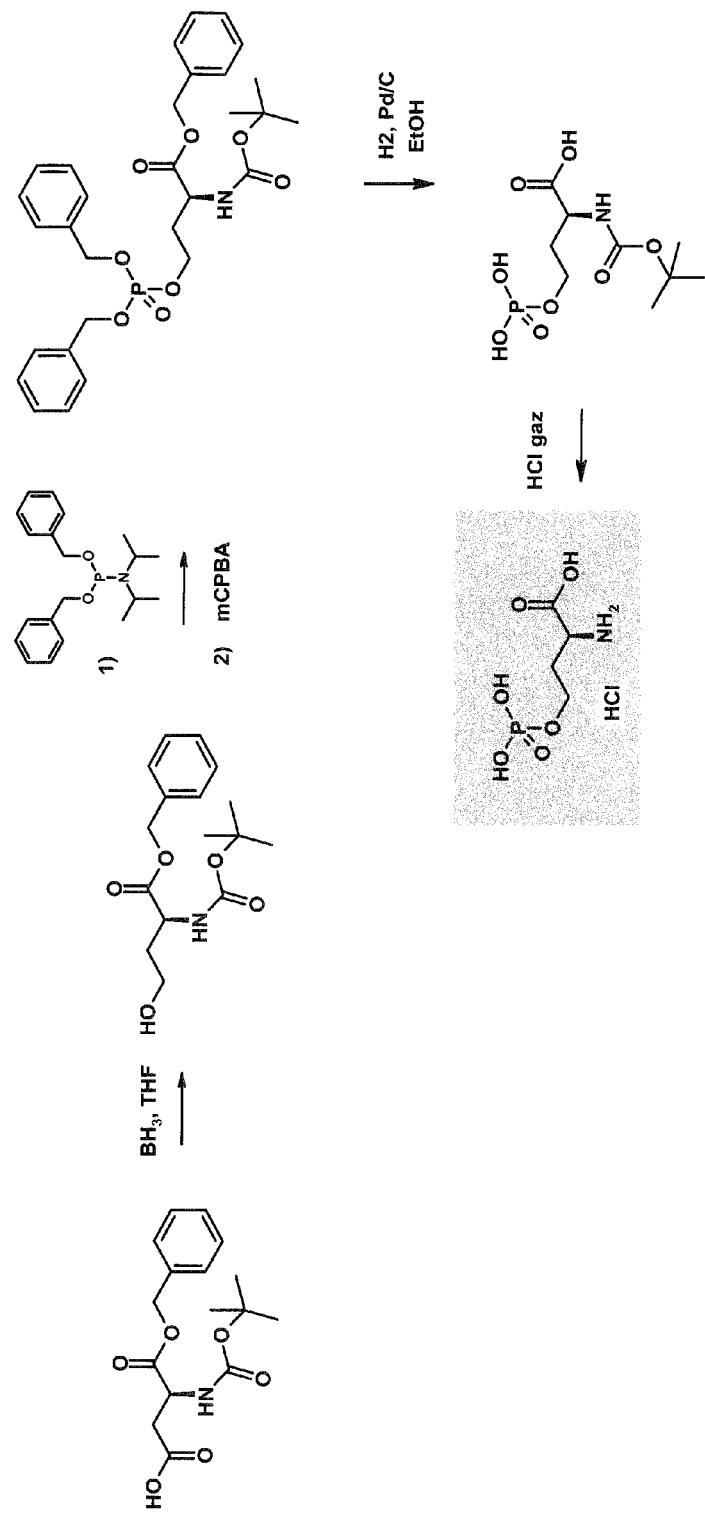
FIG. 2 shows a chemical pathway for the synthesis of O-phospho-L-homoserine.

SEQ ID NO: 1 shows the amino acid sequence of the cystathionine gamma synthase (EC 2.5.1.48) CGS1 from *Arabidopsis thaliana* (AAC25687.1).

SEQ ID NO: 2 shows the amino acid sequence of the cystathionine gamma synthase (EC 2.5.1.48) CGS1 from *Arabidopsis thaliana* (AAC25687.1) in which glycine 84 is replaced by serine. This sequence is also referred to as CGS1 G84S or CGS1-0.

SEQ ID NO: 3 shows the amino acid sequence of the cystathionine gamma synthase (EC 2.5.1.48) CGS1 from *Arabidopsis thaliana* (AAC25687.1) in which glycine 84 is replaced by serine and in which the N-terminal 57 amino acids have been removed and a methionine residue is added at the N-terminus. This sequence is also referred to as CGS1 1-4 G84S.

SEQ ID NO: 4 shows a truncated form the amino acid sequence of the cystathionine gamma synthase (EC 2.5.1.48) CGS1 from *Arabidopsis thaliana* (AAC25687.1) in which the N-terminal 88 amino acids have been removed and a methionine residue is added at the N-terminus. This sequence is also referred to as CGS1 1-5 G84S.

SEQ ID NO: 5 shows a truncated form the amino acid sequence of the cystathionine gamma synthase (EC 2.5.1.48) CGS1 from *Arabidopsis thaliana* (AAC25687.1) in which the N-terminal 160 amino acids have been removed and a methionine residue is added at the N-terminus. This sequence is also referred to as CGS1 1-1 G84S.

SEQ ID NO: 6 shows the sequence of the mutant MUT02.
SEQ ID NO: 7 shows the sequence of the mutant MUT04.
SEQ ID NO: 8 shows the sequence of the mutant MUT13.
SEQ ID NO: 9 shows the sequence of the mutant MUT18.
SEQ ID NO: 10 shows the sequence of the mutant MUT19.
SEQ ID NO: 11 shows the sequence of the mutant AD309.
SEQ ID NO: 12 shows the sequence of the mutant AD310.
SEQ ID NO: 13 shows the sequence of the mutant AD311.
SEQ ID NO: 14 shows the sequence of the mutant AD312.
SEQ ID NO: 15 shows the sequence of the mutant AD313.
SEQ ID NO: 16 shows the sequence of the mutant AD242.
SEQ ID NO: 17 shows the sequence of the mutant AD328.

SEQ ID NO: 18 shows the sequence of the mutant AD329.
SEQ ID NO: 19 shows the sequence of the mutant MUT24.
SEQ ID NO: 20 shows the sequence of the mutant MUT27.
SEQ ID NO: 21 shows the sequence of the mutant MUT67.
SEQ ID NO: 22 shows the sequence of the mutant MUT68.
SEQ ID NO: 23 shows the sequence of the mutant MUT70.
SEQ ID NO: 24 shows the sequence of the mutant MUT71.
SEQ ID NO: 25 shows the sequence of the mutant MUT72.
SEQ ID NO: 26 shows the sequence of the mutant MUT74.
SEQ ID NO: 27 shows the sequence of the mutant MUT75.
SEQ ID NO: 28 shows the sequence of the mutant MUT78.
SEQ ID NO: 29 shows the sequence of the mutant MUT79.

The content of documents cited herein is herewith incorporated by reference in its entirety.

Other aspects and advantages of the invention will be described in the following examples, which are given for purposes of illustration and not by way of limitation.

EXAMPLES

Example 1: Preparation of Truncated Forms of CGS1 Used as Starting Material for Preparing Mutants The CGS1-4 gene is a synthetic gene. The synthesis was performed by Eurofins MWG Operon, (Ebersberg) using the GENEius algorithm in order to optimize the codon usage for improving its expression in *S. cerevisiae*. The *S. cerevisiae* codon usage table used was taken from the Kazusa Codon Usage Database (http://www.kazusa.or.jp/codon). The truncated forms CGS1-5 and CGS1-1 have been prepared by PCR using CGS1-4 as a matrix, with forward oligonucleotides GTACCGCTCGAG ATGGTTGCTGGTAAGTGGTCTAACAATC for CGS1-5 and GTACCGCTCGAG ATGTCTGTTCAATTGACCGATTCTAAG for CGS1-1. For both the CGS1-5 and CGS1-1 forms, an identical reverse oligonucleotide AGTACGGGATCC TCAAATGGCTTCCA was used.

Figure 3:
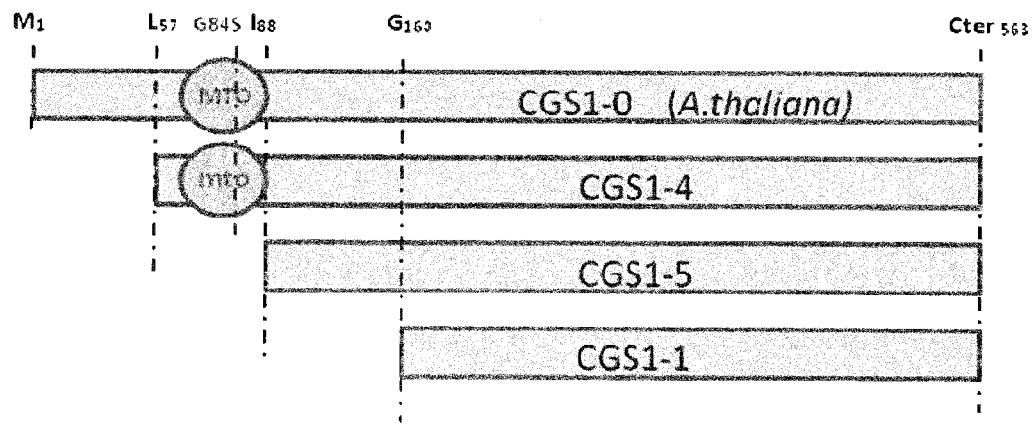
FIG. 3 shows a schematic representation of the truncated forms of CGS1 used as starting material for creating mutated versions of the enzyme.

The described truncated modified forms of CGS1 are schematically shown in FIG. 3.

Example 2: Preparation of Mutants of the Truncated Forms of CGS1

Truncated forms of the CGS1 genes were cloned into the pAL06 plasmid, a yeast replicative vector derived from the pRS316 vector (Sikorski R S & Hieter P., Genetics. 1989, 122:19-27). The pAL06 plasmid allows the expression of the cloned gene under the control of the strong yeast promoter TEF1. The CGS1 libraries were generated by hypermutagenic PCR with biased deoxynucleotide triphosphate (dNTP) concentrations using the protocol described by Vartanian J P et al., (Nucleic Acids Res. 1996 24:2627-2631). Both a [dTTP]>[dCTP] and a [dGTP]>[dATP] biases were used during the mutagenic PCRs. Either [dTTP]/[dCTP]=[dGTP]/[dATP]=1000 µM/200 µM or [dTTP]/[dCTP]=[dGTP]/[dATP]=1000 µM/150 µM were used in the presence of 0.5 mM MnCl$_2$.

Example 3: Screening for Mutants which can Produce L-Methionine from O-Phospho-L-Homoserine and Methanethiol CGS1 libraries were transformed in yeast strains YA247-5A (MAT-α, ade2, his3, leu2, met2::loxP, met6::HIS3, trp1, ura3) or YA246-4A (MAT-α, ade2, his3, leu2, met2::loxP, met6::HIS3, thr4::loxP, trp1, ura3) in minimal medium supplemented with methionine but lacking uracil to select for the plasmid marker. After 48 hours of grow, cells were collected, washed and re-suspended in minimal liquid medium with methylmercaptan as a source of sulphur. After 7 days, cultures were collected and diluted within the same liquid medium, to an OD$_{600nm}$ of about 0.2. Three successive dilutions cycles were performed.

The plasmids present within the resulting growing yeast cells were then extracted, amplified into *E. coli* and the resulting DNA was used to re-transformed the strains YA247-5A (MAT-α, ade2, his3, leu2, met2::loxP, met6::HIS3, trp1, ura3) or YA246-4A (MAT-a, ade2, his3, leu2, met2::loxP, met6::HIS3, thr4::loxP, trp1, ura3). The transformed yeasts were then selected on solid minimal medium containing methionine but lacking uracil. The capacity of each individual colony to grow with methylmercaptan as a sulphur source was then evaluated by growing individual clones in liquid medium containing methanethiol as a sulfur source. At each evolution cycle, plasmids contained within the yeast colonies displaying the best growth rates in the presence of methanethiol were extracted and sequenced. The selected mutants were transformed in YA247-5A strain for in vitro analysis and used as a starting materials for a new hypermutagenic PCR.

Using the above described screening procedure a large number of mutants of CSG1 have been identified which were able to grow on methanethiol as the sole sulfur source and which are therefore assumed to be able to convert O-phospho-L-homoserine and methanethiol into L-methionine. Of these mutants the sequences have been determined and the mutants are summarized in the following Table 1A wherein the positions of the mutations are indicated with reference to the sequence provided in SEQ ID NO: 3 (CGS 1-4). The mutants are also summarized in FIG. 7 in which they are aligned.

TABLE 1A

| Amino acid | Position | Mutation(s) |
|---|---|---|
| P | 10 | L |
| N | 11 | D |
| Q | 15 | R |
| I | 27 | S |
| A | 30 | T |
| L | 45 | S |
| S | 47 | T |
| V | 60 | D |
| A | 68 | T |
| F | 150 | L |
| T | 178 | I |
| D | 183 | E |
| I | 185 | V |
| T | 220 | S |
| M | 232 | L |
| V | 245 | A |
| A | 257 | T |
| N | 259 | D, S |
| F | 261 | S |
| F | 275 | L |
| I | 287 | V, F |
| H | 289 | Y, R |
| Y | 324 | F |
| G | 326 | S |
| P | 356 | T |
| T | 371 | A |
| V | 396 | A |
| P | 405 | S |
| D | 431 | G |
| I | 436 | T |
| I | 457 | L |
| D | 459 | N |

TABLE 1A-continued

| Amino acid | Position | Mutation(s) |
|---|---|---|
| P | 470 | S |
| E | 472 | G |
| A | 506 | G |
| I | 507 | V |

The following Table 1B lists all the mutants analysed and indicated the positions of the found mutations with respect to the full length sequence of SEQ ID NO:1 (CGS1). The position with respect to the corresponding starting sequence is indicated in parenthesis.

TABLE 1B

| Mutant | Mutations | Starting sequence |
|---|---|---|
| MUT02 | P412(356)T | 1-4 |
| MUT04 | P66(10)L, I83(27)S, V116(60)D, Y380(324)F, I513(457)L | 1-4 |
| MUT13 | M57(1)K, I88(32)M, I343(287)V, H345(289)R, P412(356)T, stop564(508)W | 1-4 |
| MUT18 | P66(10)L, M288(232)L, V301(245)A, N315(259)D, P412(356)T, D487(431)G, I492(436)T | 1-4 |
| MUT19 | N67(11)D, Q71(15)R, A86(30)T, L101(45)S, S103(47)T, A124(68)T, T234(178)I, P412(356)T, T427(371)A, D515(459)N | 1-4 |
| AD309 | I88(1)M, P412(325)T | 1-5 |
| AD310 | I88(1)M, V116(29)D, Y380(293)F, I513(426)L | 1-5 |
| AD311 | I88(1)M, I343(256)V, H345(258)R, P412(325)T | 1-5 |
| AD312 | I88(1)M, M288(201)L, V301(214)A, N315(228)D, P412(325)T, D487(400)G, I492(405)T | 1-5 |
| AD313 | I88(1)M, L101(14)S, S103(16)T, A124(37)T, T234(147)I, P412(325)T, T427(340)A, D515(428)N | 1-5 |
| AD242 | G160(1)M, P412(325)T | 1-1 |
| AD328 | G160(1)M, M288(129)L, V301(142)A, N315(156)D, P412(253)T, D487(328)G, I492(333)T | 1-1 |
| AD329 | G160(1)M, T234(75)I, P412(253)T, T427(268)A, D515(356)N | 1-1 |
| MUT24 | G160(1)M, F206(47)L, A313(154)T, N315(156)S, F317(158)S, F331(172)L, H345(186)Y, P412(253)T, A562(403)G | 1-1 |
| MUT27 | G160(1)M, I241(82)V, P412(253)T, P461(302)S | 1-1 |
| MUT67 | G160(1)M, F331(172)L, P412(253)T, V452(293)A, E528(369)G | 1-1 |
| MUT68 | G160(1)M, F331(172)L, G382(223)S, P412(253)T, V452(293)A | 1-1 |
| MUT70 | G160(1)M, T276(117)S, F331(172)L, P412(253)T, V452(293)A | 1-1 |
| MUT71 | G160(1)M, D239(80)E, F331(172)L, P412(253)T, V452(293)A, I563(404)V | 1-1 |
| MUT72 | G160(1)M, F331(172)L, I343(184)F, P412(253)T, V452(293)A, I563(404)V | 1-1 |
| MUT74 | G160(1)M, F331(172)L, P412(253)T, V452(293)A, P526(367)S | 1-1 |
| MUT75 | G160(1)M, F331(172)L, P412(253)T, I563(404)V | 1-1 |
| MUT78 | G160(1)M, F331(172)L, P412(253)T, V452(293)A | 1-1 |
| MUT79 | G160(1)M, F331(172)L, I343(184)F, P412(253)T | 1-1 |

Starting sequence 1-4 corresponds to SEQ ID NO: 3
Starting sequence 1-5 corresponds to SEQ ID NO: 4
Starting sequence 1-1 corresponds to SEQ ID NO: 5

The following Table 1C lists all the mutants analysed and indicates the positions of the found mutations with respect to the sequence of SEQ ID NO:3 (CGS1-4). The position with respect to the corresponding starting sequence is indicated in parenthesis.

TABLE 1C

| Mutant | Mutations | Starting sequence |
|---|---|---|
| MUT02 | P356T | 1-4 |
| MUT04 | P10L, I27S, V60D, Y324F, I457L | 1-4 |
| MUT13 | M1K, I32M, I287V, H289R, P356T, stop508W | 1-4 |
| MUT18 | P10L, M232L, V245A, N259D, P356T, D431G, I436T | 1-4 |
| MUT19 | N11D, Q15R, A30T, L45S, S47T, A68T, T178I, P356T, T371A, D459N | 1-4 |
| AD309 | I32(1)M, P356(325)T | 1-5 |
| AD310 | I32(1)M, V60(29)D, Y324(293)F, I457(426)L | 1-5 |
| AD311 | I32(1)M, I287(256)V, H289(258)R, P356(325)T | 1-5 |
| AD312 | I32(1)M, M232(201)L, V245(214)A, N259(228)D, P356(325)T, D431(400)G, I436(405)T | 1-5 |
| AD313 | I32(1)M, L45(14)S, S47(16)T, A68(37)T, T178(147)I, P356(325)T, T371(340)A, D459(428)N | 1-5 |
| AD242 | G104(1)M, P356(253)T | 1-1 |
| AD328 | G104(1)M, M232(129)L, V245(142)A, N259(156)D, P356(253)T, D431(328)G, I436(333)T | 1-1 |
| AD329 | G104(1)M, T178(75)I, P356(253)T, T371(268)A, D459(356)N | 1-1 |
| MUT24 | G104(1)M, F150(47)L, A257(154)T, N259(156)D, F261(158)S, F275(172)L, H289(186)Y, P356(253)T, A506(403)G | 1-1 |
| MUT27 | G104(1)M, I185(82)V, P356(253)T, P405(302)S | 1-1 |
| MUT67 | G104(1)M, F275(172)L, P356(253)T, V396(293)A, E472(369)G | 1-1 |
| MUT68 | G104(1)M, F275(172)L, G326(223)S, P356(253)T, V396(293)A | 1-1 |
| MUT70 | G104(1)M, T220(117)S, F275(172)L, P356(253)T, V396(293)A | 1-1 |
| MUT71 | G104(1)M, D183(80)E, F275(172)L, P356(253)T, V396(293)A, I507(404)V | 1-1 |
| MUT72 | G104(1)M, F275(172)L, I287(184)F, P356(253)T, V396(293)A, I507(404)V | 1-1 |
| MUT74 | G104(1)M, F275(172)L, P356(253)T, V396(293)A, P470(367)S | 1-1 |
| MUT75 | G104(1)M, F275(172)L, P356(253)T, I507(404)V | 1-1 |
| MUT78 | G104(1)M, F275(172)L, P356(253)T, V396(293)A | 1-1 |
| MUT79 | G104(1)M, F275(172)L, I287(184)F, P356(253)T | 1-1 |

Example 4: Test of the Enzymatic Activity in Yeast *Saccharomyces cerevisiae*

Expression of any of the above described mutants in *Saccharomyces cerevisiae* strains YA247-5A (MAT-α, ade2, his3, leu2, met2::loxP, met6::HIS3, trp1, ura3) and YA246-4A (MAT-α, ade2, his3, leu2, met2::loxP, met6::HIS3, thr4::loxP, trp1, ura3) relieve the strains from their methionine auxotrophy.

In other words upon expression of any of the above mutants, yeast strain YA247-5A and YA246-4A defective for methionine synthesis grow on a minimal medium supplemented with adenine, histidine, leucine, tryptophane and uracil.

Experimental Design of the Test:

Mutant nucleotide sequences were individually cloned into the replicative plasmide pAL06 (a derivative of pRS316) downstream of a transcription promoter (pTEF1) and upstream of a transcription terminator (tADH1).

The twelve plasmids thus obtained were individually transformed in yeast strains YA247-5A and YA246-4A. Transformants were grown in medium A (Difco™ Yeast Nitrogen Base 6.7%, glucose 2%, adenine 0.3 mM, leucine 0.75 mM, Histidine 1.3 mM, tryptophane 0.1 mM) supplemented with methionine 0.2 mM.

Each of the transformant was then inoculated ($OD_{590}$=0.015) in medium A supplemented with 0.05 mM methionine, or in medium A supplemented with methanethiol 0.1 or 1 mM.

Figure 4:
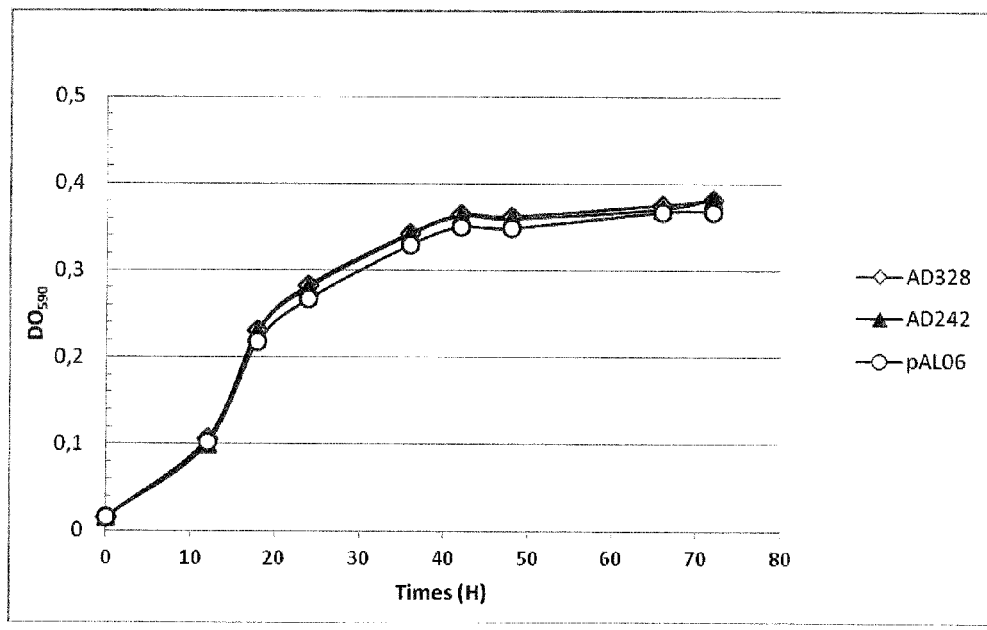
FIG. 4 shows growth of strains YA246-4A expressing either the AD242 or the AD328 CGS1 variant or carrying the control vector pAL06 in medium A supplemented with methionine 0.05 mM

The growth was monitored by following the Optical Density at 590 nm ($OD_{590}$). The respective growth of each clone in the two media was compared to the growth of the negative controls YA246-4A or YA247-5A transformed with an empty vector pAL06. In medium A with methionine, all strains tested have a generation time of about 4 h. For example, the growth of strains YA246-4A expressing the mutants CGS 1-4 (G84S), AD242 and AD328 and the control pAL06 vector is shown in FIG. 4.

Figure 5:
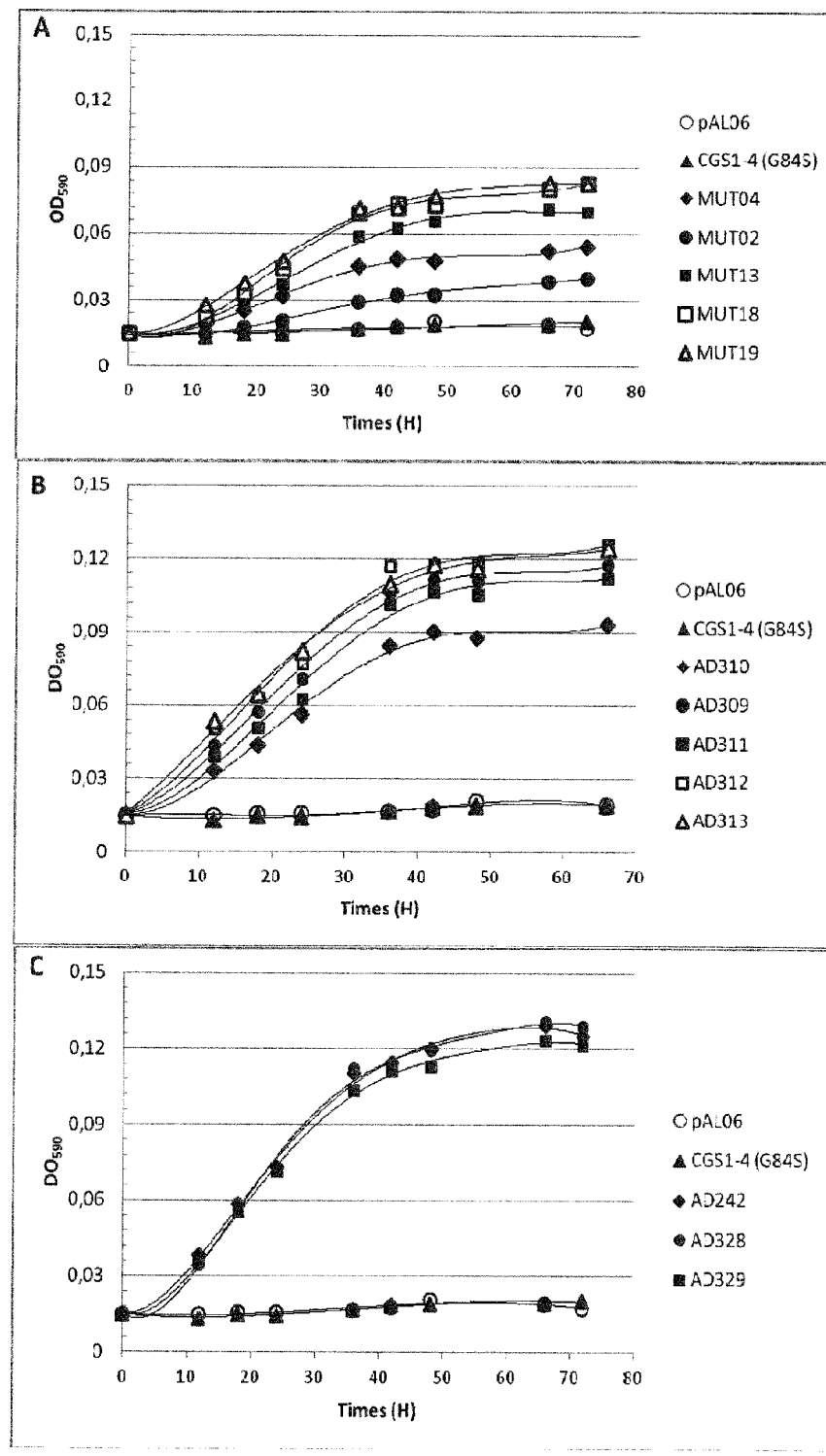
FIG. 5 shows the growth of strains based on YA246-4A expressing CGS1-4 (A), CGS1-5 (B) and CGS1-1 (C) mutant families respectively, in medium A supplemented with 0.1 mM of methanethiol. The CGS1-4 (G84S) and negative controls with pAL06 empty vector are shown in all graphs.

Growth in a Context of Accumulation of Phosphohomoserine:

The growth of strains based on YA246-4A which accumulate phosphohomoserine and express CGS1 protein mutants in medium A supplemented with 0.1 mM methanethiol is shown in FIG. 5.

In all cases, no growth was observed for the control CGS1-4 (G84S) and for the strains with pAL06 plasmid.

For the CGS1-4 family (FIG. 5A), the generation time is comprised between 13 h for MUT19 and 42 h for MUT02. For the CGS1-5 family (FIG. 5B), the generation time is comprised between 9.5 h for AD312 and AD313 and 12.5 h for AD310. For the CGS1-1 family (FIG. 5C), the generation time is about 9.5 h for AD242, AD328 and AD329.

Figure 6:
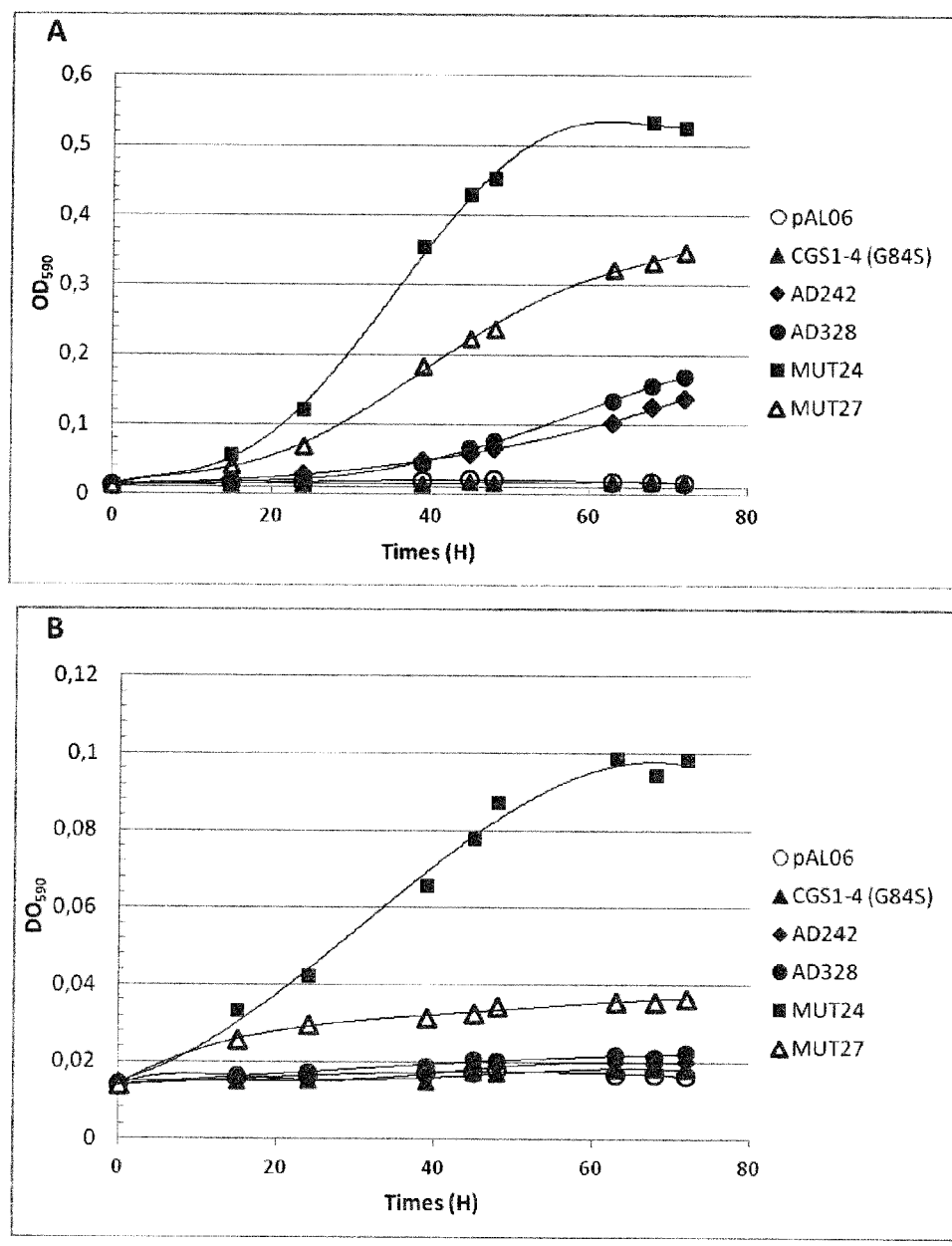
FIG. 6 shows the growth of strains based on YA247-5A expressing CGS1-4 mutants family AD242, AD328, MUT24, and MUT27 in medium A supplemented with 1 mM (A) or 0.1 mM (B) of methanethiol. The CGS1-4 (G84S) and negative controls with pAL06 are shown in all graphs.
Figure 7A:
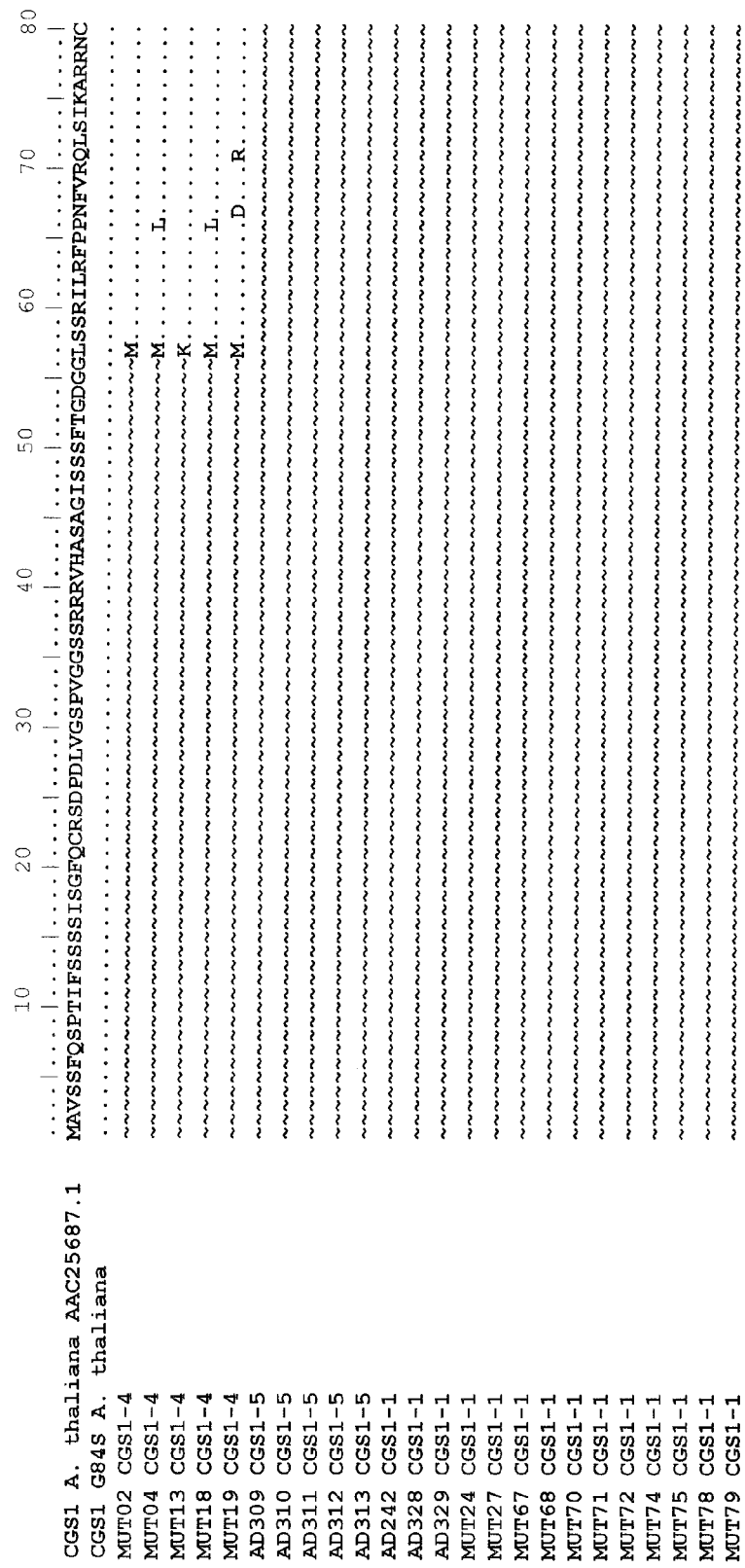
FIGS. 7A-7D show an alignment of the identified mutants of CGS1.
Figure 7A:
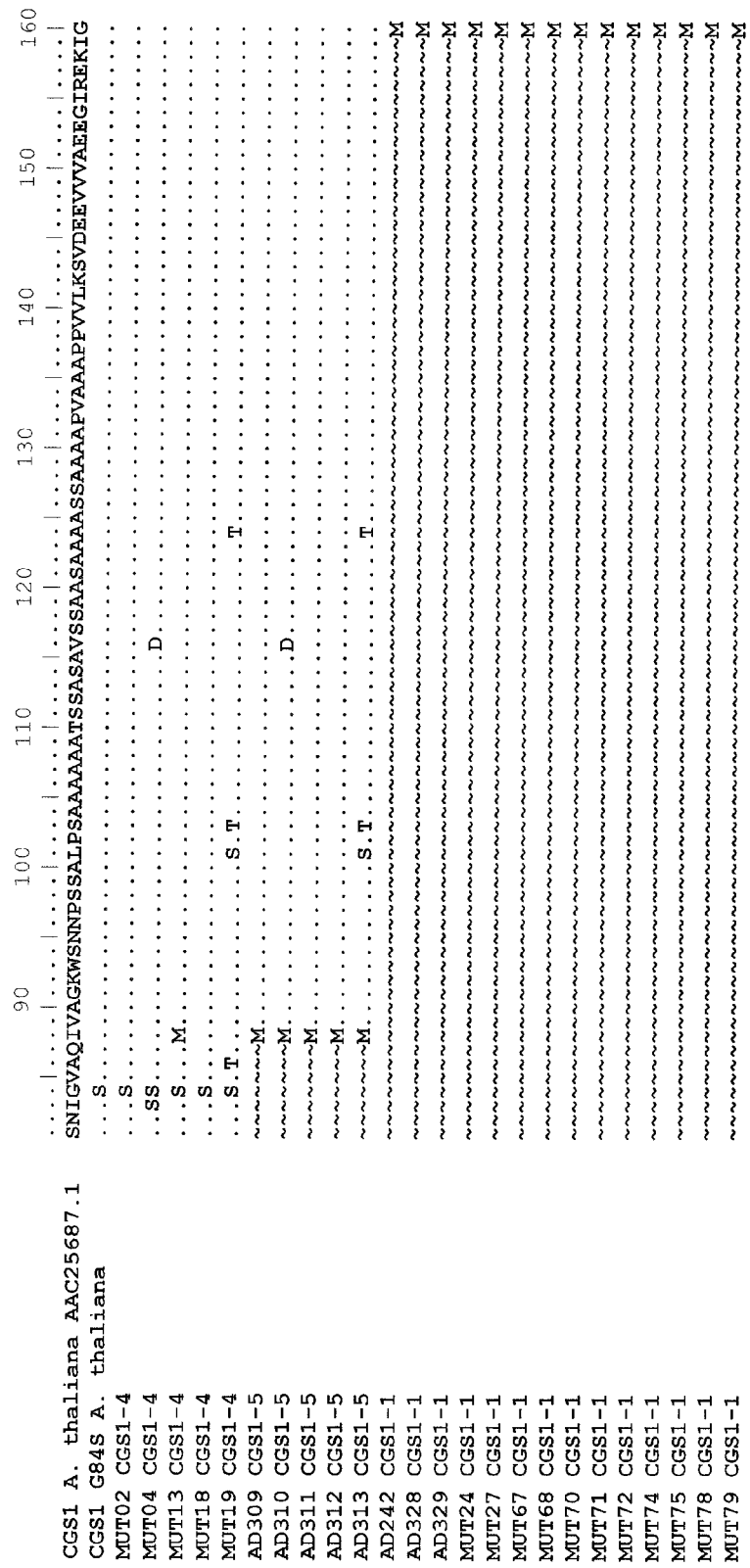
Figure 7B:
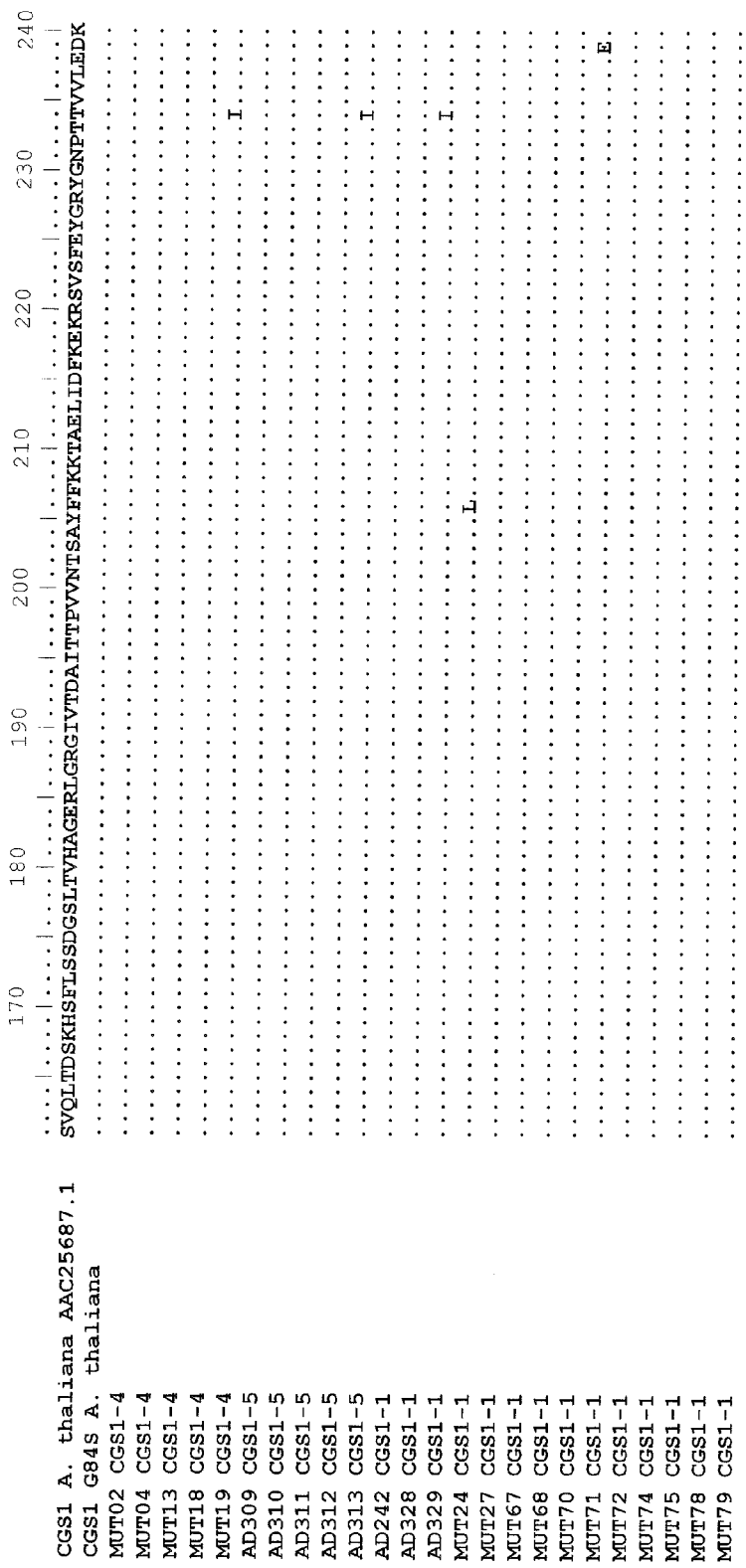
Figure 7C:
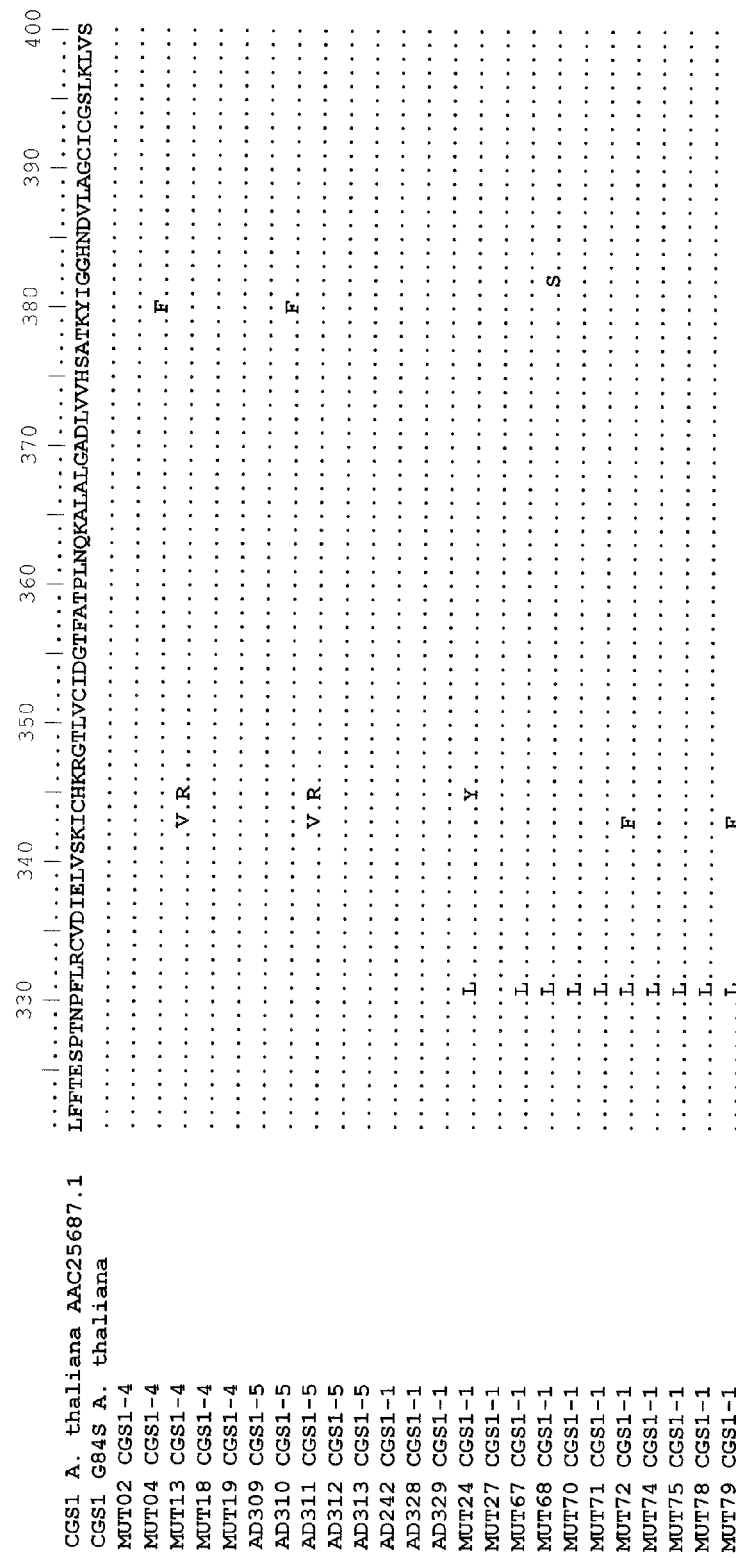
Figure 7C:
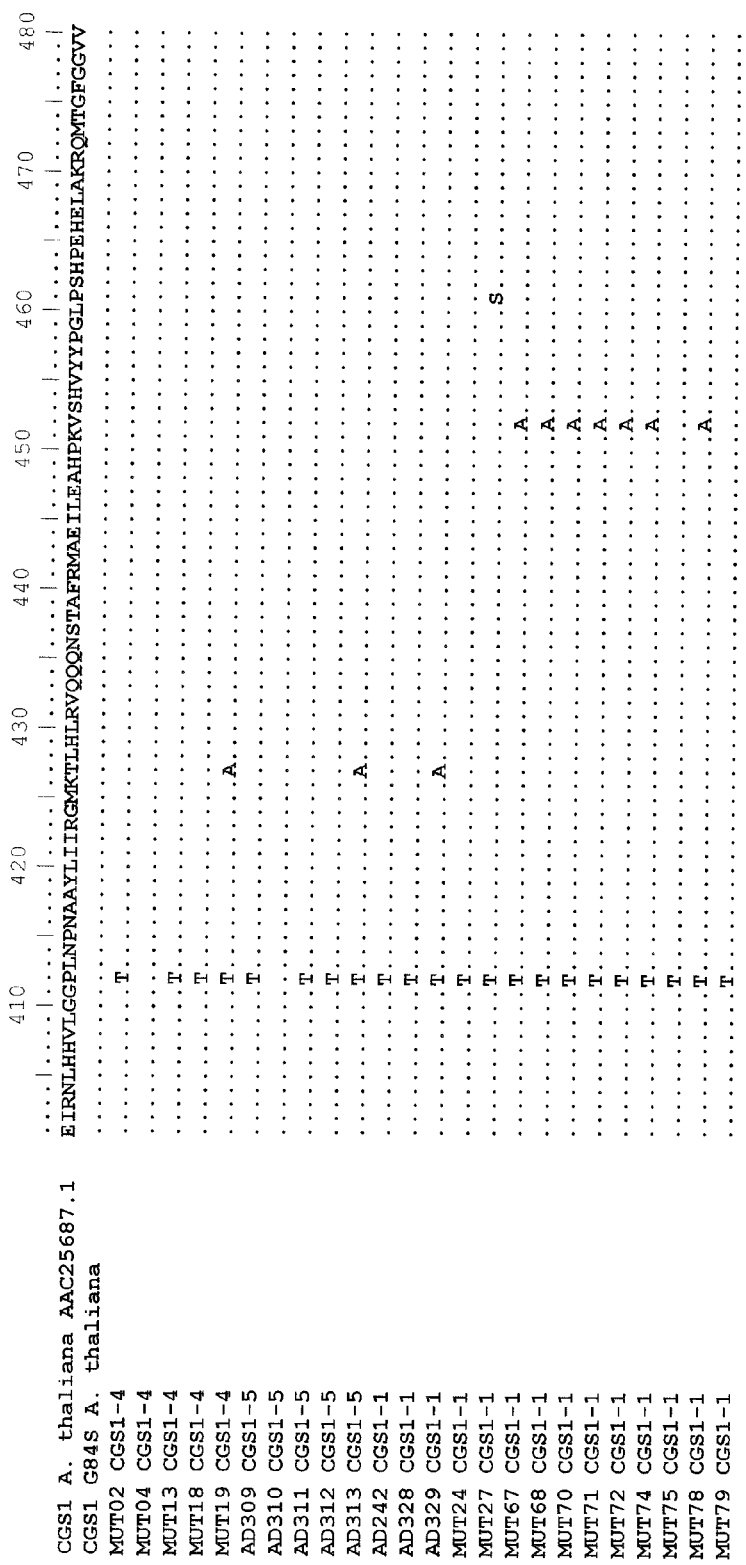
Figure 7D:
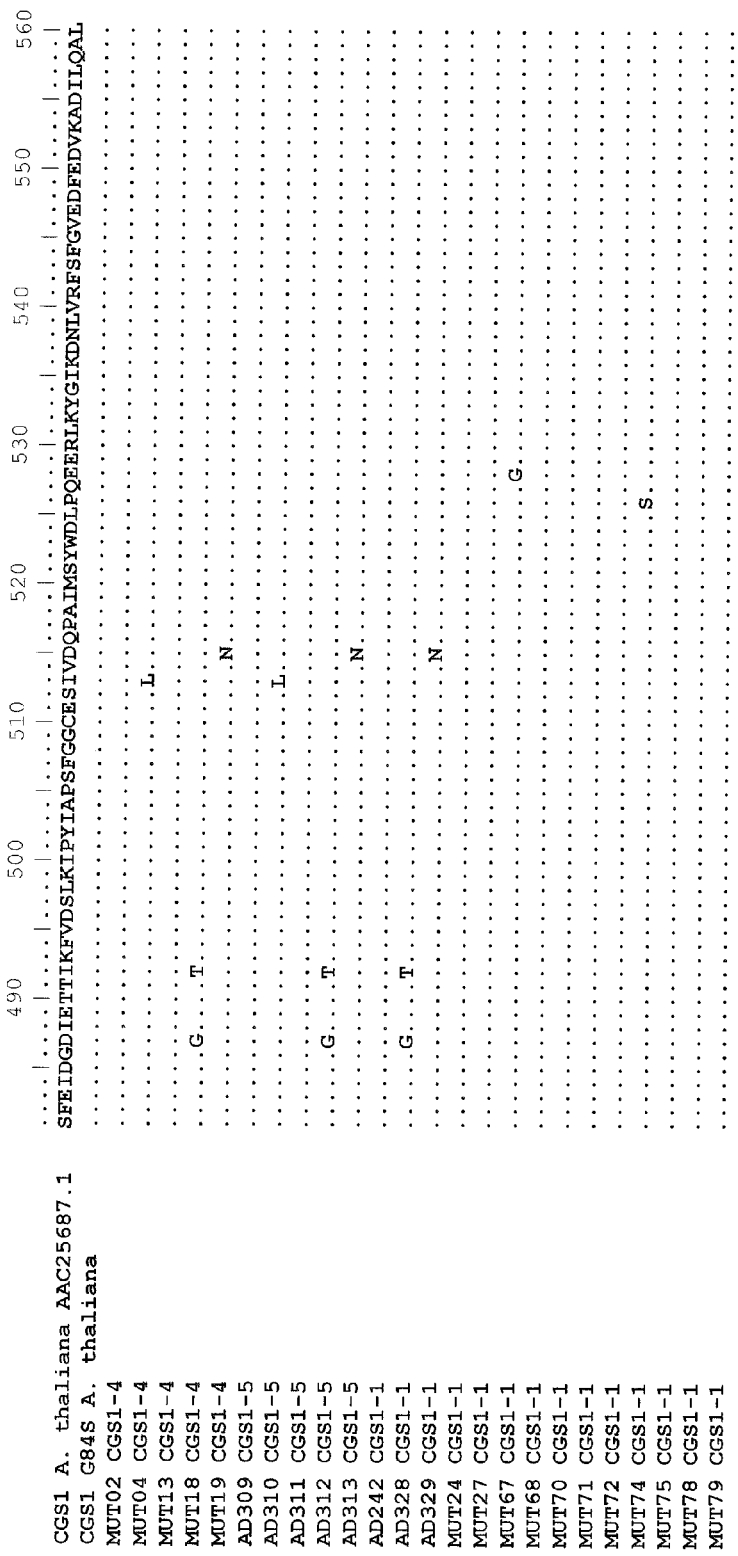

Growth in a Context without Accumulation of Phosphohomoserine:

The growth of strains based on YA247-5A which do not accumulate phosphohomoserine and express CGS1 protein mutants in medium A supplemented with 1 mM methanethiol or 0.1 mM methanethiol is shown in FIGS. 6A and 6B, respectively.

With 1 mM of methanethiol no growth is observed for the CGS1-1 and the negative control transformed with the pAL06 empty vector. The generation times are about 21 h for AD242 or AD328, 10.5 h for MUT27 and 8 h for MUT24. With 0.1 mM of methanethiol growth is observed only with MUT24 and MUT27 mutants. The generation times are respectively 19 h and 40 h.

Example 5: In Vitro Activity of OPHS Dependent Methionine Synthase

In vitro activity of the enzyme expressed in yeast was tested in a crude lysate of yeast.

The activity was followed by monitoring the synthesis of methionine in the lysate in the presence of O-phospho-L-homoserine (OPHS) and methanethiol ($CH_3SNa$). Lysates from yeast cells YA246-5A, YA246-5A carrying an empty plasmid pAL06, YA246-5A expressing CGS1-4 and YA246-5A expressing mutants AD246, AD239, MUT24, MUT27, MUT67 or MUT79 were compared.

Experimental Procedure:
Lysate Preparation

Yeast cells were first grown in a complete medium. This first culture was used to inoculate 100 ml of medium A ($OD_{590nm}$=0.3) that was incubated at 28° C. under agitation for 16 hours.

The total amount of protein was determined using a Bradford assay.

To start the reaction, 0.03 to 0.06 mg of total protein was incubated at 37° C. in 100 mM Tris pH8, 0.2 mM pyridoxal phosphate, 5 mM CH3SNa and 25 mM OPHS in a total volume of 100 µl for 15 minutes. 10 µl aliquots of the reaction mixture were collected at 15 and 60 minutes and the reaction was stopped by addition of 90 µl perchloric acid.

The amount of methionine in these aliquots was determined by LCMS using [13]CMet as internal standard. The amount of methionine formed was normalized by the amount of protein used in the assay.

The results are shown in the following Table 2:

TABLE 2

| | Activity (nmole · $min^{-1}$ · $mg^{-1}$) | St-Dev |
|---|---|---|
| CGS1-4 (G84S) | undetectable | — |
| pAD242 | 142 | ±13 |
| pAD329 | 143 | ±11 |
| pMUT24 | 354 | ±14 |
| pMUT27 | 343 | ±38 |
| pMUT67 | 864 | ±91 |
| pMUT79 | 462 | ±35 |

Example 6: In Vitro Assay for Measuring Homocysteine Synthase Activity

The homocysteine synthase activity of the enzymes expressed in yeast was tested in an in vitro assay using a crude lysate of yeast.

The activity was followed by monitoring the synthesis of methionine in the lysate in the presence of O-phospho-L-homoserine (OPHS) and methanethiol ($CH_3SNa$). Lysates from yeast cells YA246-5A, YA246-5A carrying an empty plasmid pAL06, YA246-5A expressing CGS1-4 and YA246-5A expressing mutants AD242, AD328, MUT24, MUT27, MUT67 or MUT79 were compared.

Experimental Procedure:
Lysate Preparation

Yeast cells were first grown in a complete medium. This first culture was used to inoculate 100 ml of medium A ($OD_{590nm}$=0.3) that was incubated at 28° C. under agitation for 16 hours. The total amount of protein was determined using a Bradford assay. The amount of homocysteine formed is determined by a colorimetric assay.

To start the reaction, 0.03 to 0.06 mg of total protein was incubated in 0.1M Tris ph8, 0.2 mM pyridoxal phosphate, 10 mM $Na_2S$, 12.5 mM OPHS in 100 µl. incubate 15 minutes at 30° C.

Add 500 µl of 1% $NaNO_2$ (dissolved in $H_2SO_4$ 0.4 N) incubate for 5 minutes

Add 100 µl of $NH_4SO_3NH_2$ incubate for 2 minutes

Add 750 µl of 1 volume de $HgCl_2$

Add 4 volumes of sulfanilamide

Add 2 volumes of N-(1-Naphthyl)ethylenediamine dihydrochloride incubate for 15 minutes read the OD at 450 nm (increase proportionally with the quantity of homocysteine—the amount is determined by comparison with the results obtained with a known range of homocysteine).

The results are shown in Table 3.

TABLE 3

| | Activity (nmole · $min^{-1}$ · $mg^{-1}$) | St. Dev |
|---|---|---|
| CGS1-4 (G84S) | undetectable | — |
| pAD242 | 18 | ±4 |
| pAD328 | 21 | ±2 |
| pMUT24 | 59 | ±9 |
| pMUT27 | 47 | ±2 |
| pMUT67 | 239 | ±32 |
| pMUT79 | 215 | ±29 |

The invention claimed is:

1. A method for producing L-methionine, comprising enzymatically converting O-phospho-L-homoserine (OPHS) and methanethiol into L-methionine and $H_3PO_4$ according to the following reaction scheme:

O-phospho-L-homoserine+$CH_3.SH$<=>L-methionine+$H_3PO_4$;

wherein
the enzymatic conversion is achieved by a OPHS dependent methionine synthase that is a protein derived from a cystathionine gamma synthase (EC 2.5.1.48) by mutation; and
the OPHS dependent methionine synthase is a protein selected from the group consisting of:
(a) a protein comprising the amino acid sequence as shown in any one of SEQ ID NOs: 6 to 29; and
(b) a protein having a sequence identity of at least 90% to any one of SEQ ID NOs: 6 to 29 and having the enzymatic activity of converting O-phospho-L-homoserine and methanethiol into L-methionine and $H_3PO_4$.

2. The method of claim 1, which is carried out in vitro.

3. The method of claim 1, wherein the method is carried out by making use of a microorganism producing the OPHS dependent methionine synthase.

4. A method comprising enzymatically converting O-phospho-L-homoserine and methanethiol into L-methionine and $H_3PO_4$ via a protein that is:
(I) a cystathionine γ synthase having the amino acid sequence shown in SEQ ID NO: 3 by substitution or deletion of at least one amino acid residue in SEQ ID NO: 3 selected from the group consisting of:
(a) proline 10;
(b) asparagine 11;
(c) glutamine 15;
(d) isoleucine 27;
(e) alanine 30;
(f) leucine 45;
(g) serine 47;
(h) valine 60;
(i) alanine 68;
(j) phenylalanine 150;
(k) threonine 178;
(l) aspartate 183;
(m) isoleucine 185;
(n) threonine 220;
(o) methionine 232;
(p) valine 245;
(q) alanine 257;
(r) asparagine 259;
(s) phenylalanine 261;
(t) phenylalanine 275;
(u) isoleucine 287;
(v) histidine 289;
(w) tyrosine 324;
(x) glycine 326;
(y) proline 356;
(z) threonine 371;
(aa) valine 396;
(bb) proline 405;
(cc) aspartate 431;
(dd) isoleucine 436;

(ee) isoleucine 457;
(ff) aspartate 459;
(gg) proline 470;
(hh) glutamate 472;
(ii) alanine 506; and
(jj) isoleucine 507;
or
(II) a cystathionine gamma synthase, the amino acid sequence of which has at least 90% sequence identity to the amino acid sequence shown in SEQ ID NO: 3, by substitution or deletion of at least one amino acid residue corresponding to any one of (a) to (jj) listed above in SEQ ID NO: 3;
or
(III) the cystathionine gamma synthase of (I) or (II) by deletion of one or more N-terminal amino acids corresponding to amino acids 1 to 103 of the amino acid sequence as shown in SEQ ID NO: 3, wherein substitution or deletion of at least one amino acid residue is present.

5. The method of claim 4, wherein said protein is selected from the group consisting of:
   (a) a protein comprising the amino acid sequence as shown in any one of SEQ ID NOs: 6 to 29; and
   (b) a protein having a sequence identity of at least 90% to any one of SEQ ID NOs: 6 to 29 and having the enzymatic activity of converting O-phospho-L-homoserine and methanethiol into L-methionine and $H_3PO_4$.

6. The method of claim 5, wherein said protein has a sequence identity of at least 90% to any one of SEQ ID NOs: 6 to 29 and has the enzymatic activity of converting O-phospho-L-homoserine and methanethiol into L-methionine and $H_3PO_4$.

7. A protein having the enzymatic activity of converting O-phospho-L-homoserine and methanethiol into L-methionine and $H_3PO_4$, wherein the protein is
   (I) a cystathionine gamma synthase having the amino acid sequence shown in SEQ ID NO: 3 by substitution or deletion of at least one amino acid residue in SEQ ID NO: 3 selected from the group consisting of:
   (a) proline 10;
   (b) asparagine 11;
   (c) glutamine 15;
   (d) isoleucine 27;
   (e) alanine 30;
   (f) leucine 45;
   (g) serine 47;
   (h) valine 60;
   (i) alanine 68;
   (j) phenylalanine 150;
   (k) threonine 178;
   (l) aspartate 183;
   (m) isoleucine 185;
   (n) threonine 220;
   (o) methionine 232;
   (p) valine 245;
   (q) alanine 257;
   (r) asparagine 259;
   (s) phenylalanine 261;
   (t) phenylalanine 275;
   (u) isoleucine 287;
   (v) histidine 289;
   (w) tyrosine 324;
   (x) glycine 326;
   (y) proline 356;
   (z) threonine 371;
   (aa) valine 396;
   (bb) proline 405;
   (cc) aspartate 431;
   (dd) isoleucine 436;
   (ee) isoleucine 457;
   (ff) aspartate 459;
   (gg) proline 470;
   (hh) glutamate 472;
   (ii) alanine 506; and
   (jj) isoleucine 507;
   or
   (II) a cystathionine gamma synthase, the amino acid sequence of which has at least 90% sequence identity to the amino acid sequence shown in SEQ ID NO: 3, by substitution or deletion of at least one amino acid residue corresponding to any one of (a) to (jj) listed above in SEQ ID NO: 3;
   or
   (III) the cystathionine gamma synthase of (i) or (ii) by deletion of one or more N-terminal amino acids corresponding to amino acids 1 to 103 of the amino acid sequence as shown in SEQ ID NO: 3, wherein substitution or deletion of at least one amino acid residue is present.

8. The protein of claim 7, which also shows the enzymatic activity of converting O-phospho-L-homoserine and sulfide into L-homocysteine+$H_3PO_4$.

9. A method for the production of S-adenosyl methionine comprising producing L-methionine according to the method of claim 1 and converting the L-methionine into S-adenosyl methionine.

10. A method for the production of cysteine comprising producing L-methionine according to the method of claim 1 and converting the L-methionine into cysteine.

11. A method for the production of glutathione comprising producing L-methionine according to the method of claim 1 and converting the L-methionine into glutathione.

12. A method for the production of 2-oxo-4-methylthiobutanoate comprising producing L-methionine according to the method of claim 1 and converting the L-methionine into 2-oxo-4-methylthio butanoate.

\* \* \* \* \*